United States Patent
Rairigh

(10) Patent No.: US 12,123,272 B2
(45) Date of Patent: Oct. 22, 2024

(54) METHODS OF PRE-TESTING EXPANSION CHARGE FOR SELECTIVELY EXPANDING A WALL OF A TUBULAR, AND METHODS OF SELECTIVELY EXPANDING WALLS OF NESTED TUBULARS

(71) Applicant: James G. Rairigh, Houston, TX (US)

(72) Inventor: James G. Rairigh, Houston, TX (US)

( * ) Notice: Subject to any disclaimer, the term of this patent is extended or adjusted under 35 U.S.C. 154(b) by 13 days.

(21) Appl. No.: 18/081,428

(22) Filed: Dec. 14, 2022

(65) Prior Publication Data

US 2023/0113807 A1  Apr. 13, 2023

Related U.S. Application Data

(60) Division of application No. 17/313,828, filed on May 6, 2021, now Pat. No. 11,536,104, which is a (Continued)

(51) Int. Cl.
*E21B 29/02* (2006.01)
*E21B 29/08* (2006.01)
(Continued)

(52) U.S. Cl.
CPC .............. *E21B 29/02* (2013.01); *E21B 29/08* (2013.01); *E21B 33/13* (2013.01); *E21B 43/103* (2013.01);
(Continued)

(58) Field of Classification Search
CPC .............. F42B 1/02; E21B 34/14; E21B 29/02
See application file for complete search history.

(56) References Cited

U.S. PATENT DOCUMENTS 2,214,226 A   9/1940 English
2,684,030 A   7/1954 Morris et al.
(Continued)

FOREIGN PATENT DOCUMENTS

EP  0079716 B1  3/1987
FR  1155464 A   5/1958
(Continued)

OTHER PUBLICATIONS

International Search Report and Written Opinion of the International Searching Authority, issued by the U.S. Patent & Trademark Office in PCT/2019/046920 on Jan. 9, 2020 (57 pages).
(Continued)

*Primary Examiner* — David Carroll
(74) *Attorney, Agent, or Firm* — McCutcheon Joseph, PLLC

(57) ABSTRACT

A method involves determining an expansion charge able to selectively expand, without perforating or cutting through, a wall of a tubular in a wellbore. The method includes determining conditions in the wellbore, including hydrostatic pressure bearing on the tubular in the wellbore, and a physical characteristic of the tubular. At a second location other than the wellbore, at least one of the conditions determined in the wellbore is reproduced, and a test tubular is provided at the second location. A test expansion charge able to expand, without perforating or cutting through, the wall of the test tubular, is determined based on the determined conditions. The determined test expansion charge is positioned within the test tubular, and is then actuated to expand the wall of the test tubular radially outward, without perforating or cutting through the wall, to form a test protrusion in the wall of the test tubular.

18 Claims, 34 Drawing Sheets

Related U.S. Application Data continuation-in-part of application No. 17/126,982, filed on Dec. 18, 2020, now Pat. No. 11,480,021, which is a continuation-in-part of application No. 16/970,602, filed as application No. PCT/US2019/046920 on Aug. 16, 2019, now Pat. No. 11,002,097.

(60) Provisional application No. 62/764,858, filed on Aug. 16, 2018.

(51) Int. Cl.
*E21B 33/13* (2006.01)
*E21B 43/10* (2006.01)
*F42B 3/08* (2006.01)
*G01N 33/22* (2006.01)
*E21B 17/10* (2006.01)

(52) U.S. Cl.
CPC .............. *F42B 3/08* (2013.01); *G01N 33/227* (2013.01); *E21B 17/1028* (2013.01)

(56) References Cited

U.S. PATENT DOCUMENTS

| | | | |
|---|---|---|---|
| 3,013,333 | A | 12/1961 | Burke |
| 3,167,122 | A | 1/1965 | Lang |
| 3,590,877 | A | 7/1971 | Leopold et al. |
| 4,184,430 | A | 1/1980 | Mock |
| 4,449,280 | A | 5/1984 | Schroeder |
| 4,585,374 | A | 4/1986 | Regalbuto et al. |
| 4,672,832 | A | 6/1987 | Merker |
| 4,724,767 | A | 2/1988 | Aseltine |
| 4,850,438 | A | 7/1989 | Regalbuto |
| 4,966,237 | A | 10/1990 | Swanson et al. |
| 5,038,683 | A | 8/1991 | Baker et al. |
| 5,753,850 | A | 5/1998 | Chawla et al. |
| 7,104,326 | B2 | 9/2006 | Grattan et al. |
| 8,939,210 | B2 | 1/2015 | Bell et al. |
| 9,022,116 | B2 | 5/2015 | Bell et al. |
| 9,360,222 | B1* | 6/2016 | Collier ................. F24B 1/028 |
| 10,316,627 | B2 | 6/2019 | Brisco et al. |
| 2002/0157830 | A1 | 10/2002 | Simpson |
| 2003/0221579 | A1* | 12/2003 | Grattan ............... F42B 1/02 102/306 |
| 2004/0154492 | A1 | 8/2004 | Barnhart |
| 2004/0251034 | A1* | 12/2004 | Kendziora ........... E21B 33/14 166/384 |
| 2005/0061506 | A1 | 3/2005 | Grove et al. |
| 2006/0075888 | A1* | 4/2006 | Yang ..................... F42B 3/08 89/1.14 |
| 2006/0086501 | A1 | 4/2006 | Creel et al. |
| 2011/0094406 | A1* | 4/2011 | Marya ................... F42B 1/02 102/305 |
| 2012/0312561 | A1 | 12/2012 | Hallundbæk et al. |
| 2013/0214183 | A1* | 8/2013 | Wilie .................... E21B 33/06 251/1.1 |
| 2013/0299194 | A1* | 11/2013 | Bell ........................ F42B 1/028 73/35.14 |
| 2014/0076550 | A1 | 3/2014 | Pelletier et al. |
| 2014/0338910 | A1 | 11/2014 | Bell et al. |
| 2015/0198000 | A1 | 7/2015 | Bell et al. |
| 2015/0233219 | A1 | 8/2015 | Bell et al. |
| 2015/0361774 | A1 | 12/2015 | Flores |
| 2016/0010423 | A1* | 1/2016 | Myhre ................... E21B 37/00 166/285 |
| 2016/0032706 | A1 | 2/2016 | Bornaz et al. |
| 2016/0123122 | A1 | 5/2016 | Van Dongen et al. |
| 2016/0130902 | A1* | 5/2016 | Wright ................... F42C 19/02 89/1.15 |
| 2017/0145778 | A1 | 5/2017 | Zijsling et al. |
| 2017/0145797 | A1 | 5/2017 | Stam et al. |
| 2017/0191328 | A1 | 7/2017 | Sokolove et al. |
| 2018/0030334 | A1* | 2/2018 | Collier ................. E21B 43/26 |
| 2018/0094504 | A1 | 4/2018 | Hearn et al. |
| 2018/0187528 | A1 | 7/2018 | Di Crescenzo et al. |
| 2018/0216437 | A1* | 8/2018 | Shafer ................... E21B 33/134 |
| 2018/0252507 | A1 | 9/2018 | Collier |
| 2018/0298720 | A1* | 10/2018 | Billingham ........... E21B 33/138 |

FOREIGN PATENT DOCUMENTS

| | | |
|---|---|---|
| JP | 4017111 B2 | 12/2007 |
| NO | 20180152 A1 | 4/2018 |
| WO | WO2014/108431 A2 | 7/2014 |
| WO | 2014148913 A1 | 9/2014 |
| WO | 2014202419 A1 | 12/2014 |
| WO | WO2020/016169 A1 | 1/2020 |

OTHER PUBLICATIONS

International Preliminary report on Patentability, issued by the U.S. Patent & Trademark Office in PCT/2019/046920 on Jun. 25, 2020 (12 pages).

International Search Report and Written Opinion of the International Searching Authority, issued by the U.S. Patent & Trademark Office in PCT/2019/046692 on Nov. 6, 2019 (80 pages).

Written Opinion of the International Preliminary Examining Authority, issued by the U.S. Patent & Trademark Office in PCT/2019/046692 on Aug. 11, 2020 (5 pages).

Office Action issued by the U.S. Patent & Trademark Office on Nov. 2, 2020 in U.S. Appl. No. 16/970,605 (15 pages).

Office Action issued by the U.S. Patent & Trademark Office on Nov. 24, 2020 in U.S. Appl. No. 16/970,602 (23 pages).

Office Action issued by the Canadian Intellectual Property Office on Mar. 10, 2021 in CA Patent Application No. 3,109,219 (7 pages).

Office Action issued by the Canadian Intellectual Property Office on Mar. 18, 2021 in CA Patent Application No. 3,109,407 (4 pages).

European Extended Search Report cited in EP 19849212.6 on Apr. 7, 2022 (7 pages).

European Extended Search Report cited in EP 19849454.4 on Apr. 19, 2022 (10 pages).

Office Action issued by the U.S. Patent & Trademark Office on Jun. 23, 2022 in U.S. Appl. No. 17/240,611.

Office Action issued by the United States Patent and Trademark Office on Mar. 8, 2022 in U.S. Appl. No. 17/126,982 (25 pages).

* cited by examiner

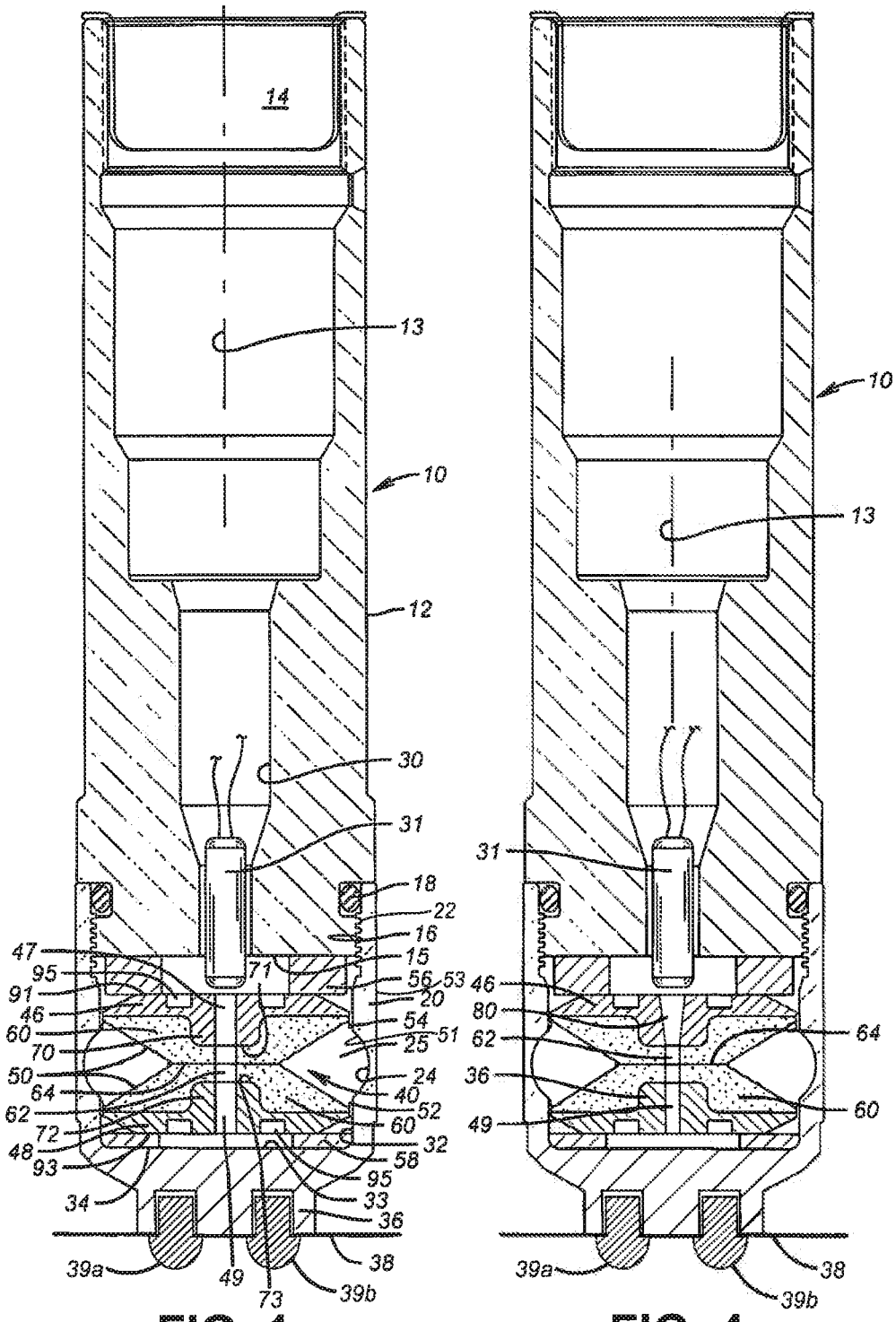

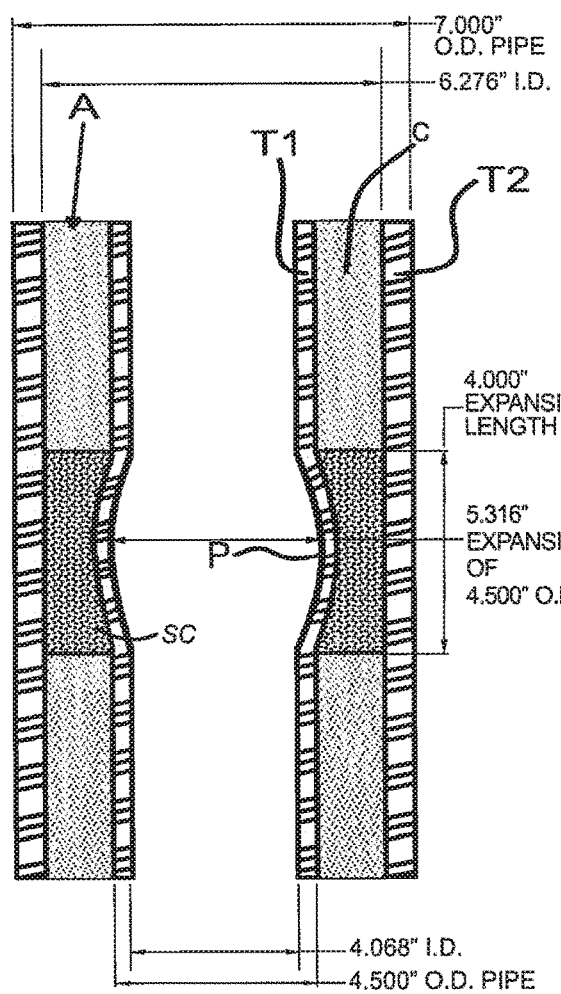
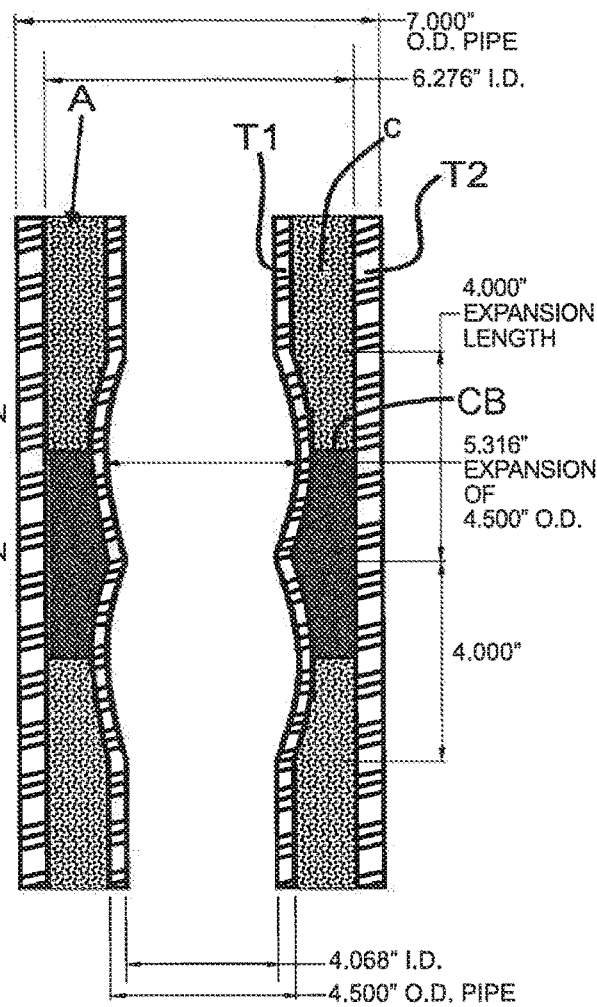
FIG. 2C  FIG. 2D

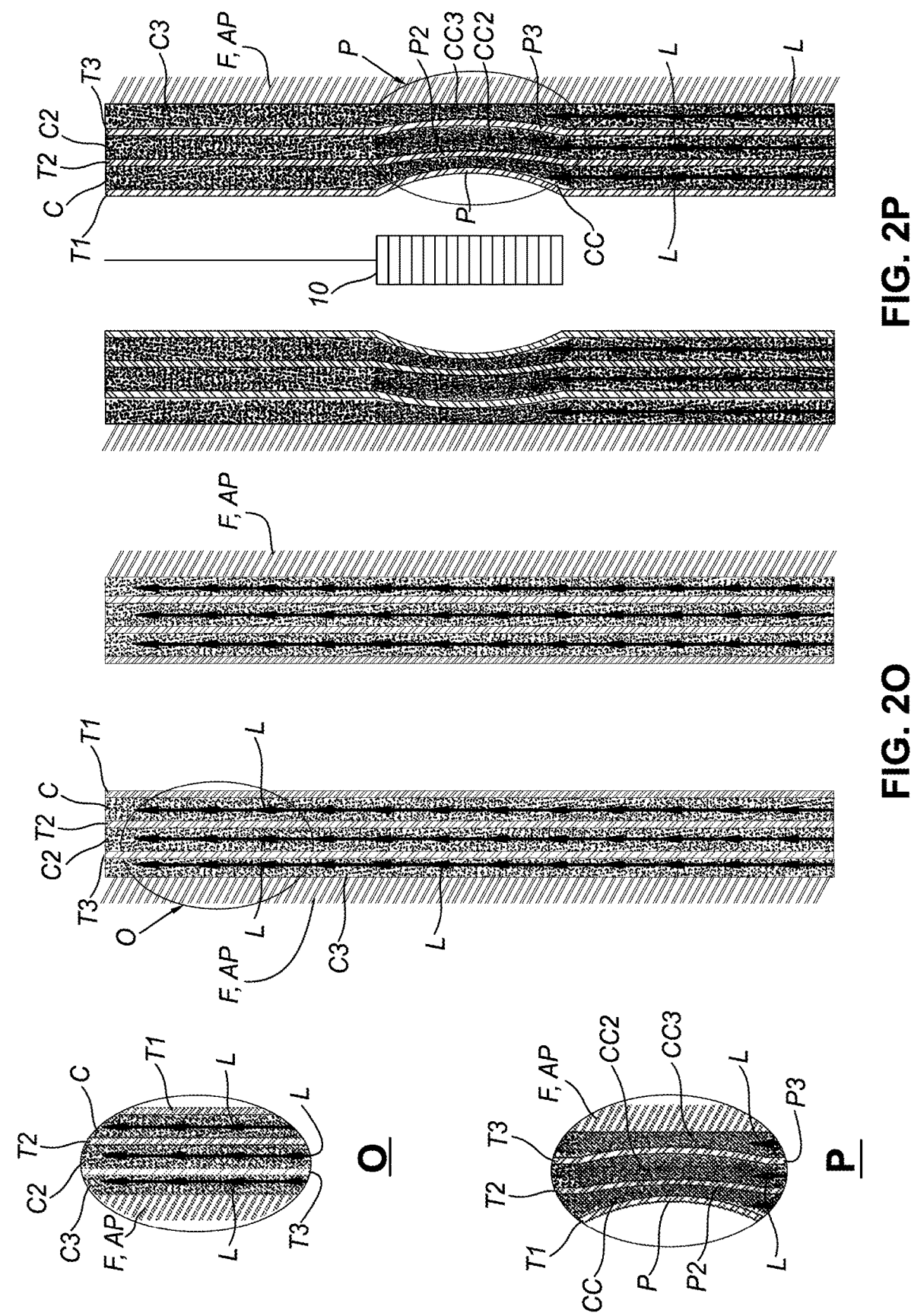

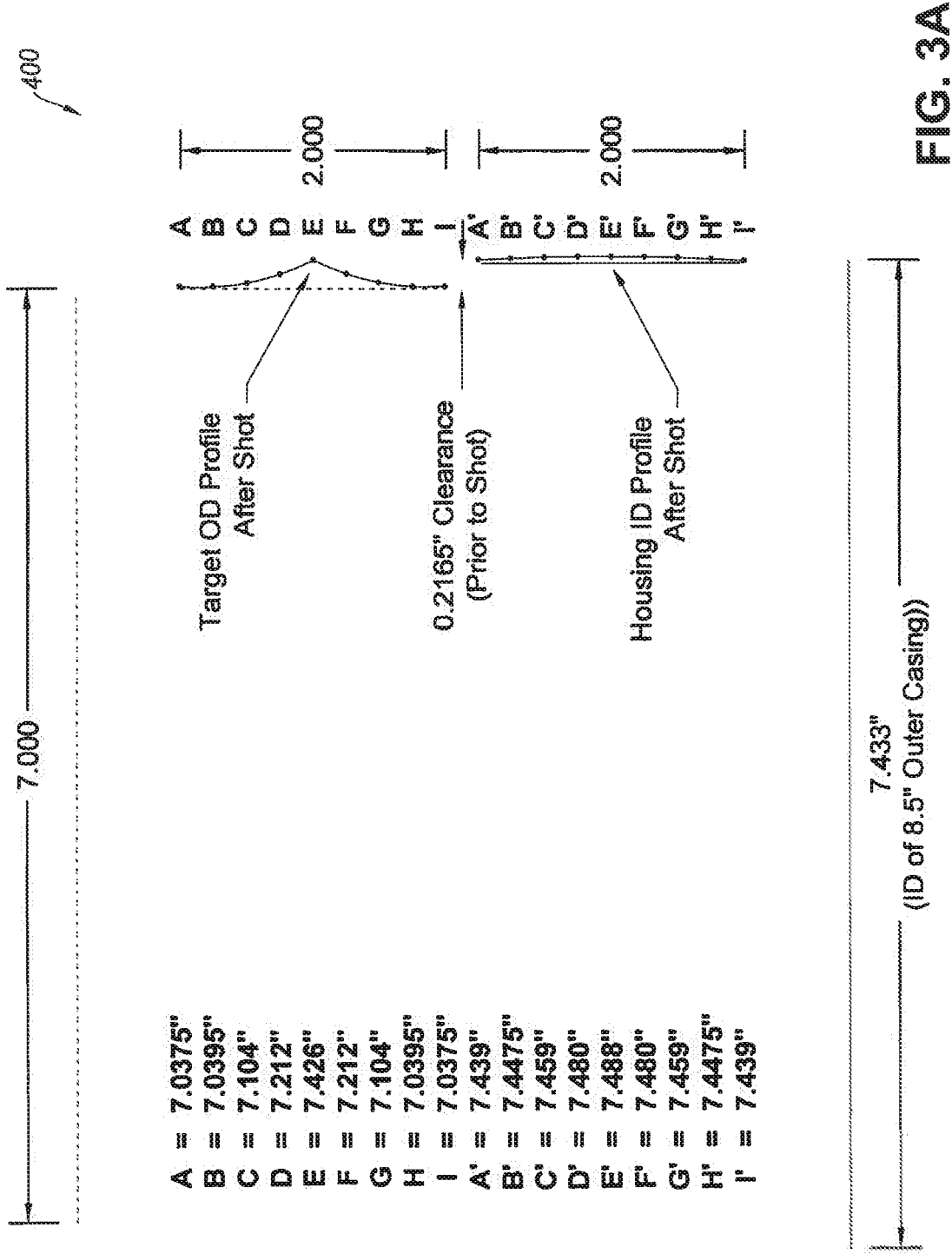

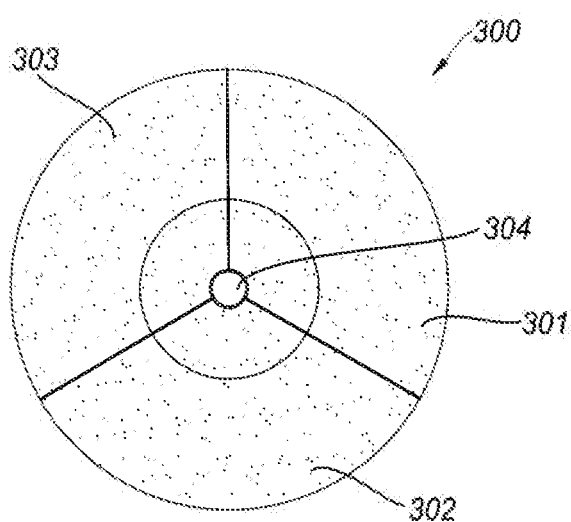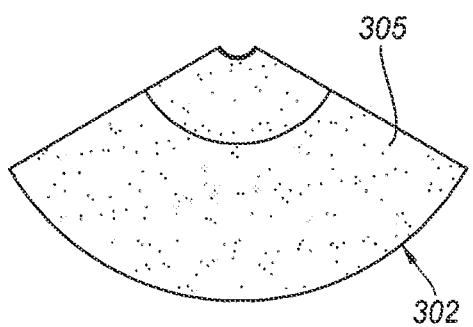
FIG. 14  FIG. 15
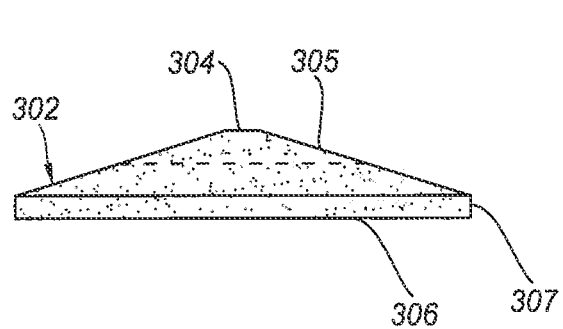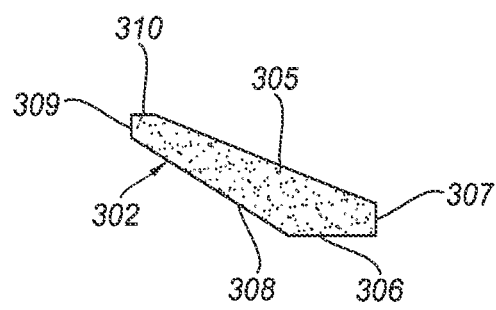
FIG. 16  FIG. 17

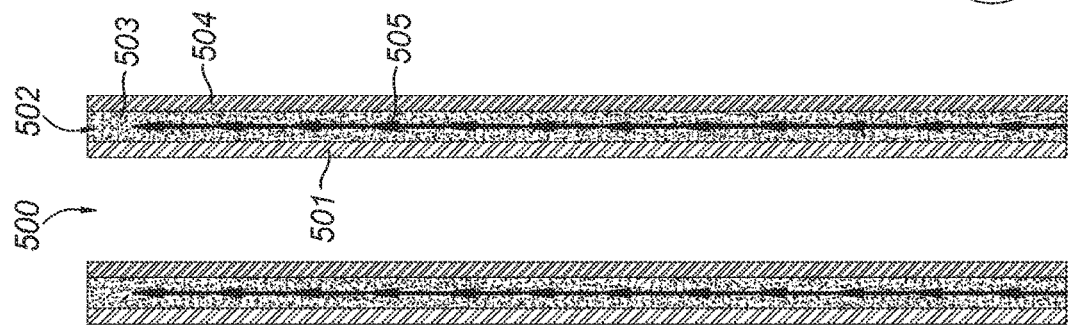
FIG. 26D
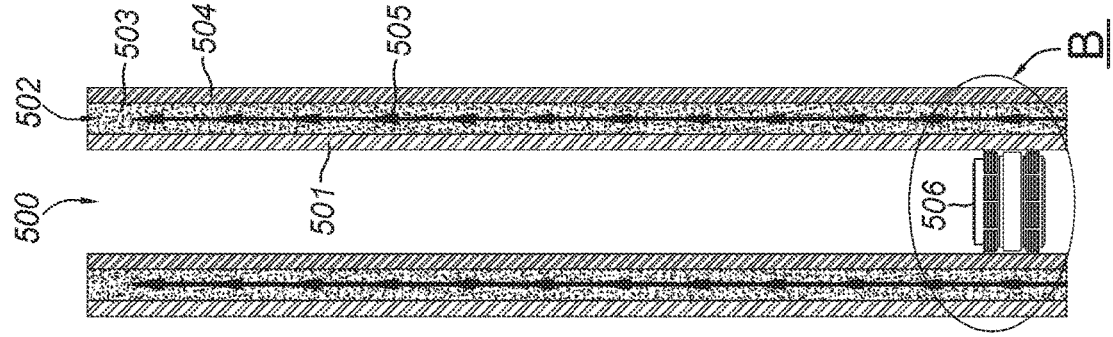
FIG. 26C
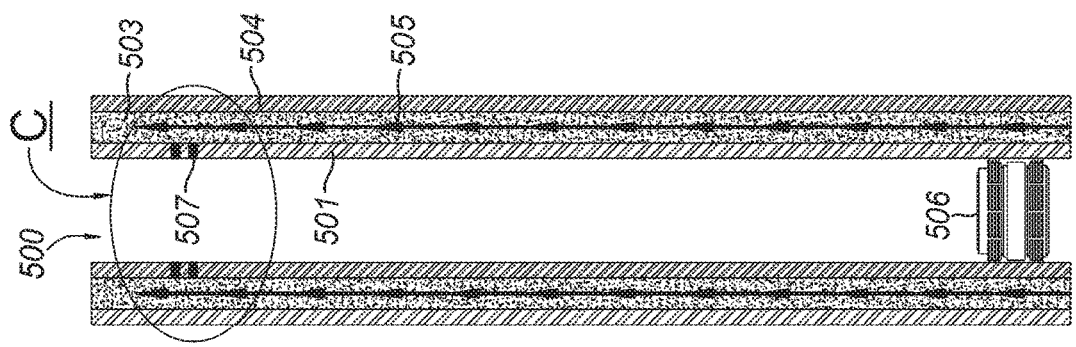
FIG. 26B
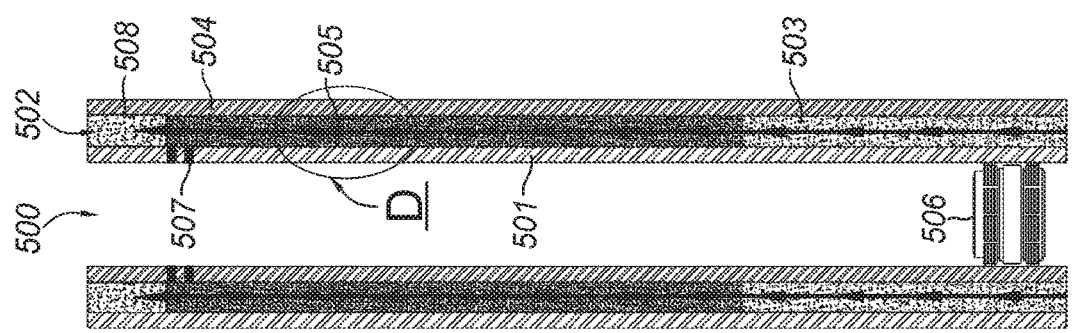
FIG. 26A
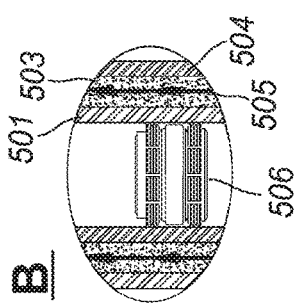
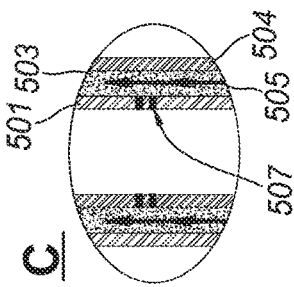
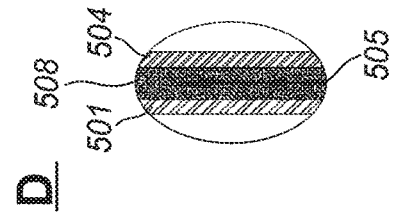

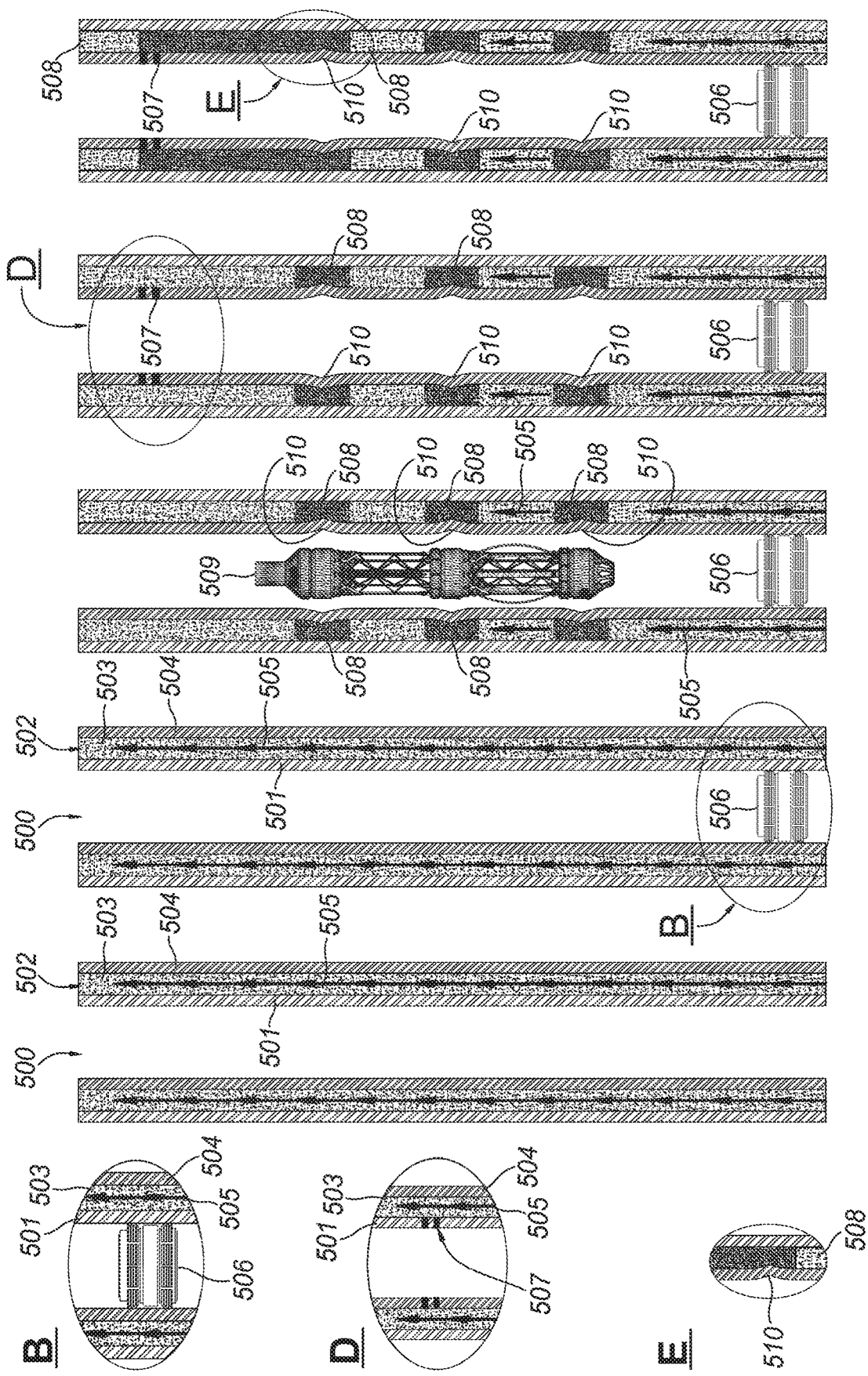

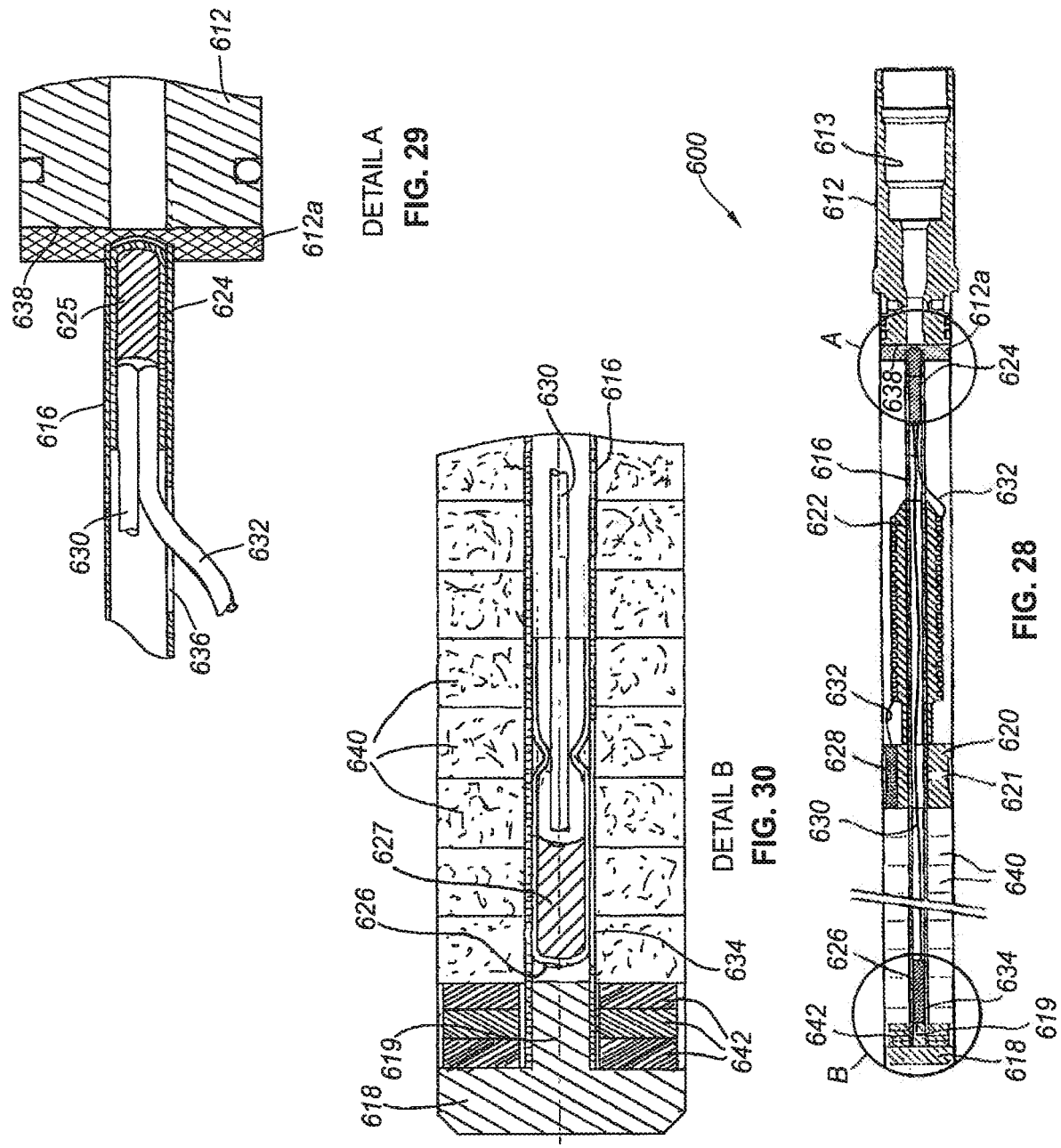

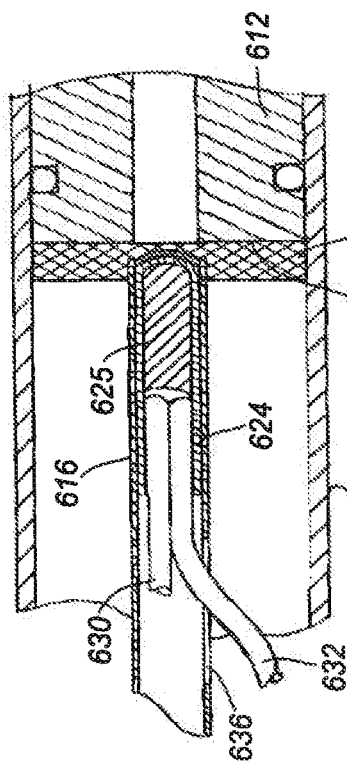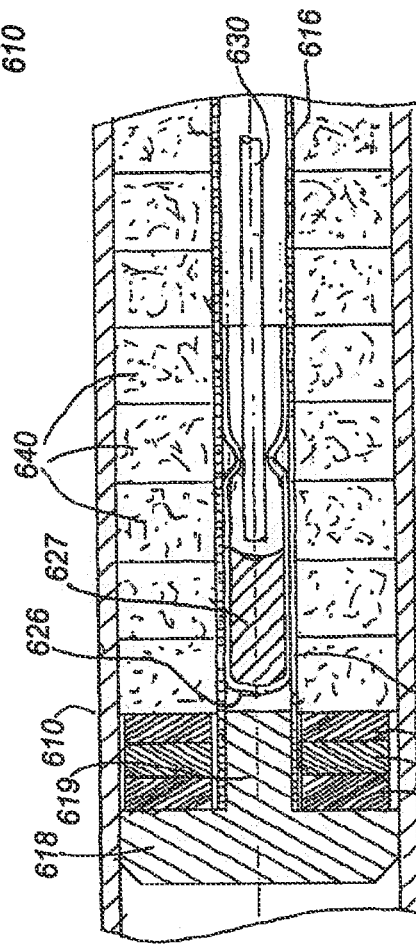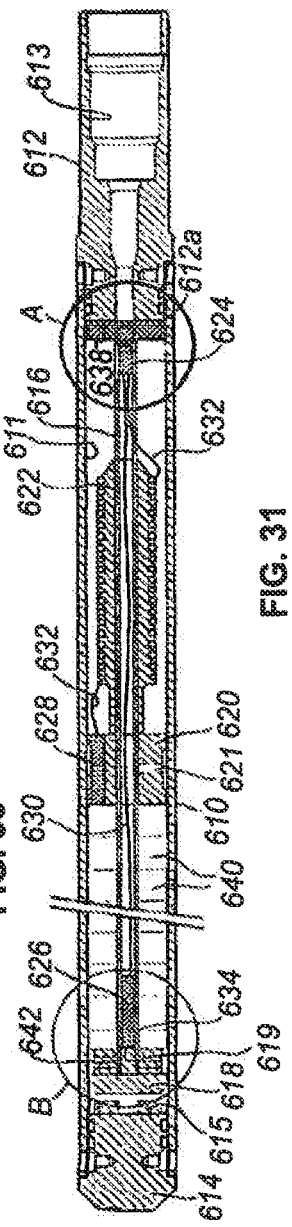

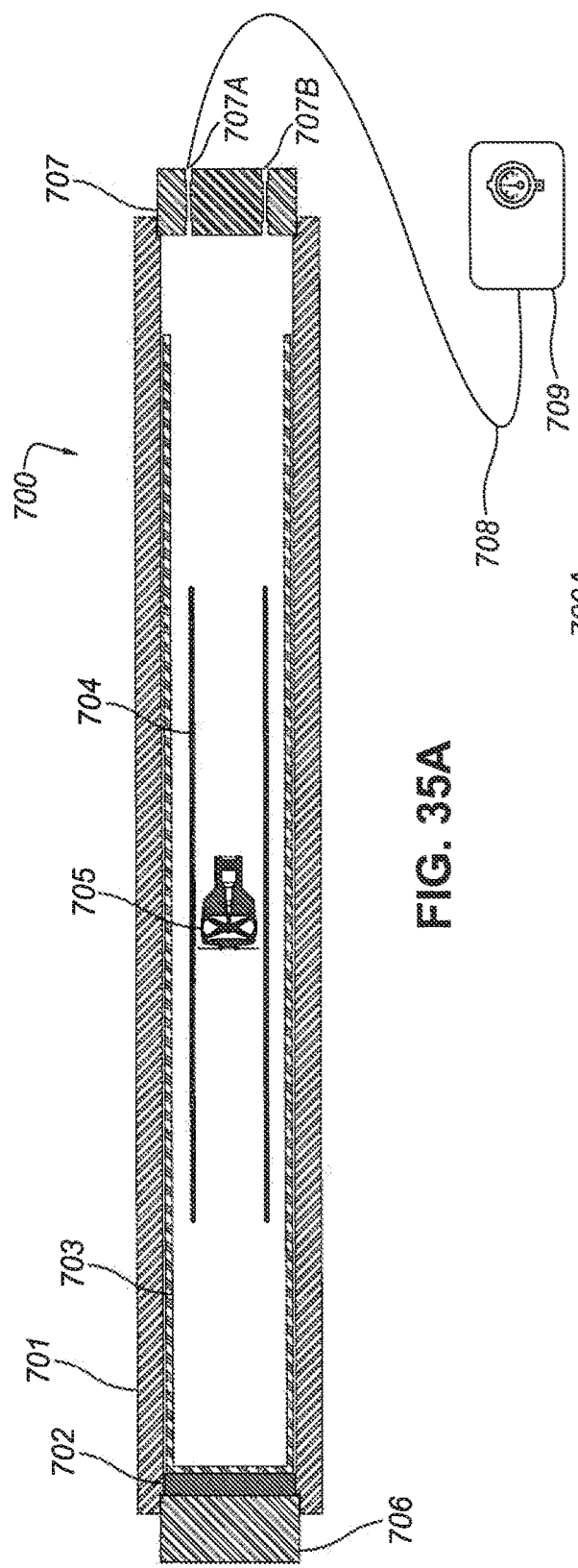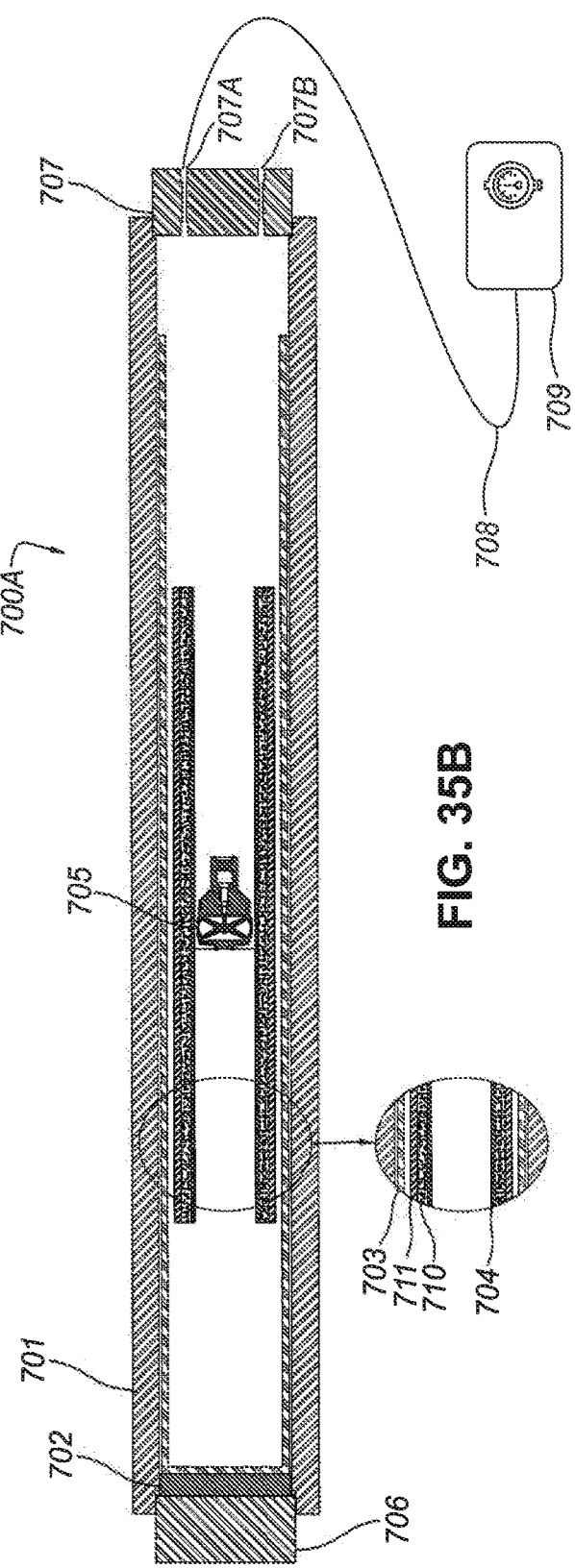
FIG. 35A
FIG. 35B

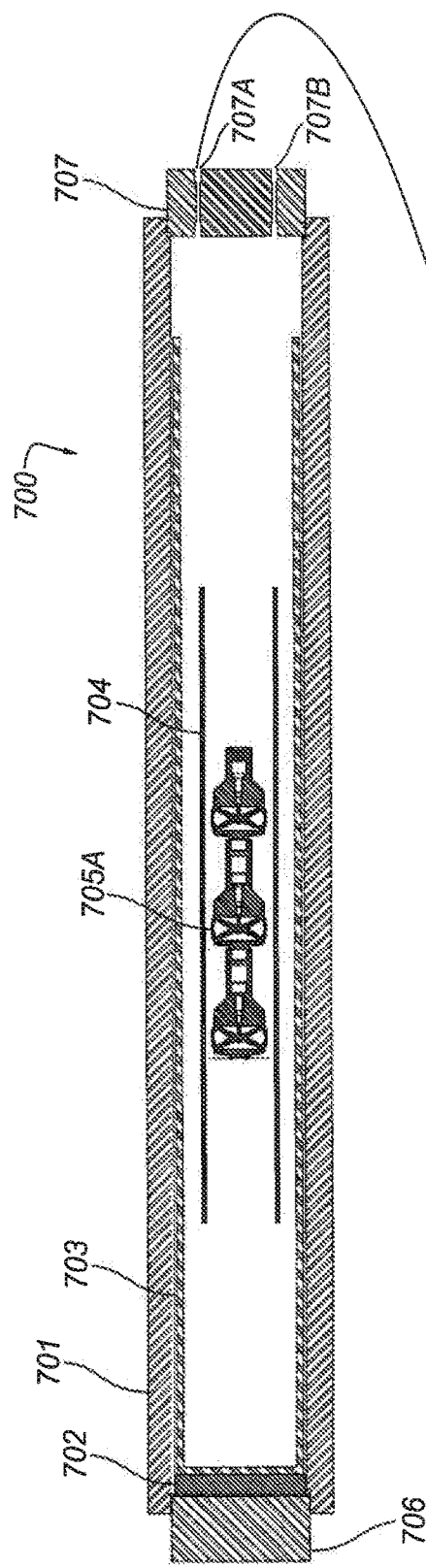
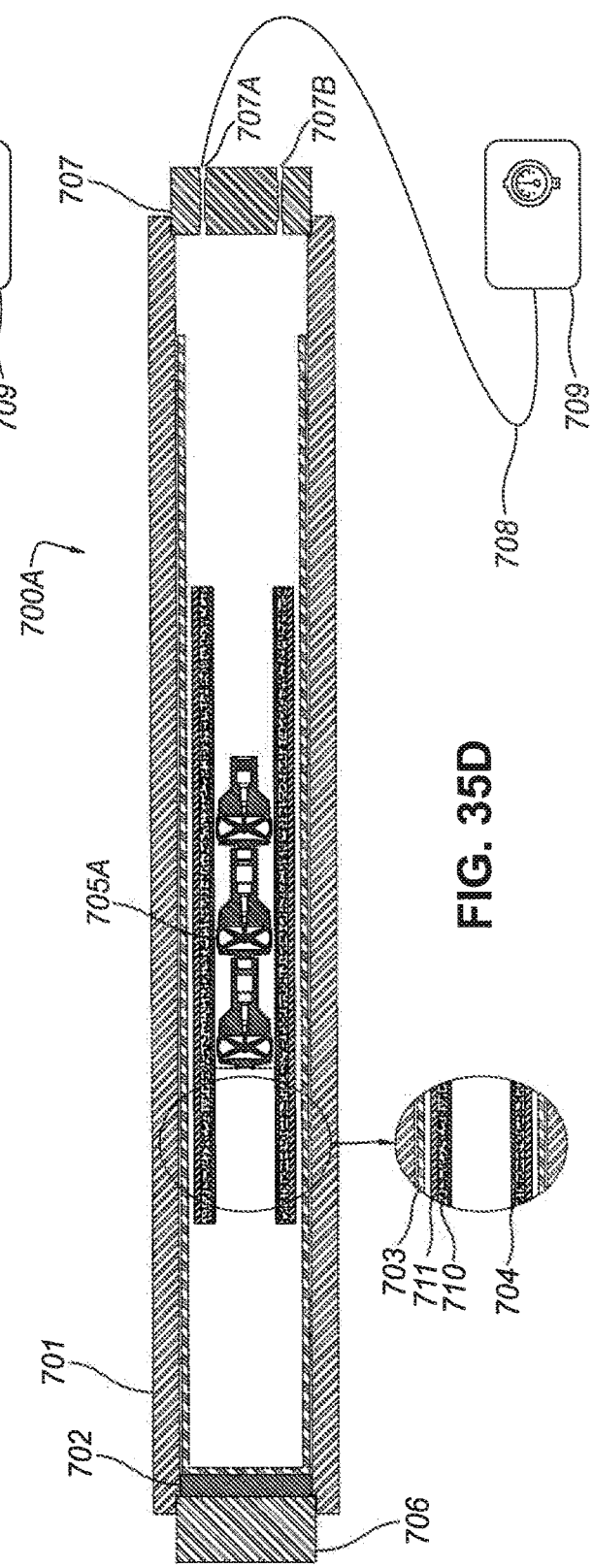
FIG. 35C
FIG. 35D

METHODS OF PRE-TESTING EXPANSION CHARGE FOR SELECTIVELY EXPANDING A WALL OF A TUBULAR, AND METHODS OF SELECTIVELY EXPANDING WALLS OF NESTED TUBULARS

CROSS REFERENCE TO RELATED APPLICATIONS

The present application is a divisional of U.S. patent application Ser. No. 17/313,828 filed on May 6, 2021, which is a continuation-in-part of U.S. patent application Ser. No. 17/126,982 filed on Dec. 18, 2020, which is a continuation-in-part of U.S. patent application Ser. No. 16/970,602 filed on Aug. 17, 2020, which is a national phase of International Application PCT/2019/046920 filed on Aug. 16, 2019, which claims priority to U.S. Provisional Patent Application No. 62/764,858 filed on Aug. 16, 2018, with all patents and patent applications, as set forth above, having a title of "Shaped Charge Assembly, Explosive Units, and Methods for Selectively Expanding Wall of a Tubular," The contents of the prior applications are hereby incorporated by reference herein in their entirety.

FIELD

Embodiments of the present invention relate, generally, to methods of pre-testing expansion charges of an expansion charge tool for selectively expanding a wall of a tubular. The tubular may include, but is not limited to, pipe, tube, casing and/or casing liner. Expansion charge tools, such as shaped charge tools, may be used for selectively expanding a wall of a tubular to compress micro annulus pores and reduce micro annulus leaks, collapse open channels in a cemented annulus adjacent the tubular, minimize other inconstancies or defects in the cemented annulus, and to form a restriction. The present disclosure relates to methods of pre-testing expansion charges of an expansion charge tool under simulated conditions, or under conditions that are transferrable to a downhole application, before the expansion charge tool is actually used in the wellbore onsite to selectively expand a wall of a tubular. The simulated conditions are based on the actual conditions determined in the onsite wellbore. The pre-testing may help tune the expansion charge as close as possible/practical to the actual downhole conditions. The pre-testing under simulated conditions helps ensure that the expansion charge provides an adequate or desired wall expansion (e.g., protrusion) of the wellbore tubular, without perforating or cutting through the wall of the tubular, when the expansion charge is actuated in the wellbore.

Embodiments of the present invention also relate, generally, to methods of selectively expanding walls of multiple nested tubulars with a single actuation of an expansion charge tool.

BACKGROUND

Pumping cement into a wellbore may be part of a process of preparing a well for further drilling, production or abandonment. The cement is intended to protect and seal tubulars in the wellbore. Cementing is commonly used to permanently shut off water and gas migration into the well. As part of the completion process of a prospective production well, cement may be used to seal an annulus after a casing string has been run in the wellbore. Additionally, cementing may be used to seal a lost circulation zone, or an area where there is a reduction or absence of flow within the well. Cementing is used to plug a section of an existing well, in order to run a deviated well from that point. Also, cementing may be used to seal off all leak paths from the earth's downhole strata to the surface in plug and abandonment operations, at the end of the well's useful life.

Cementing is performed when a cement slurry is pumped into the well, displacing the drilling fluids still located within the well, and replacing them with cement. The cement slurry flows to the bottom of the wellbore through the casing. From there, the cement fills in the annulus between the casing and the actual wellbore, and hardens. This creates a seal intended to impede outside materials from entering the well, in addition to permanently positioning the casing in place. The casing and cement, once cured, helps maintain the integrity of the wellbore.

Although the cement material is intended to form a water tight seal for preventing outside materials and fluids from entering the wellbore, the cement material is generally porous. As such, water, gas, or other outside materials may eventually seep into the micro pores of the cement, and penetrate through the hardened concrete seal. Over time, these outside materials and fluids can seep into the micro pores of the cement and cause cracks, micro annulus leak paths, decay and/or contamination of the cement material and the wellbore. Further, the cement in the cemented annulus may inadvertently include open channels, sometimes referred to as "channel columns" that undesirably allow gas and/or fluids to flow through the channels, thus raising the risk of cracks, decay and/or contamination of the cement and wellbore. In other situations, the cement may inadvertently not be provided around the entire 360 degree circumference of the casing. This may occur especially in horizontal wells, where gravity acts on the cement above the casing in the horizontal wellbore. Further, shifts in the strata (formation) of the earth may cause cracks in the cement, resulting in "channel columns" in the cement where annulus flow would otherwise not occur. Other inconsistencies or defects of the cement in the annulus may arise from inconsistent viscosity of the cement, and/or from a pressure differential in the formation that causes the cement to be inconsistent in different areas of the annulus.

Therefore, a need exists for systems and methods that are usable to efficiently reduce and/or compress micro annulus pores in the cement or other sealing materials for minimizing or eliminating the formation of cracks, micro annulus leaks, decay and/or contamination of the cement and wellbore. A need also exists for cost effective and efficient methods that are usable to selectively expand a wall or portion of the walls of several nested tubular goods to compress micro annulus pores and reduce or eliminate micro annulus leaks in the nested annuli between the nested tubular goods with only one (i.e., a single) actuation of an expansion charge tool. In addition, a need exists for cost effective and efficient methods that, with only one actuation of an expansion charge tool, selectively expand the walls or portion of walls of nested tubular goods to effectively collapse and/or compress open channels in the nested cemented annuli between the nested tubular goods, and/or compress the nested cemented annuli to cure other defects or inconsistencies in the cement to minimize or eliminate the unintended flow of gas and/or fluids through the cemented annuli upward toward the surface into the atmosphere.

Moreover, not all wellbores are the same. Conditions, such as the fluid/gas medium present (e.g., air, water, nitrogen), hydrostatic pressure, and physical dimensions, among other things, may vary from wellbore to wellbore. In addition, tubulars disposed in wellbores may vary in size, grade, weight, and other physical characteristics. Accordingly, an expansion charge that may be effective in one tubular of a given wellbore may not be effective in another tubular of another wellbore based on variations on any of the above factors.

In this regard, a further need exists for methods of pre-testing expansion charges of an expansion charge tool, based on specific conditions that exist in a wellbore and/or physical properties of the tubular set in the wellbore, before the expansion charge tool is actually used in the wellbore to selectively expand a wall of the tubular in the wellbore.

The embodiments of the present invention meet all of these needs.

SUMMARY

An object of the present disclosure is to provide tools and methods that compress micro annulus pores in cement to further restrict/seal off micro annulus leaks migrating up a cement column in a well bore to conform to industry and/or regulatory standards. Compressing the cement reduces the porosity of the cement by reducing the number of micro annulus pores. The reduced number of micro annulus pores reduces the risk of seepage into the cement as well as the formation of micro annulus leak paths. Another object of the present disclosure is to provide tools and methods that effectively collapse and/or compress open channels in a cemented annulus, and/or that effectively compress the cemented annulus to cure other defects or inconsistencies in the cement that would otherwise allow unintended flow of gas and/or fluids through the cemented annuls. Generally, all deleterious flow through the cemented annulus caused by the above situations may be referred to as annulus flow, and the disclosure herein discusses apparatus and methods for reducing or eliminating annulus flow.

Explosive, mechanical, chemical or thermite cutting devices have been used in the petroleum drilling and exploration industry to cleanly sever a joint of tubing or casing deeply within a wellbore. Such devices are typically conveyed into a well for detonation on a wireline or length of coiled tubing. The devices may also be pumped downhole. Known shaped charge explosive cutters include a consolidated amount of explosive material having an external surface clad with a thin metal liner. When detonated at the axial center of the packed material, an explosive shock wave, which may have a pressure force as high as 3,000,000 psi, can advance radially along a plane against the liner to fluidize the liner and drive the fluidized liner lineally and radially outward against the surrounding pipe. The fluidized liner forms a jet that hydro-dynamically cuts through and severs the pipe. Typically, the diameter of the jet may be around 5 to 10 mm. The inventor of the present application has determined that, in some cases, removing the liner from the explosive material reduces the focus of the explosive shock wave so that the wall of a pipe or other tubular member is not penetrated or severed. Instead, the explosive shock wave results in a selective, controlled expansion of the wall of the pipe or other tubular member. The liner-less shaped charge has a highly focused explosive wave front where the tubular expansion may be limited to a length of about 10.16 centimeters (4 inches) along the outside diameter of the pipe or other tubular member. Too much explosive material, even without a liner, may still penetrate the pipe or other tubular member. On the other hand, too little explosive material may not expand the pipe or other tubular member enough to achieve its intended effect. Selective expansion of the pipe or other tubular member at strategic locations along the length thereof can compress the cement that is set in an annulus adjacent the wall of the pipe or other tubular member, or of the wellbore, beneficially reducing the porosity of the cement by reducing the number of micro annulus pores, and thus the associated risk of micro annulus leaks. The expanded wall of the pipe or other tubular member, along with the compressed cement, forms a barrier. The expanded wall of the pipe or other tubular member may also collapse and/or compress open channels in a cemented annulus, and/or may compress the cemented annulus to cure other defects or inconsistencies in the cement (such as due to inconsistent viscosity of the cement, and/or a pressure differential in the formation).

As discussed above, conditions in a wellbore, such as the fluid/gas medium present (e.g., air, water, nitrogen), hydrostatic pressure, and physical dimensions, among other things, may vary from wellbore to wellbore. Accordingly, an expansion charge that may be effective in one tubular of a given wellbore configuration may not be effective in another tubular of another wellbore configuration. And, tubulars disposed in wellbores may vary in size, grade, weight, and other physical characteristics. It may thus be helpful to determine beforehand, based on the specific conditions that exist in a wellbore and/or physical properties of the tubular set in the wellbore, a specific expansion charge that is to be used on the tubular in that wellbore. In such case, the specific expansion charge can be designed based on those conditions to ensure that the expansion charge sufficiently expands, without perforating or cutting through, the wall of the tubular in the wellbore. The simulated or transferrable conditions may be based on the actual conditions determined in the onsite wellbore. The pre-testing under simulated or transferrable conditions helps ensure that the expansion charge provides an adequate or desired wall expansion (e.g., protrusion) of the wellbore tubular, without perforating or cutting through the wall of the tubular, when the expansion charge is actuated in the onsite wellbore. The pre-testing also helps establish a safety factor against breaching the actual tubular in the wellbore because if the expansion charge does not rupture the test tubular that is unconfined in the test or is at zero or relatively low pressure, then the same expansion charge should not rupture the actual tubular in the wellbore that is confined (e.g., by cement) or under relatively large pressure.

One embodiment of the disclosure relates to a method of determining a size and an explosive gram weight of an expansion charge able to selectively expand, without perforating or cutting through, a portion of a wall of a tubular in a wellbore. The method comprises: determining conditions in the wellbore, including: fluid/gas medium in the wellbore; hydrostatic pressure bearing on the tubular in the wellbore; and at least one physical characteristic of the tubular. The method can continue by reproducing, at a second location other than the wellbore, at least one of the conditions determined in the wellbore; providing a test tubular at the second location; determining a size and an explosive gram weight of a test expansion charge able to expand, without perforating or cutting through, the wall of the test tubular, based on the at least one of the conditions determined in the wellbore; positioning the test expansion charge comprising the determined size and explosive gram weight within the test tubular; and actuating the test expansion charge to expand the wall of the test tubular radially outward, without perforating or cutting through the wall of the test tubular, to form a test protrusion in the wall of the test tubular.

In an embodiment, the method can further comprise selecting the determined size and explosive gram weight, or a different size and explosive gram weight, for an expansion charge for expanding, without perforating or cutting through, the portion of the wall of the tubular in the wellbore.

In an embodiment, the at least one physical characteristic of the tubular comprises a material, a grade, a weight, an inner diameter, and an outer diameter.

In an embodiment, the test expansion charge may be a shaped charge for use in a shaped charged expansion tool.

In an embodiment, the method further comprises determining a size of a protrusion to be formed in the wall of the tubular.

In an embodiment, the fluid/gas medium can comprise at least one of air, water, and nitrogen.

In an embodiment, the fluid/gas medium can comprise at least one of drilling fluid, completion fluid, acidizing fluid, salt water, and fresh water.

In an embodiment, the test tubular at the second location may be unconfined such that an outer surface of the test tubular is exposed to a fluid/gas medium at the second location.

In an embodiment, the test tubular at the second location may be confined such that an annulus adjacent an outer surface of the test tubular contains a solid material.

In an embodiment, the solid material may be at least one of sand, cement, and a material present in an annulus adjacent an outer surface of the tubular in the wellbore.

In an embodiment, the test tubular at the second location may be confined when the hydrostatic pressure in the wellbore is 5000 psi or less. In an embodiment, the second location comprises one of a vessel and an open body of water.

Another embodiment of the disclosure relates to a method of determining an expansion charge able to selectively expand, without perforating or cutting through, a portion of a wall of a tubular in a wellbore. The method comprises: determining conditions in the wellbore, including: hydrostatic pressure bearing on the tubular in the wellbore, and at least one physical characteristic of the tubular; reproducing, at a second location other than the wellbore, at least one of the conditions determined in the wellbore; providing a test tubular at the second location; determining a test expansion charge able to expand, without perforating or cutting through, the wall of the test tubular, based on the at least one of the conditions determined in the wellbore; positioning the determined test expansion charge within the test tubular; and actuating the determined test expansion charge to expand the wall of the test tubular radially outward, without perforating or cutting through the wall of the test tubular, to form a test protrusion in the wall of the test tubular.

In an embodiment, the method can further comprise selecting the determined test expansion charge or a different expansion charge, for expanding, without perforating or cutting through, the portion of the wall of the tubular in the wellbore.

In an embodiment, the test expansion charge may be a shaped charge for use in a shaped charged expansion tool.

In an embodiment, the method further comprises a fluid/gas medium in the wellbore as part of the determining conditions in the wellbore.

In an embodiment, the fluid/gas medium can comprise at least one of air, water, nitrogen, drilling fluid, completion fluid, acidizing fluid, salt water, and fresh water.

In an embodiment, the test tubular at the second location may be confined such that an annulus adjacent an outer surface of the test tubular contains at least one of sand, cement and a material present in an annulus adjacent an outer surface of the tubular in the wellbore.

In an embodiment, the test tubular at the second location may be unconfined such that an outer surface of the test tubular is exposed to a fluid/gas medium at the second location.

A further embodiment of the disclosure relates to a method of selectively expanding walls of at least three nested tubulars comprising an innermost tubular, an outermost tubular, and at least one intermediate tubular between the innermost tubular and the outermost tubular. The method comprises positioning an expansion tool within the innermost tubular, wherein the expansion tool contains an amount of explosive material based at least in part on: (1) a hydrostatic pressure bearing on at least one of the innermost tubular, the at least one intermediate tubular, and the outermost tubular; and (2) the amount of explosive material for producing an explosive force sufficient to expand, without puncturing, a wall of the innermost tubular, a wall of the at least one intermediate tubular, and a wall of the outermost tubular. The method can continue by actuating the expansion tool once to expand radially outward the wall of the innermost tubular, the wall of the at least one intermediate tubular, and the wall of the outermost tubular, without perforating or cutting through the wall of the innermost tubular, the wall of the at least one intermediate tubular, and the wall of the outermost tubular, to form a protrusion of the wall of the innermost tubular that extends into an annulus between the innermost tubular and the at least one intermediate tubular, to form a nested intermediate protrusion of the wall of the at least one intermediate tubular that extends into an annulus between the at least one intermediate tubular and the outermost tubular, and to form a nested outermost protrusion of the wall of the outermost tubular that extends into an annulus adjacent an outer surface of the wall of the outer tubular.

In an embodiment, the at least one intermediate tubular comprises two or more nested tubulars between the innermost tubular and the outermost tubular, and the method comprises radially expanding nested walls of the two or more nested tubulars when the expansion tool is actuated once, to form nested protrusions in the nested walls of the two or more nested tubulars.

Another embodiment of the disclosure relates to a method of sealing at least one of a first annulus between an innermost tubular and a nested intermediate tubular, a second annulus between the intermediate tubular and a nested outer tubular, and a third annulus adjacent an outer surface of the nested outer tubular. The method comprises positioning an expansion tool within the innermost tubular, wherein the expansion tool contains an amount of explosive material based at least in part on: (1) a hydrostatic pressure bearing on at least one of the innermost tubular, the nested intermediate tubular, and the nested outermost tubular; and (2) the amount of explosive material for producing an explosive force sufficient to expand, without puncturing, a wall of the innermost tubular, a wall of the nested intermediate tubular, and a wall of the nested outermost tubular. The method can continue by actuating the expansion tool once to expand radially outward the wall of the innermost tubular, the wall of the nested intermediate tubular, and the wall of the nested outermost tubular, without perforating or cutting through the wall of the innermost tubular, the wall of the nested intermediate tubular, and the wall of the nested outermost tubular, to form a protrusion of the wall of the innermost tubular that extends into the first annulus between the innermost tubular and the nested intermediate tubular, to form a nested intermediate protrusion of the wall of the nested intermediate tubular that extends into the second annulus between nested intermediate tubular and the nested outermost tubular, and to form a nested outermost protrusion of the wall of the outermost tubular that extends into an annulus adjacent the outer surface of the outer tubular.

In an embodiment, at least one of the first annulus, the second annulus, and the third annulus comprises a sealant comprising leaks, and at least one of the protrusion of the wall of the innermost tubular, the nested intermediate protrusion and the nested outermost protrusion compresses the sealant to seal the leaks. In an embodiment, the sealant is cement.

BRIEF DESCRIPTION OF THE DRAWINGS

Various embodiments are hereafter described in detail and with reference to the drawings wherein like reference characters designate like or similar elements throughout the several figures and views that collectively comprise the drawings.

FIG. 1 is a cross-section of an embodiment of a tool, including a shaped charge assembly, for selectively expanding at least a portion of a wall of a tubular.

FIG. 2A to FIG. 2F illustrate methods of selectively expanding at least a portion of the wall of a tubular using the tool.

FIGS. 2O and 2P illustrate a method of selectively expanding the walls of three nested tubulars.

FIG. 3A and FIG. 3B illustrate graphs showing swell profiles resulting from tests of a pipe and an outer housing.

FIG. 4 is a cross-section of an embodiment of the tool, including a shaped charge assembly.

FIGS. 14-17 illustrate another embodiment of an explosive unit that may be included in a set of several similar units.

FIGS. 26A-26D illustrate a method of reducing an annulus leak in a wellbore, according to an embodiment.

FIGS. 27A-27E illustrate another method of reducing an annulus leak in a wellbore, according to an embodiment.

FIG. 28 is a cross-section of an embodiment of a dual firing end explosive column tool, as assembled for operation, for selectively expanding at least a portion of a wall of a tubular.

FIG. 29 is an enlargement of Detail A in FIG. 28.

FIG. 30 is an enlargement of Detail B in FIG. 28.

FIG. 31 is a cross-section of an embodiment of a dual end firing explosive column tool, as assembled for operation, for selectively expanding at least a portion of a wall of a tubular.

FIG. 32 is an enlargement of Detail A in FIG. 31.

FIG. 33 is an enlargement of Detail B in FIG. 31.

FIGS. 35A-35D illustrate systems for pre-testing an expansion charge on a test tubular according to some embodiments.

FIGS. 37A and 378 illustrate the results of another pre-test on the nested tubulars in an open tank according to an embodiment.

DETAILED DESCRIPTION OF THE INVENTION

Figure 2A:
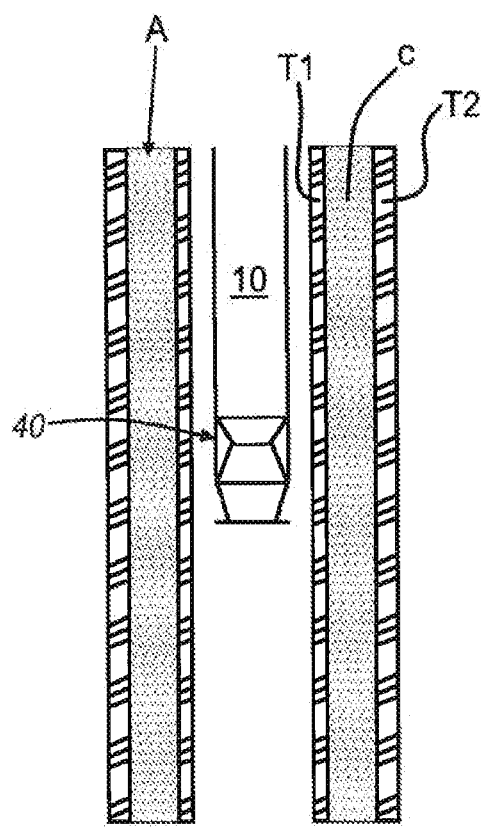

Before explaining the disclosed embodiments in detail, it is to be understood that the present disclosure is not limited to the particular embodiments depicted or described, and that the invention can be practiced or carried out in various ways. The disclosure and description herein are illustrative and explanatory of one or more presently preferred embodiments and variations thereof, and it will be appreciated by those skilled in the art that various changes in the design, organization, means of operation, structures and location, methodology, and use of mechanical equivalents may be made without departing from the spirit of the invention.

As well, it should be understood that the drawings are intended to illustrate and plainly disclose presently preferred embodiments to one of skill in the art, but are not intended to be manufacturing level drawings or renditions of final products and may include simplified conceptual views to facilitate understanding or explanation. Further, the relative size and arrangement of the components may differ from that shown and still operate within the spirit of the invention.

Moreover, as used herein, the terms "up" and "down", "upper" and "lower", "upwardly" and "downwardly", "upstream" and "downstream"; "above" and "below"; and other like terms indicating relative positions above or below a given point or element are used in this description to more clearly describe some embodiments discussed herein. However, when applied to equipment and methods for use in wells that are deviated or horizontal such terms may refer to a left to right, right to left, or other relationship as appropriate. In the specification and appended claims, the terms "pipe", "tube", "tubular", "casing" and/or "other tubular goods" are to be interpreted and defined generically to mean any and all of such elements without limitation of industry usage. Because many varying and different embodiments may be made within the scope of the concept(s) herein taught, and because many modifications may be made in the embodiments described herein, it is to be understood that the details herein are to be interpreted as illustrative and non-limiting.

FIG. 1 shows a tool 10 for selectively expanding at least a portion of a wall of a tubular. The tool 10 comprises a top sub 12 having a threaded internal socket 14 that axially penetrates the "upper" end of the top sub 12. The socket thread 14 provides a secure mechanism for attaching the tool 10 with an appropriate wire line or tubing suspension string (not shown). The tool 10 can have a substantially circular cross-section, and the outer configuration of the tool 10 can be substantially cylindrical. The "lower" end of the top sub 12, as shown, can include a substantially flat end face 15. As shown, the flat end face 15 perimeter of the top sub can be delineated by an assembly thread 16 and an O-ring seal 18. The axial center 13 of the top sub 12 can be bored between the assembly socket thread 14 and the end face 15 to provide a socket 30 for an explosive detonator 31. In some embodiments, the detonator may comprise a bi-directional booster with a detonation cord.

A housing 20 can be secured to the top sub 12 by, for example, an internally threaded housing sleeve 22. The O-ring 18 can seal the interface from fluid invasion of the interior housing volume. A window section 24 of the housing interior is an inside wall portion of the housing 20 that bounds a cavity 25 around the shaped charge between the outer or base perimeters 52 and 54. In an embodiment, the upper and lower limits of the window 24 are coordinated with the shaped charge dimensions to place the window "sills" at the approximate mid-line between the inner and outer surfaces of the explosive material 60. The housing 20 may be a frangible steel material of approximately 55-60 Rockwell "C" hardness.

As shown, below the window 24, the housing 20 can be internally terminated by an integral end wall 32 having a substantially flat internal end-face 33. The external end-face 34 of the end wall may be frusto-conical about a central end boss 36. A hardened steel centralizer assembly 38 can be secured to the end boss by assembly bolts 39a, 39b, wherein each blade of the centralizer assembly 38 is secured with a respective one of the assembly bolts 39a. 39b (i.e., each blade has its own assembly bolt).

A shaped charge assembly 40 can be spaced between the top sub end face 15 and the internal end-face 33 of the housing 20 by a pair of resilient, electrically non-conductive, ring spacers 56 and 58. In some embodiments, the ring spacers may comprise silicone sponge washers. An air space of at least 0.25 centimeters (0.1 inches) is preferred between the top sub end face 15 and the adjacent face of a thrust disc 46. Similarly, a resilient, non-conductive lower ring spacer 58 (or silicone sponge washer) provides an air space that can be at least 0.25 centimeters (0.1 inches) between the internal end-face 33 and an adjacent assembly lower end plate 48.

Loose explosive particles can be ignited by impact or friction in handling, bumping or dropping the assembly. Ignition that is capable of propagating a premature explosion may occur at contact points between a steel, shaped charge thrust disc 46 or end plate 48 and a steel housing 20. To minimize such ignition opportunities, the thrust disc 46 and lower end plate 48 can be fabricated of non-sparking brass. In an embodiment, the thrust disc 46 and lower end plate 48 may be formed of zinc, or a zinc alloy material. For instance, the thrust disc 46 and lower end plate 48 may be formed of zinc powder or powder including zinc. Upon detonation of the explosive material 60, the zinc is consumed by the resulting explosion such that there is very little, if any, debris left over from the thrust disc 46 and lower end plate 48. As a result, there may be less debris in the well that could later obstruct the running of other tools in the well. For the same reasons, i.e., to minimize the amount of debris after detonation of the explosive material 60, the housing 20 may also be formed of zinc, or a zinc alloy material.

Figure 9:
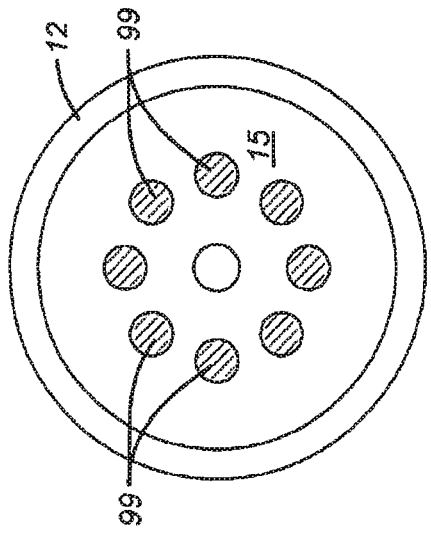
FIG. 9 is a bottom plan view of an embodiment of a top sub after detonation of the explosive material.
Figure 7:
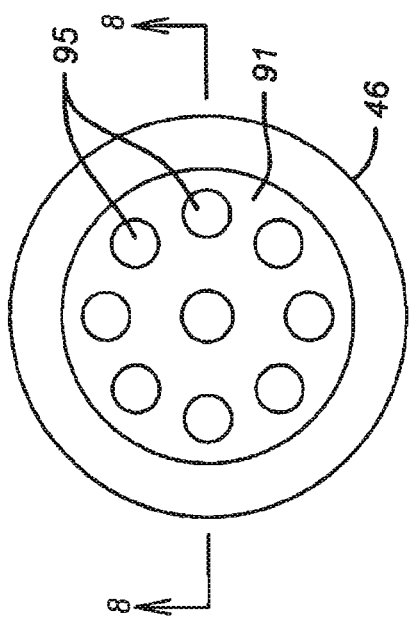
FIG. 7 is a plan view of an embodiment of an end plate showing marker pocket borings.
Figure 8:
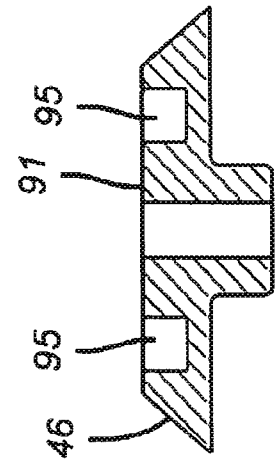
FIG. 8 is a cross-section view of an embodiment of an end plate along plane 8-8 of FIG. 7.

The outer faces 91 and 93 of the end plates 46 (upper thrust disc or back up plates) and 48, as respectively shown by FIG. 1, can be blind bored with marker pockets 95 in a prescribed pattern, such as a circle with uniform arcuate spacing between adjacent pockets as illustrated by FIGS. 7 and 8. The pockets 95 in the outer faces 91, 93 are shallow surface cavities that are stopped short of a complete aperture through the end plates to form selectively weakened areas of the end plates. When the explosive material 60 detonates, the marker pocket walls are converted to jet material. The jet of fluidized end plate material scar the lower end face 15 of the top sub 12 with impression marks 99 in a pattern corresponding to the original pockets as shown by FIG. 9. When the top sub 12 is retrieved after detonation, the uniformity and distribution of these impression marks 99 reveal the quality and uniformity of the detonation and hence, the quality of the explosion. For example, if the top sub face 15 is marked with only a half section of the end plate pocket pattern, it may be reliability concluded that only half of the explosive material 60 correctly detonated.

The explosive material 60 may be formed into explosive units 60. The explosive units 60 traditionally used in the composition of shaped charge tools comprises a precisely measured quantity of powdered, high explosive material, such as RDX, HNS or HMX. The explosive material 60 may be formed into units 60 shaped as a truncated cone by placing the explosive material in a press mold fixture. A precisely measured quantity of powdered explosive material, such as RDX, HNS or HMX, is distributed within the internal cavity of the mold. Using a central core post as a guide mandrel through an axial aperture 47 in the upper thrust disc 46, the thrust disc is placed over the explosive powder and the assembly subjected to a specified compression pressure. This pressed lamination comprises a half section of the shaped charge assembly 40. The explosive units 60 may be symmetric about a longitudinal axis 13 extending through the units 60.

The lower half section of the shaped charge assembly 40 can be formed in the same manner as described above, having a central aperture 62 of about 0.3 centimeters (0.13 inches) diameter in axial alignment with thrust disc aperture 47 and the end plate aperture 49. A complete assembly comprises the contiguous union of the lower and upper half sections along the juncture plane 64. Notably, the thrust disc 46 and end plate 48 are each fabricated around respective annular boss sections 70 and 72 that provide a protective material mass between the respective apertures 47 and 49 and the explosive material 60. These bosses are terminated by distal end faces 71 and 73 within a critical initiation distance of about 0.13 centimeters (0.05 inches) to about 0.25 centimeters (0.1 inches) from the assembly juncture plane 64. The critical initiation distance may be increased or decreased proportionally for other sizes. Hence, the explosive material 60 is insulated from an ignition wave issued by the detonator 31 until the wave arrives in the proximity of the juncture plane 64.

The apertures 47, 49 and 62 for the FIG. 1 embodiment remain open and free of boosters or other explosive materials. Although an original explosive initiation point for the shaped charge assembly 40 only occurs between the boss end faces 71 and 73, the original detonation event is generated by the detonator 31 outside of the thrust disc aperture 47. The detonation wave can be channeled along the empty thrust disc aperture 47 to the empty central aperture 62 in the explosive material. Typically, an explosive load quantity of 38.8 grams (1.4 ounces) of HMX compressed to a loading pressure of 20.7 Mpa (3,000 psi) may require a moderately large detonator 31 of 420 mg (0.02 ounces) HMX for detonation.

The FIG. 1 embodiment obviates any possibility of orientation error in the field while loading the housing 20. A detonation wave may be channeled along either boss aperture 47 or 49 to the explosive material 60 around the central aperture 62. Regardless of which orientation the shaped charge assembly 40 is given when inserted in the housing 20, the detonator 31 will initiate the explosive material 60.

In this embodiment, absent from the explosive material units 60 is a liner that is conventionally provided on the exterior surface of the explosive material and used to cut through the wall of a tubular. Instead, the exterior surface of the explosive material is exposed to the inner surface of the housing 20. Specifically, the housing 20 comprises an outer surface 53 facing away from the housing 20, and an opposing inner surface 51 facing an interior of the housing 20. The explosive units 60 each comprise an exterior surface 50 that faces and is exposed to the inner surface 51 of the housing 20. Describing that the exterior surface 50 of the explosive units 60 is exposed to the inner surface 51 of the housing 20 is meant to indicate that the exterior surface 50 of the explosive units 60 is not provided with a liner, as is the case in conventional cutting devices. The explosive units 60 can comprise a predetermined amount of explosive material sufficient to expand at least a portion of the wall of the tubular into a protrusion extending outward into an annulus adjacent the wall of the tubular. For instance, testing conducted with a 72 grams (2.54 ounces) HMX, 6.8 centimeter (2.7 inches) outer diameter expansion charge on a tubular having a 11.4 centimeter (4.5 inch) outer diameter and a 10.1 centimeter (3.98 inch) inner diameter resulted in expanding the outer diameter of the tubular to 13.5 centimeters (5.32 inches). The expansion was limited to a 10.2 centimeter (4 inch) length along the outer diameter of the tubular. It is important to note that the expansion is a controlled outward expansion of the wall of the tubular, and does not cause puncturing, breaching, penetrating or severing of the wall of the tubular. The annulus may be formed between an outer surface of the wall of the tubular being expanded and an inner wall of an adjacent tubular or a formation. Cement located in the annulus is compressed by the protrusion, reducing the porosity of the cement by reducing the number of micro annulus pores in the cement or other sealing agents. The reduced-porosity cement provides a seal against moisture seepage that would otherwise lead to cracks, decay and/or contamination of the cement, casing and wellbore. The compressed cement may also collapse and/or compress open channels in a cemented annulus, and/or may compress the cemented annulus to cure other defects or inconsistencies in the cement (such as due to inconsistent viscosity of the cement, and/or a pressure differential in the formation).

A method of selectively expanding at least a portion of the wall of a tubular using the tool 10 described herein may be as follows. The tool 10 is assembled including the housing 20 containing explosive material 60 adjacent two end plates 46, 48 on opposite sides of the explosive material 60. As discussed in the embodiment above, the housing 20 comprises an inner surface 51 facing an interior of the housing 20, and the explosive material 60 comprises an exterior surface 50 that faces the inner surface 51 of the housing 20 and is exposed to the inner surface 51 of the housing 20 (i.e., there is no liner on the exterior surface 50 of the explosive material 60).

Figure 2B:
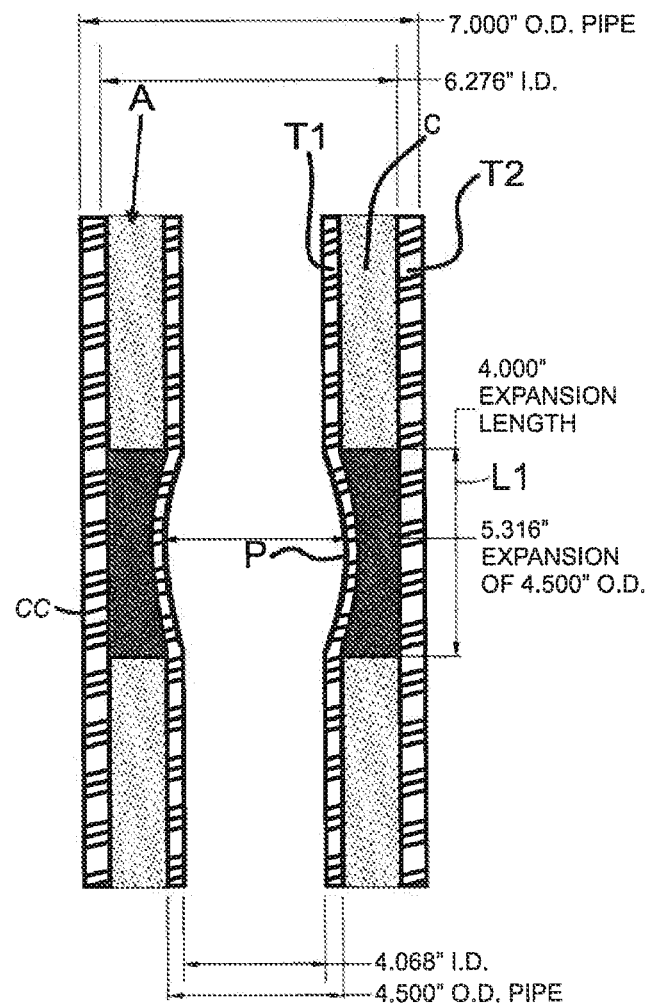

A detonator 31 (see FIG. 1) can be positioned adjacent to one of the two end plates 46, 48. The tool 10 can then be positioned within an inner tubular T1 that is to be expanded, as shown in FIG. 2A. The inner tubular T1 may be within an outer tubular T2, such that an annulus "A" exists between the outer diameter of the inner tubular T1 and the inner diameter of the outer tubular T2. A sealant, such as cement "C" may be provided in the annulus "A". When the tool 10 reaches the desired location in the inner tubular T1, the detonator 31 is actuated to ignite the explosive material 60, causing a shock wave that travels radially outward to impact the inner tubular T1 at a first location and expand at least a portion of the wall of the inner tubular T1 radially outward without perforating or cutting through the portion of the wall, to form a protrusion "P" of the inner tubular T1 at the portion of the wall as shown in FIG. 2B. The protrusion "P" extends into the annulus "A". The protrusion "P" compresses the cement "C" to reduce the porosity of the cement by reducing the number of micro pores. The compressed cement is shown in FIG. 2B with the label "CC". The reduced number of micro pores in the compressed cement "CC" reduces the risk of seepage into the cement. Further, the protrusion "P" creates a ledge or barrier that helps seal that portion of the wellbore from seepage of outside materials. Note that the pipe dimensions shown in FIGS. 2A to 2F are exemplary and for context, and are not limiting to the scope of the invention.

Figure 3B:
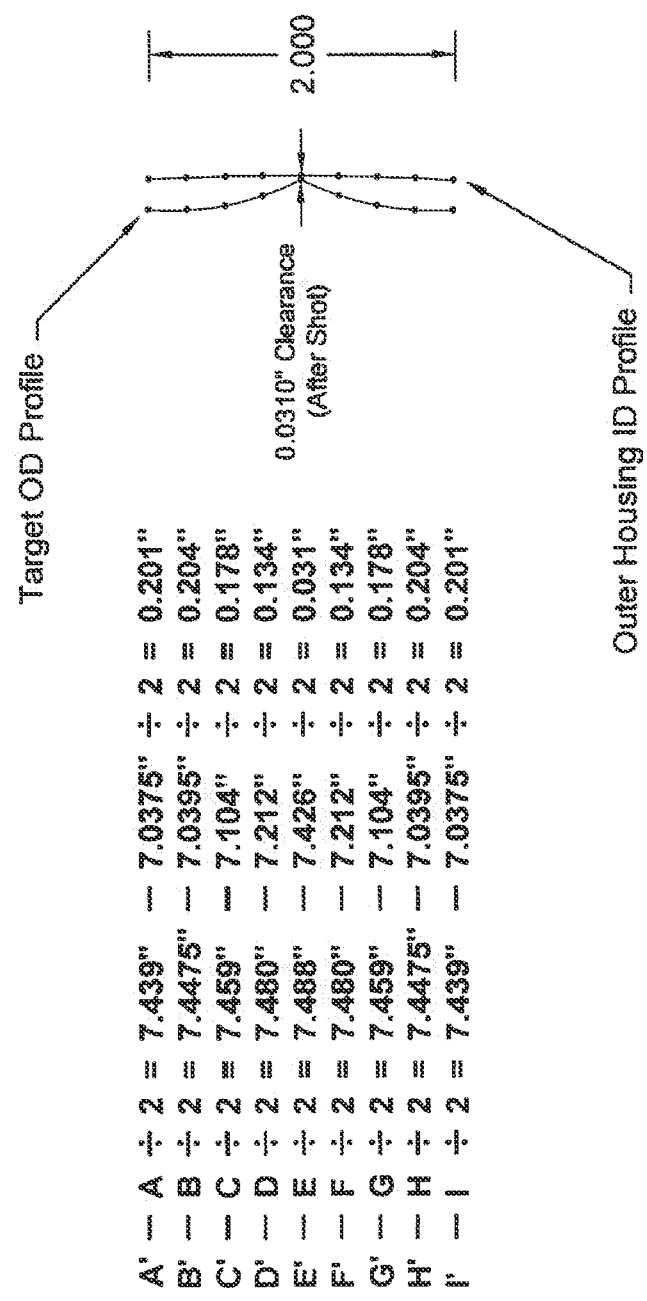

The protrusion "P" may impact the inner wall of the outer tubular T2 after detonation of the explosive material 60. In some embodiments, the protrusion "P" may maintain contact with the inner wall of the outer tubular T2 after expansion is complete. In other embodiments, there may be a small space between the protrusion "P" and the inner wall of the outer tubular T2. For instance, the embodiment of FIG. 3B shows that the space between the protrusion "P" and the inner wall of the outer tubular T2 may be 0.07874 centimeters (0.0310 inches). However, the size of the space will vary depending on several factors, including, but not limited to, the size (e.g., thickness), strength and material of the inner tubular T1, the type and amount of the explosive material in the explosive units 60, the physical profile of the exterior surface 50 of the explosive units 60, the hydrostatic pressure bearing on the inner tubular T1, the desired size of the protrusion, and the nature of the wellbore operation. The small space between the protrusion "P" and the inner wall of the other tubular T2 may still be effective for blocking flow of cement, barite, other sealing materials, drilling mud, etc., so long as the protrusion "P" approaches the inner diameter of the outer tubular T2. This is because the viscosity of those materials generally prevents seepage through such a small space. That is, the protrusion "P" may form a choke that captures (restricts flow of) the cement long enough for the cement to set and form a seal. Expansion of the inner tubular T1 at the protrusion "P" causes that portion of the wall of the inner tubular T1 to be work-hardened, resulting in greater yield strength of the wall at the protrusion "P". The portion of the wall having the protrusion "P" is not weakened. In particular, the yield strength of the inner tubular T1 increases at the protrusion "P", while the tensile strength of the inner tubular T1 at the protrusion "P" decreases only nominally. Expansion of the inner tubular T1 at the protrusion "P" thus strengthens the tubular without breaching the inner tubular T1.

Figure 23:
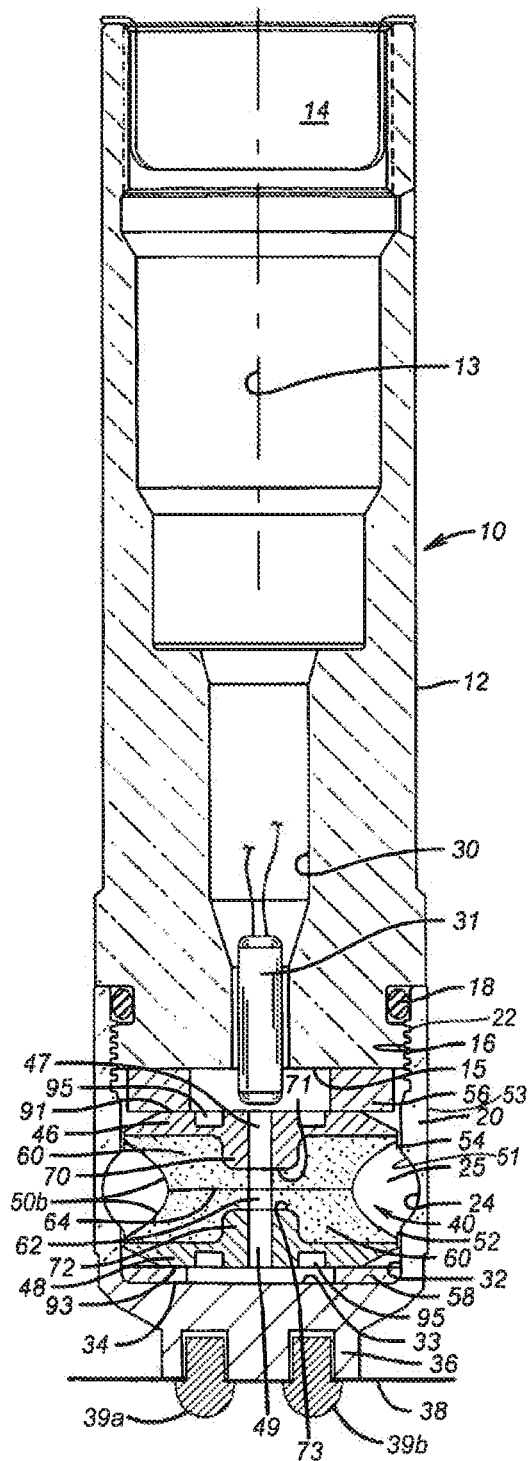
FIG. 23 is a cross-section of another embodiment of a tool, including a shaped charge assembly, for selectively expanding at least a portion of a wall of a tubular.

The magnitude of the protrusion in the embodiment discussed above depends on several factors, including the amount of explosive material in the explosive units 60, the type of explosive material, the physical profile of the exterior surface 50 of the explosive units 60, the strength of the inner tubular T1, the thickness of the tubular wall, the hydrostatic pressure bearing on the inner tubular T1, and the clearance adjacent the tubular being expanded, i.e., the width of the annulus "A" adjacent the tubular that is to be expanded. In the embodiment if FIG. 1, the physical profile of the exterior surface 50 of the explosive units 60 is shaped as a sideways "V". The angle at which the legs of the "V" shape intersect each other may be varied to adjust the size and/or shape of the protrusion. Generally, a smaller angle will generate a larger protrusion "P". Alternatively, the physical profile of the exterior surface 50 may be curved to define a generally hemispherical shape, such as shown in the example of FIG. 23. In that embodiment, the exterior surface 50b of the explosive units 60 is shaped with a curve or curves, instead of the sideways "V" shape having an intersection at the convergence of two linear lines as shown in FIGS. 1, 2G, 2H, 2I, 4-6, 24 and 25. As used herein, the phrase "generally hemispherical shape" means that the exterior surface 50 of the explosive units 60 may have a perfect hemispherical shape, a flattened hemispherical shape, an oblong hemispherical shape, or a shape formed only of curves or curved lines. In some embodiments, the "generally hemispherical shape" may also mean that the exterior surface 50 of the explosive units 60 may be composed of a series of three or more linear lines that together form a concave shape towards the cavity 25 around the shaped charge. In further embodiments, the "generally hemispherical shape" may include a sideways "U" shape. Generally speaking, the "generally hemispherical shape" of the explosive units 60 results in such explosive units 60 producing, upon ignition, a jet that is not as focused as the "V" shape explosive units 60. Accordingly, even when the explosive units 60 having the generally hemispherical exterior surface 50b include a liner, according to one embodiment herein, the shape of the exterior surface 50b may controlled so that the collapsed liner forms a jet that is not focused enough to penetrate the inner tubular T1. That is, the generally hemispherical exterior surface 50b may be shaped, upon ignition of the explosive units 60, to form the protrusion "P" discussed herein without puncturing the inner tubular T1.

The method of selectively expanding at least a portion of the wall of a tubular T1 using the shaped charge tool 10 described herein may be modified to include determining the following characteristics of the tubular T1: a material of the tubular T1, a thickness of a wall of the tubular T1; an inner diameter of the tubular T1, an outer diameter of the tubular T1, a hydrostatic pressure bearing on the tubular T1, and a size of a protrusion "P" to be formed in the wall of the tubular T1. Next, the explosive force necessary to expand, without puncturing, the wall of the tubular T1 to form the protrusion "P", is calculated, or determined via testing, based on the above determined material characteristics. As discussed above, the determinations and calculation of the explosive force can be performed via a software program executed on a computer. Physical hydrostatic testing of the explosive expansion charges yields data which may be input to develop computer models. The computer implements a central processing unit (CPU) to execute steps of the program. The program may be recorded on a computer-readable recording medium, such as a CD-ROM, or temporary storage device that is removably attached to the computer. Alternatively, the software program may be downloaded from a remote server and stored internally on a memory device inside the computer. Based on the necessary force, a requisite amount of explosive material for the one or more explosive material units 60 to be added to the shaped charge tool 10 is determined. The requisite amount of explosive material can be determined via the software program discussed above.

The one or more explosive material units 60, having the requisite amount of explosive material, is then added to the shaped charge tool 10. The loaded shaped charge tool 10 is then positioned within the tubular T1 at a desired location. Next, the shaped charge tool 10 is actuated to detonate the one or more explosive material units 60, resulting in a shock wave, as discussed above, that expands the wall of the tubular T1 radially outward, without perforating or cutting through the wall, to form the protrusion "P". The protrusion "P" extends into the annulus "A" adjacent an outer surface of the wall of the tubular T1.

A first series of tests was conducted to compare the effects of sample explosive units 60, which did not have a liner, with a comparative explosive unit that included a conventional liner on the exterior surface thereof. The explosive units in the first series had 15.88 centimeter (6.25 inch) outer housing diameter, and were each tested separately in a respective 17.8 centimeter (7 inch) outer diameter test pipe. The test pipe had a 16 centimeter (6.3 inch) inner diameter, and a 0.89 centimeter (0.35 inch) Wall Thickness, L-80.

The comparative sample explosive unit had a 15.88 centimeter (6.25 inch) outside housing diameter and included liners. Silicone caulk was added to foul the liners, leaving only the outer 0.76 centimeters (0.3 inches) of the liners exposed for potential jetting. 77.6 grams (2.7 ounces) of HMX main explosive was used as the explosive material. The sample "A" explosive unit had a 15.88 centimeter (6.25 inch) outside housing diameter and was free of any liners. 155.6 grams (5.5 ounces) of HMX main explosive was used as the explosive material. The sample "B" explosive unit had a 15.88 centimeter (6.25 inch) outside housing diameter and was free of any liners. 122.0 grams (4.3 ounces) of HMX main explosive was used as the explosive material.

The test was conducted at ambient temperature with the following conditions. Pressure: 20.7 Mpa (3,000 psi). Fluid: water. Centralized Shooting Clearance: 0.06 centimeters (0.03 inches). The Results are provided below in Table 1.

TABLE 1

Test Summary in 17.8 centimeters (7 inch)
O.D. × 0.89 centimeters (0.350 inch) wall L-80

| Sample | Main Load HMX (grams) (ounces) | Swell (centimeters) (inches) |
|---|---|---|
| Comparative (with liner) | 77.6 g (2.7 oz) | 18.5 cm (7.284 inches) |
| A | 155.6 g (5.5 oz) | 19.3 cm (7.600 inches) |
| B | 122.0 g (4.3 oz) | 18.6 cm (7.317 inches) |

The comparative sample explosive unit produced an 18.5 centimeter (7.28 inch) swell, but the jetting caused by the explosive material and liners undesirably penetrated the inside diameter of the test pipe. Samples "A" and "B" resulted in 19.3 centimeter (7.6 inch) and 18.6 centimeter (7.32 inch) swells (protrusions), respectively, that were smooth and uniform around the inner diameter of the test pipe.

A second test was performed using the Sample "A" explosive unit in a test pipe having similar properties as in the first series of tests, but this time with an outer housing outside the test pipe to see how the character of the swell in the test pipe might change and whether a seal could be effected between the test pipe and the outer housing. The test pipe had a 17.8 centimeter (7 inch) outer diameter, a 16.1 centimeter (6.32 inch) inner diameter, a 0.86 centimeter (0.34 inch) wall thickness, and a 813.6 Mpa (118 KSI) tensile strength. The outer housing had an 21.6 centimeter (8.5 inch) outer diameter, a 18.9 centimeter (7.4 inch) inner diameter, a 1.35 centimeter (0.53 inch) wall thickness, and a 723.95 Mpa (105 KSI) tensile strength.

The second test was conducted at ambient temperature with the following conditions. Pressure: 20.7 Mpa (3,000 psi). Fluid: water. Centralized Shooting Clearance: 0.09 centimeters (0.04 inches). Clearance between the 17.8 centimeter (7 inch) outer diameter of the test pipe and the inner diameter of the housing: 0.55 centimeters (0.22 inches). After the sample "A" explosive unit was detonated, the swell on the 17.8 centimeter (7 inch) test pipe measured at 18.9 centimeters (7.441 inches)×18.89 centimeters (7.44 inches), indicating that the inner diameter of the outer housing (18.88 centimeters (7.433 inches)) somewhat retarded the swell (19.3 centimeters (7.6 inches)) observed in the first test series involving sample "A". There was thus a "bounce back" of the swell caused by the inner diameter of the outer housing. In addition, the inner diameter of outer housing increased from 18.88 centimeters (7.433 inches) to 18.98 centimeters (7.474 inches). The clearance between the outer diameter of the test pipe and the inner diameter of the outer housing was reduced from 0.55 centimeters (0.22 inches) to 0.08 centimeters (0.03 inches). FIG. 3A shows a graph 400 illustrating the swell profiles of the test pipe and the outer housing. FIG. 3B is a graph 401 illustrating an overlay of the swell profiles showing the 0.08 centimeter (0.03 inch) resulting clearance.

A second series of tests was performed to compare the performance of a shaped charge tool 10 (with liner-less explosive units 60) having different explosive unit load weights. In the second series of tests, the goal was to maximize the expansion of a 17.8 centimeter (7 inch) outer diameter pipe having a wall thickness of 1.37 centimeters (0.54 inches), to facilitate operations on a Shell North Sea Puffin well. Table 2 shows the results of the tests.

TABLE 2

| Test | Explosive Weight | Explosive Unit Load Weight/1" | Centralized Shooting Clearance | Max Swell of 7" O.D. Pipe |
|---|---|---|---|---|
| 1 | 175 g HMX (6.17 oz.) | 125 g (4.4 oz.) | 0.26 cm (0.103 inches) | 18.8 cm (7.38 inches) |
| 2 | 217 g HMX (7.65 oz.) | 145 g (5.11 oz.) | 0.26 cm (0.103 inches) | 19.04 cm (7.49 inches) |
| 3 | 350 g HMX (12.35 oz.) | 204 g (7.2 oz.) | 0.26 cm (0.103 inches) | 20.2 cm (7.95 inches) |

Tests #1 to #3 used the shaped charge tool 10 having liner-less explosive units 60 with progressively increasing explosive weights. In those tests, the resulting swell of the 17.8 centimeter (7 inch) outer diameter pipe continued to increase as the explosive weight increased. However, in test #3, which utilized 350 grams (12.35 ounces) HMX resulting in a 204 gram (7.2 ounces) unit loading, the focused energy of the expansion charged breached the 17.8 centimeter (7 inch) outer diameter pipe. Thus, to maximize the expansion of this pipe without breaching the pipe would require the amount of explosive energy in test #3 to be delivered with less focus.

Returning to the method discussed above, the relatively short expansion length (e.g., 10.2 centimeters (4 inches)) may advantageously seal off micro annulus leaks or cure the other cement defects discussed herein. It may be the case that the cement density between the outer diameter of the inner tubular T1 and the inner diameter of the outer tubular T2 was inadequate to begin with, such that a barrier may not be formed and/or the cement "C" present between the inner tubular T1 and the outer tubular T2 may simply be forced above and below the expanded protrusion "P" (see, e.g., FIG. 2C). While there may still be a semi compression "SC" of the cement and reduction in porosity, it might not be adequate to slow a micro annulus leak in a manner that would conform to industry and/or regulatory standards. In such a case, instead of detonating just one explosive unit 60, multiple explosive units 60 may be detonated, sequentially and in close proximity to each other, or simultaneously and in close proximity to each other. For example, if two explosive units 60 were detonated sequentially or simultaneously, 10.16 centimeters (4.0 inches) apart in a zone where there is an inadequate cement job, the compression effect of the cement from the first explosive unit 60 being forced down, and from the second explosive unit 60 being forced up, may result in an adequate barrier "CB", as shown in FIG. 2D, that conforms to industry and/or regulatory standards. An example of a shaped charge tool 10 comprising a top sub 12 and having two explosive units 60 positioned, e.g., 10.16 centimeters (4.0 inches), apart from each other is shown in FIG. 2G.

Figure 2E:
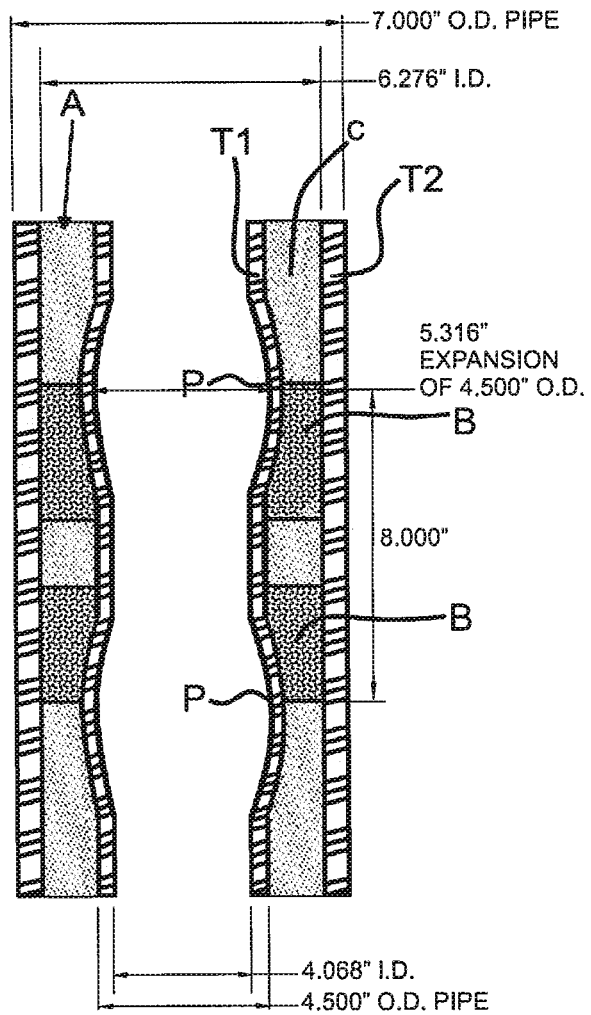
Figure 2F:
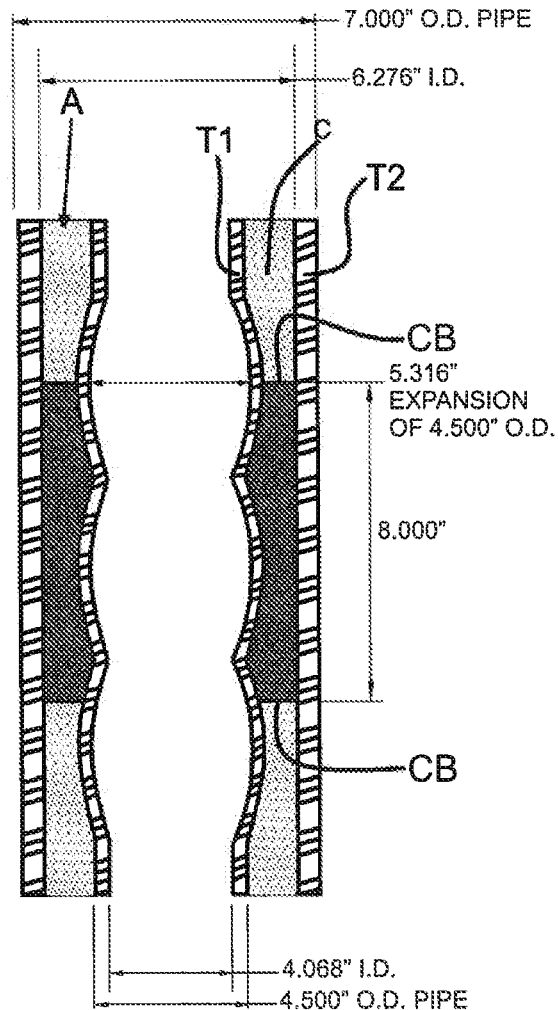

Furthermore, three explosive units 60 may be detonated as follows. To begin with, first and second explosive units 60 may be detonated 20.3 centimeters (8 inches) apart from each other to create two spaced apart protrusions "P." as shown in FIG. 2E. The two detonations form two barriers "B" shown in FIG. 2E, with the first explosive unit 60 forcing the cement "C" downward and the second explosive unit 60 forcing cement "C" upward. A third explosive unit 60 is then detonated between the first and second explosive units 60. Detonation of the third explosive unit 60 further compresses the cement "C" that was forced downward by the first explosive unit 60 and the cement "C" that was forced upward by the second explosive unit 60, to form two adequate barriers "CB" as shown in FIG. 2F. Alternatively, detonation of the third explosive unit 60 may result on one barrier above or below the third explosive unit 60 depending on the cement competence in the respective zones. Either scenario (one or two barriers) may further restrict/seal off micro annulus leaks, or cure the other cement defects discussed herein, to conform with industry and/or regulatory standards. An example of a shaped charge tool 10 comprising a top sub 12 and having three explosive units 60 positioned, e.g., 10.16 centimeters (4.0 inches), apart from each other is shown in FIG. 2H.

Figure 2G:
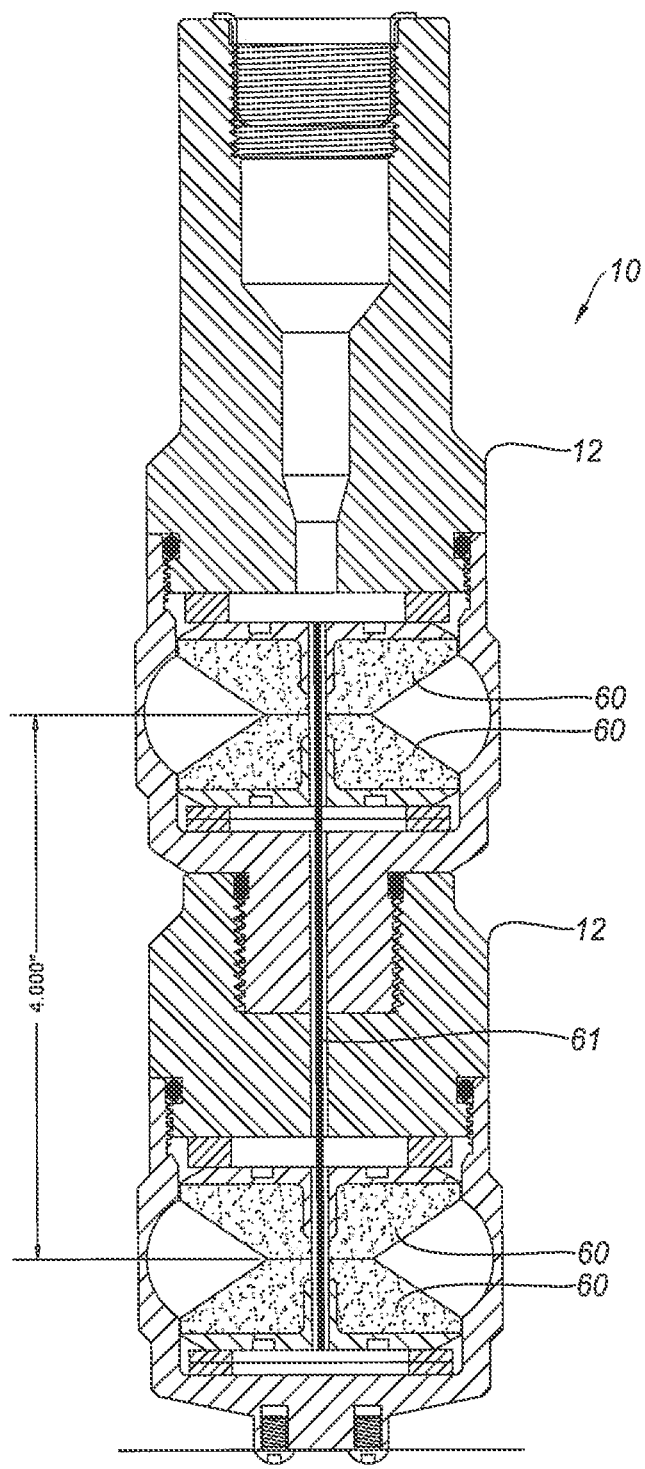
FIG. 2G to FIG. 2I illustrate embodiments of a tool that may be used in some of the methods illustrated in FIG. 2A to FIG. 2F.
Figure 2H:
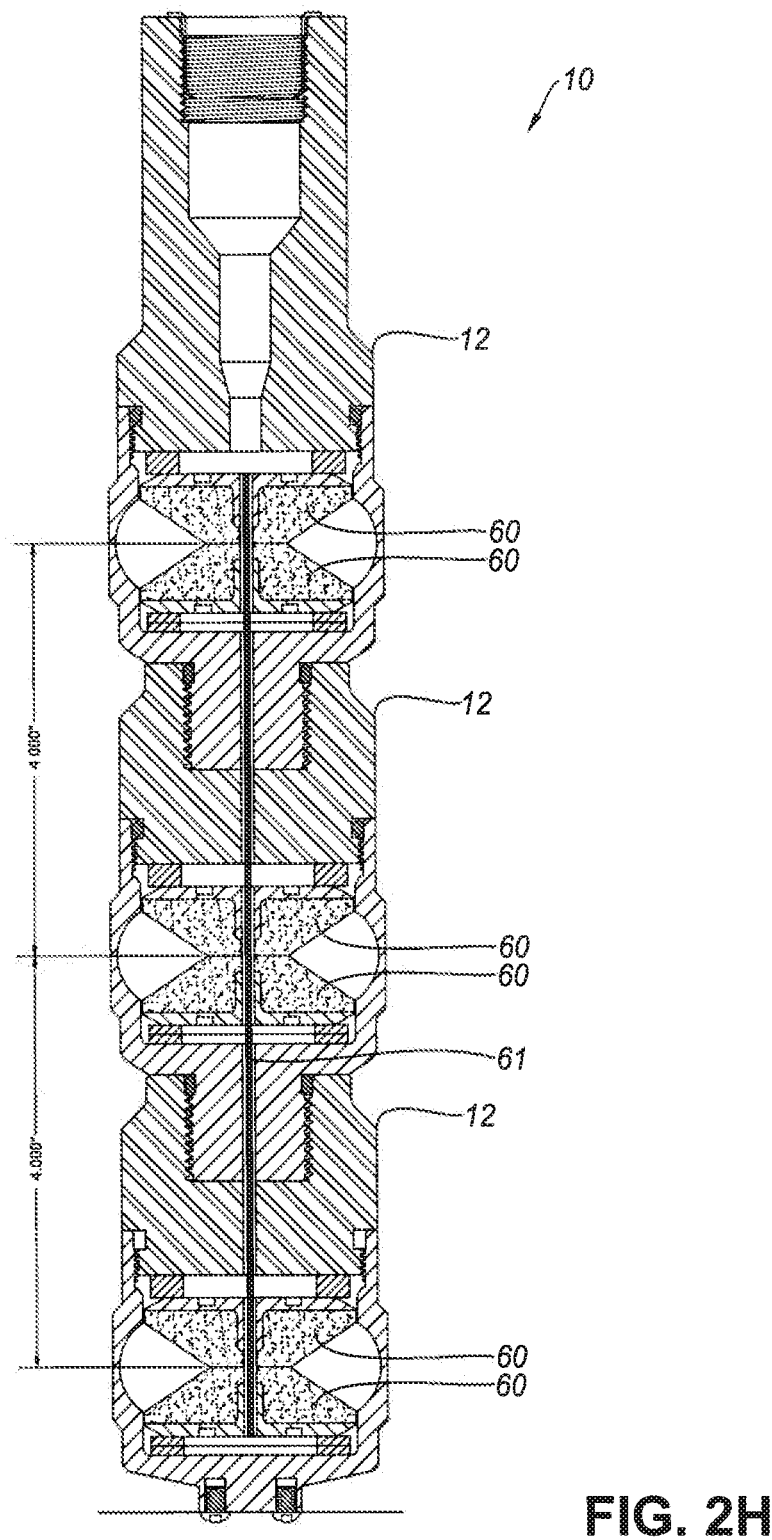
Figure 2I:
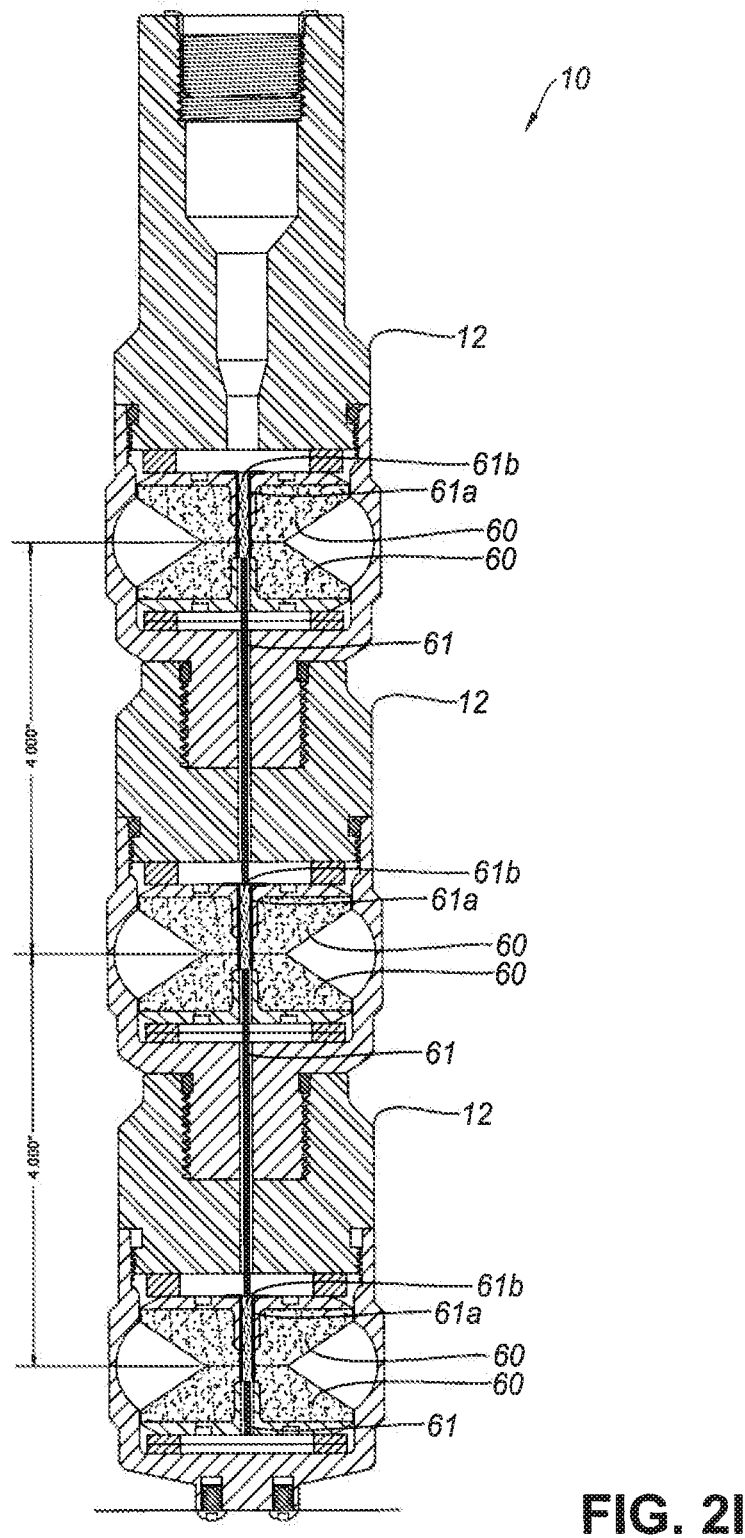

FIGS. 2G and 2H illustrate an embodiment in which a detonation cord 61 for initiating the tool is run through the length of the tool 10. Another way to configure the detonation cord 61 is to install separate sections of detonation cords 61 between boosters 61a, as shown in FIG. 2I. Each booster 61a can be filled with explosive material 61b, such as HMX. That is, a first booster 61a, provided with a first explosive unit 60, may be associated with a first section of detonation cord 61, which first section of detonation cord 61 connects to a second booster 61a located further down the tool 10 and provided with a second explosive unit 60. A second section of detonation cord 61 is provided between the second booster 61a and a third booster 61a, as shown in FIG. 2I. If further explosive units 60 are provided, the sequence of a section of detonation cord 61 between consecutive boosters 61a may be continued.

The contingencies discussed with respect to FIGS. 2C through 2F may address the situation in which, even when cement bond logs suggest a cement column is competent in a particular zone, there may still be a variation in the cement volume and density in that zone requirement is more than one expansion charge.

In the methods discussed above, expansion of the inner tubular T1 causes the sealant displaced by the expansion to compress, reducing the number of micro pores in the cement or the number of other cement defects discussed herein. The expansion may occur after the sealant is pumped into the annulus "A". Alternatively, the cement or other sealant may be provided in the annulus "A" on the portion of the wall of the inner tubular T1, after the portion of the wall is expanded. The methods may include selectively expanding the inner tubular T1 at a second location spaced from the first location to create a pocket between the first and second locations. The sealant may be provided in the annulus "A" before the pocket is formed. In an alternative embodiment, expansion at the first location may occur before the sealant is provided, and expansion at the second location may occur after the sealant is provided.

Figure 2J:
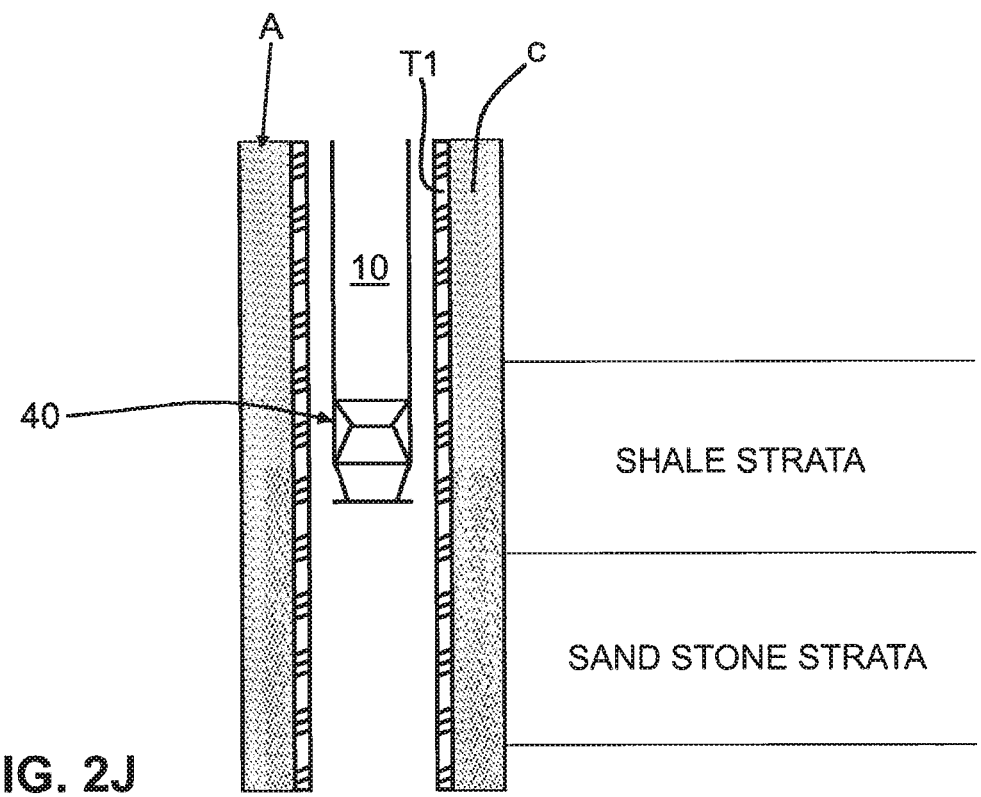
FIGS. 2J to 2L illustrate methods of selectively expanding at least a portion of the wall of a tubular surround by formation.
Figure 2K:
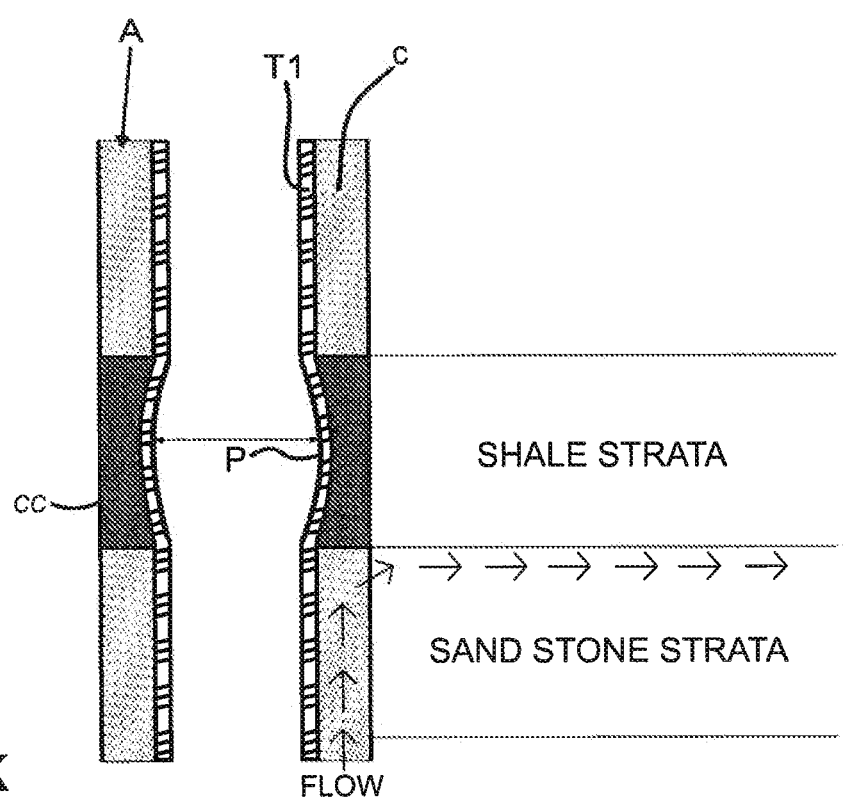
Figure 2L:
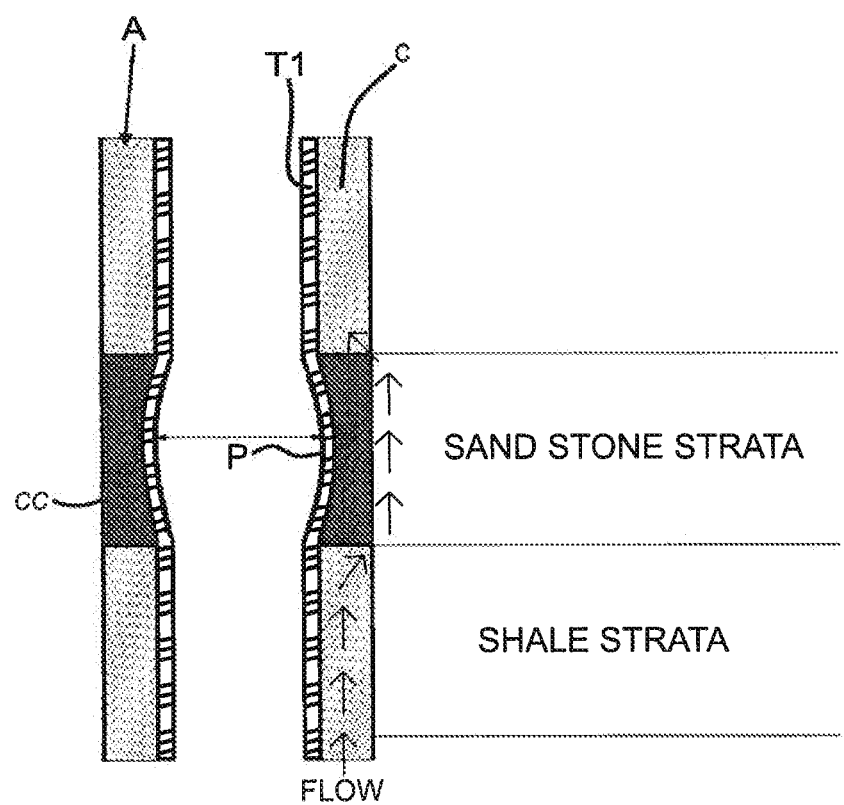

FIGS. 2J to 2L illustrate methods of selectively expanding at least a portion of the wall of a tubular surround by formation (earth). FIG. 2J shows that the tool 10 is positioned within the tubular T1 that is cemented into a formation that includes shale strata and sandstone strata. The cement "C" abuts the outer surface of the tubular T1 on one side, and abuts the strata on the opposite side, as shown in FIG. 23. Shale is one of the more non-permeable earthen materials, and may be referred to as a cap rock formation. To the contrary, sandstone is known to be permeable. Accordingly, when the tool 10 is used to in a tubular/earth application to consolidate cement adjacent a formation, such as shown in FIG. 2J, it is preferable to expand the wall of the tubular T1 that is adjacent the cap rock formation (e.g., shale strata) because the non-permeable cap rock formation seals off the annulus flow, as shown in FIG. 2K. On the other hand, if the tool 10 was used to expand the wall of the tubular T1 that was adjacent the sandstone strata, as shown in FIG. 2L, even if the cement "C" is consolidated to seal against annulus flow through the consolidated cement "C", annulus flow can bypass the consolidated cement "C" and migrate or flow through the permeable sandstone strata (see FIG. 2L), defeating the objective of expanding a wall of the tubular T1.

Figure 2N:
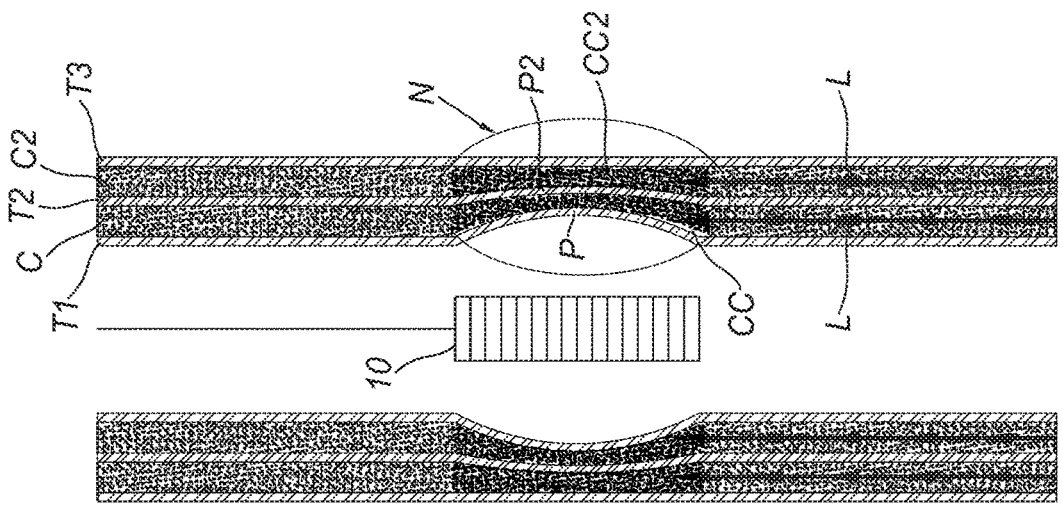
FIGS. 2M and 2N illustrate a method of selectively expanding the walls of two nested tubulars.
Figure 2M:
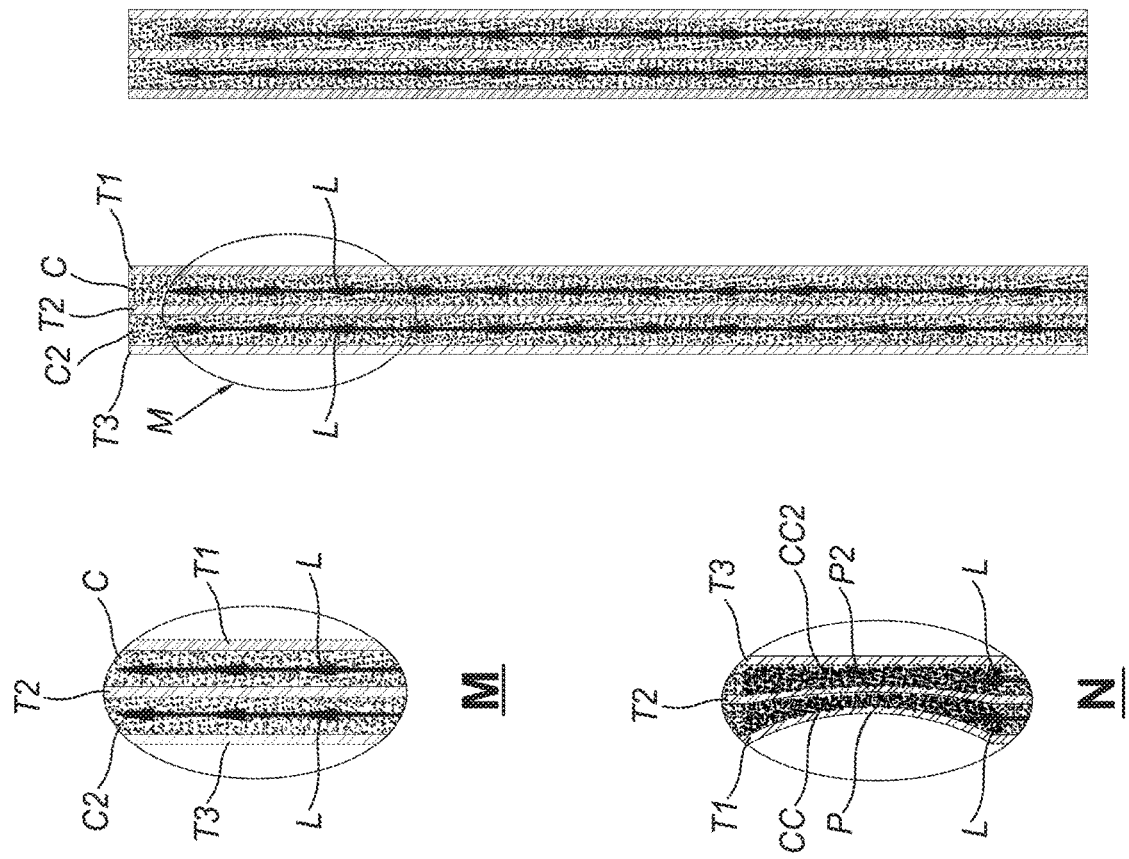

FIGS. 2M and 2N illustrate a method of selectively expanding the walls of two nested tubulars T1 and T2 according to an embodiment. "Nested" is used herein to mean that at least a portion of one tubular is inside of at least a portion of another tubular. In some cases, such "nested" tubulars may be concentric, i.e., having the same axial center. In other cases, the "nested" tubulars may be substantially concentric, but not share the same axial center. The "nested" embodiments discussed herein encompass both perfectly concentric tubulars, substantially concentric tubulars, and non-concentric tubulars in which the outer surface of the inner tubular may be very close to or contact the inner surface of the nested outer tubular. In the nested embodiment of FIG. 2M, inner tubular T1 is surrounded by an outer tubular T2, and an annulus between the inner tubular T1 and the outer tubular T2 that includes a sealant, such as cement "C". A third tubular T3, or formation, surrounds the outer tubular 12. The annulus between the outer tubular T2 and the third tubular T3 or formation also includes a sealant, such as cement "C2". In the embodiment, annulus flow "L" may be present through in the cement "C" and "C2" in both annuli. A tool, such as a shaped charge tool or a dual end fired explosive column tool discussed herein, may be positioned within the inner tubular T1 (see FIG. 2N) to selectively expand the walls of both tubulars T1 and T2 with a single actuation of the tool. That is, detonation of the explosive material in the tool creates a force that travels radially outward to impact the inner tubular T1 and expand at least a portion of the wall of the inner tubular T1 radially outward without perforating or cutting through the portion of the wall, to form a protrusion "P" of the inner tubular T1 as shown in FIG. 2N. The tool may contain an amount of explosive material based at least in part on a hydrostatic pressure bearing on one or more of the inner tubular T1, the outer tubular T2, and the tool itself. The protrusion "P" extends into the annulus between the inner tubular T1 and the outer tubular T2 to compresses the cement "C" to reduce the porosity of the cement "C" by reducing the number of pores, channels, or other cement imperfections allowing annulus leaks. The compressed cement is shown in FIG. 2N with the label "CC". Additionally, the radially traveling force of the detonated explosive material, and/or expansion of the protrusion "P", impacts the outer tubular T2 and expands at least a portion of the wall of the outer tubular T2 radially outward without perforating or cutting through the portion of the wall, to form a protrusion "P2" of the outer tubular 12, as shown in FIG. 2N. The protrusion "P2" extends into the annulus between the outer tubular T2 and the third tubular T3, or formation, to compresses the cement "CC2" in that annulus. The compression reduces the porosity of the cement "CC2" by reducing the number of pores, channels, or other cement imperfections allowing annulus leaks. Thus, compressed cement "CC", "CC2" is consolidated in both annuli with one detonation of the explosive material contained in the tool. In the embodiment of FIG. 2N, a single charge is used to form the protrusions "P". "P2". However, multiple charges serially oriented in the tool could also be used to form multiple sets of the nested protrusions "P", "P2" along the axis of the wellbore.

The reduced number of pores, channels, or other cement imperfections allowing annulus leaks in the compressed cement "CC", "CC2" reduces the risk of seepage into the cement and helps seal against annulus flow through the consolidated cement. Further, the protrusions "P", "P2" may create a ledge or barrier that helps seal that portion of the wellbore from seepage of outside materials. The size and shape of the protrusions "P", "P2" may vary depending on several factors, including, but not limited to, the size (e.g., thickness), strength and material of the inner and outer tubulars T1, T2, the type and amount of the explosive material, the hydrostatic pressure bearing on the inner and outer tubulars T1, T2, the desired size of the protrusions "P", "P2", and the nature of the wellbore operation.

FIGS. 2O and 2P illustrate a method of selectively expanding the walls of three nested tubulars T1, T2 and T3 according to an embodiment. FIG. 2O shows an innermost tubular T1 surrounded by an intermediate tubular T2, and an annulus between the innermost tubular T1 and the intermediate tubular T2 that includes a sealant, such as cement "C". A third tubular T3 surrounds the intermediate tubular T2. The annulus between the intermediate tubular T2 and the third tubular T3 also includes a sealant, such as cement "C2". In addition, another tubular "AP" or formation "F" surrounds the third tubular T3. The annulus between the third tubular T3 and the other tubular "AP" or formation "F" also includes a sealant, such as cement "C3". In the embodiment, annulus flow "L" may be present through in the cement "C", "C2" and "C3" in each annuli. A tool, such as a shaped charge tool or a dual end fired explosive column tool discussed herein, may be positioned within the innermost tubular T1 (see FIG. 2P) to selectively expand the walls of all three tubulars T1, T2 and T3 with a single actuation of the tool. That is, detonation of the explosive material in the tool creates a force that travels radially outward to impact the innermost tubular T1 and expand at least a portion of the wall of the innermost tubular T1 radially outward without perforating or cutting through the portion of the wall, to form a protrusion "P" of the innermost tubular T1 as shown in FIG. 2P. The tool may contain an amount of explosive material based at least in part on a hydrostatic pressure bearing on one or more of the innermost tubular T1, the intermediate tubular T2, the third tubular T3, and the tool itself. The protrusion "P" extends into the annulus between the innermost tubular T1 and the intermediate tubular T2 to compresses the cement "C" to reduce the porosity of the cement "C" by reducing the number of pores, channels, or other cement imperfections allowing annulus leaks. The compressed cement is shown in FIG. 2P with the label "CC". Additionally, the radially traveling force of the detonated explosive material, and/or expansion of the protrusion "P", impacts the intermediate tubular T2 and expands at least a portion of the wall of the intermediate tubular T2 radially outward without perforating or cutting through the portion of the wall, to form a protrusion "P2" of the intermediate tubular T2, as shown in FIG. 2P. The protrusion "P2" extends into the annulus between the intermediate tubular 12 and the third tubular T3 to compresses the cement "CC2" in that annulus. The compression reduces the porosity of the cement "CC2" by reducing the number of pores, channels, or other cement imperfections allowing annulus leaks. Further, the radially traveling force of the detonated explosive material, and/or expansion of the protrusions "P" and "P2", impacts the third tubular T3 and expands at least a portion of the wall of the third tubular T3 radially outward without perforating or cutting through the portion of the wall, to form a protrusion "P3" of the third tubular T3, as shown in FIG. 2P. The protrusion "P3" extends into the annulus between the third tubular T3 and the other tubular "AP" or formation "F" to compresses the cement "CC3" in that annulus. The compression reduces the porosity of the cement "CC3" by reducing the number of pores, channels, or other cement imperfections allowing annulus leaks. Thus, compressed cement "CC", "CC2" and "CC3" is consolidated in the three annuli with one single detonation of the explosive material contained in the tool, or via one single actuation of the tool. In the embodiment of FIG. 2P, a single charge is used to form the protrusions "P", "P2" and "P3". However, multiple charges serially oriented in the tool could also be used to form multiple sets of the nested protrusions "P", "P2" and "P3" along the axis of the wellbore. Those charges could be detonated simultaneously or separately to form each set of nested protrusions "P" "P2" and "P3" simultaneously or separately along the axis of the wellbore.

The reduced number of pores, channels, or other cement imperfections allowing annulus leaks in the compressed cement "CC". "CC2" and "CC3" reduces the risk of seepage into the cement and helps seal against annulus flow through the consolidated cement. Further, the protrusions "P", "P2" and "P3" may create a ledge or barrier that helps seal that portion of the wellbore from seepage of outside materials. The size and shape of the protrusions "P", "P2" and "P3" may vary depending on several factors, including, but not limited to, the size (e.g., thickness), strength and material of the tubulars T1. T2 and T3, the type and amount of the explosive material, the hydrostatic pressure bearing on the tubulars T1, T2 and T3, the desired size of the protrusions "P", "P2" and "P3", and the nature of the wellbore operation.

For illustrative simplicity in FIGS. 2O and 2P, three nested tubulars T1, T2 and T3 and the other nested tubular "AP" or formation "F" are shown. However, the method may include more than one intermediate tubular T2, such that the wall of the innermost tubular T1, the walls of multiple intermediate tubulars 12, and the wall of the third tubular T3 are expanded radially outward with one single detonation of the explosive material contained in the tool without perforating or cutting through any of the nested tubulars thus arranged. The single detonation would form a nested protrusion in each tubular that extends into the annulus between the adjacent nested tubulars. That is, method discussed herein is not limited to selectively expanding the wall of three nested tubulars with a single dentation of the explosive material contained in the tool, but may include selectively expanding the wall of four or more nested tubulars with a single dentation of the explosive material.

A variation of the shape charge tool 10 is illustrated in FIG. 4. In this embodiment, the axial aperture 80 in the thrust disc 46 is tapered with a conically convergent diameter from the disc face proximate of the detonator 31 to the central aperture 62. The thrust disc aperture 80 may have a taper angle of about 10 degrees between an approximately 0.2 centimeters (0.08 inches) inner diameter to an approximately 0.32 centimeters (0.13 inches) diameter outer diameter. The taper angle, also characterized as the included angle, is the angle measured between diametrically opposite conical surfaces in a plane that includes the conical axis 13.

Original initiation of the FIG. 4 charge 60 occurs at the outer plane of the tapered aperture 80 having a proximity to a detonator 31 that enables/enhances initiation of the charge 60 and the concentration of the resulting explosive force. The initiation shock wave propagates inwardly along the tapered aperture 80 toward the explosive junction plane 64. As the shock wave progresses axially along the aperture 80, the concentration of shock wave energy intensifies due to the progressively increased confinement and concentration of the explosive energy. Consequently, the detonator shock wave strikes the charge units 60 at the inner juncture plane 64 with an amplified impact. Comparatively, the same explosive charge units 60, as suggested for FIG. 1 comprising, for example, approximately 38.8 grams (1.4 ounces) of HMX compressed under a loading pressure of about 20.7 Mpa (3,000 psi) and when placed in the FIG. 4 embodiment, may require only a relatively small detonator 31 of HMX for detonation. Significantly, the conically tapered aperture 80 of FIG. 4 appears to focus the detonator energy to the central aperture 62, thereby igniting a given charge with much less source energy. In FIGS. 1 and 4, the detonator 31 emits a detonation wave of energy that is reflected (bounce-back of the shock wave) off the flat internal end-face 33 of the integral end wall 32 of the housing 20 thereby amplifying a focused concentration of detonation energy in the central aperture 62. Because the tapered aperture 80 in the FIG. 4 embodiment reduces the volume available for the detonation wave, the concentration of detonation energy becomes amplified relative to the FIG. 1 embodiment that does not include the tapered aperture 80.

Figure 5:
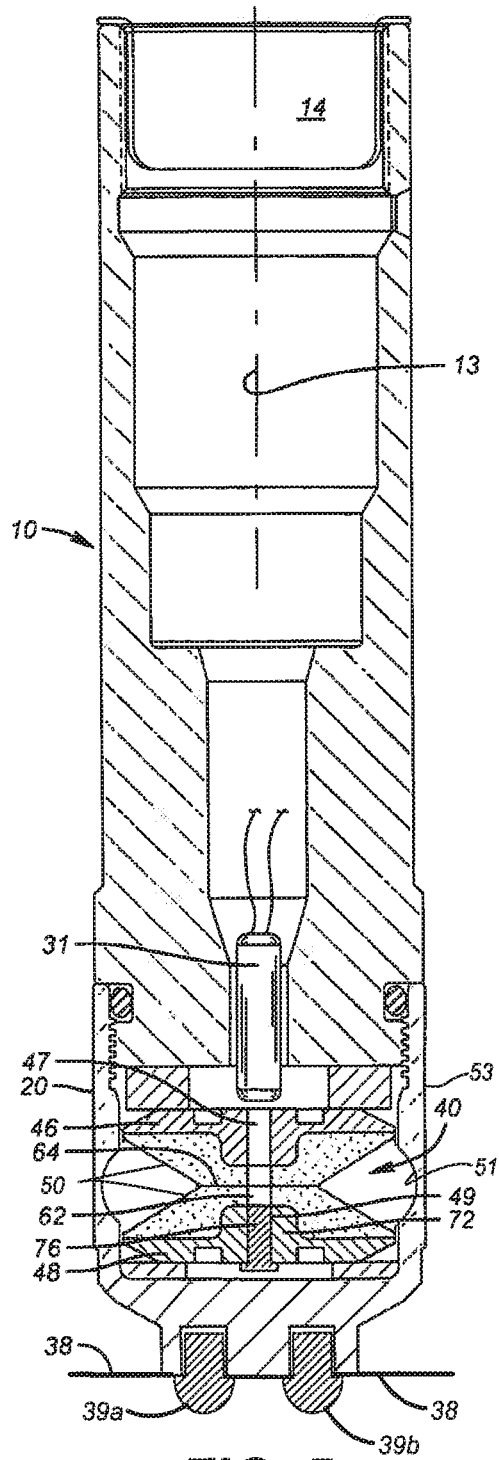
FIG. 5 is a cross-section of an embodiment of the tool, including a shaped charge assembly.

The variation of the tool 10 shown in FIG. 5 relies upon an open, substantially cylindrical aperture 47 in the upper thrust disc 46 as shown in the FIG. 1 embodiment. However, either no aperture is provided in the end plate boss 72 of FIG. 5 or the aperture 49 in the lower end plate 48 is filled with a dense, metallic plug 76, as shown in FIG. 5. The plug 76 may be inserted in the aperture 49 upon final assembly or pressed into place beforehand. As in the case of the FIG. 4 embodiment, the FIG. 5 tool 10 comprising, for example, approximately 38.8 grams (1.4 ounces) of HMX compressed under a loading pressure of about 20.7 Mpa (3,000 psi), also may require only a relatively small detonator 31 of HMX for detonation. The detonation wave emitted by the detonator 31 is reflected back upon itself in the central aperture 62 by the plug 76, thereby amplifying a focused concentration of detonation energy in the central aperture 62.

Figure 6:
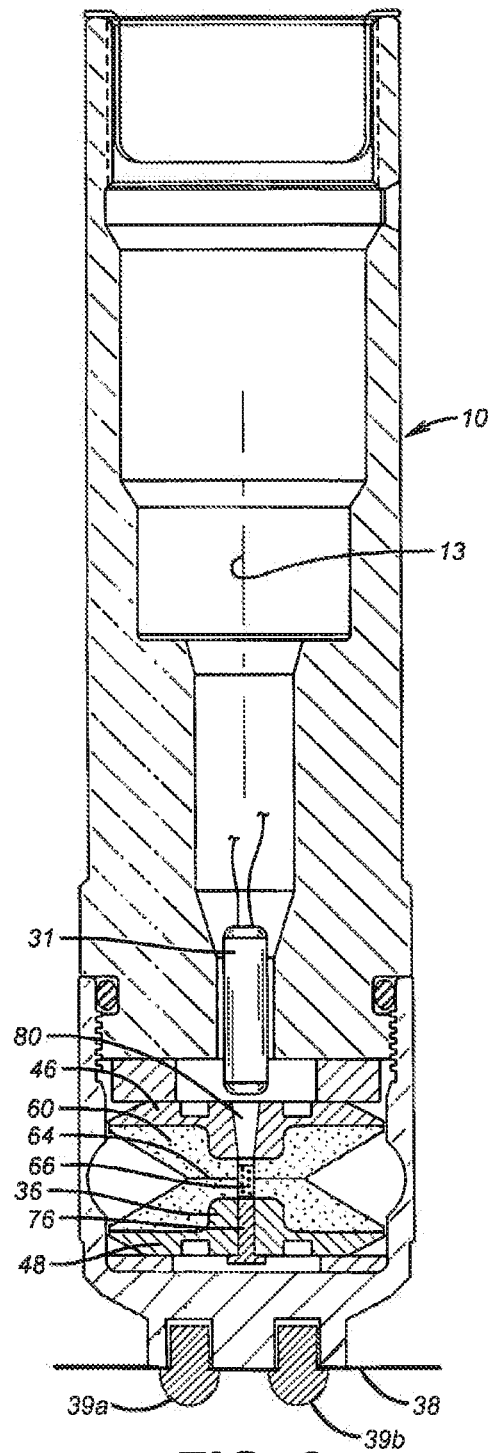
FIG. 6 is a cross-section of an embodiment of the tool, including a shaped charge assembly.

The FIG. 6 variation of the tool 10 combines the energy concentrating features of FIG. 2 and FIG. 5, and adds a relatively small, explosive initiation pellet 66 in the central aperture 62. In this case, the detonation wave of energy emitted from the detonator 31 is reflected off of explosive initiation pellet 66. The reflection from the off of explosive initiation pellet 66 is closer to the juncture plane 64, which results in a greater concentration of energy (enhanced explosive force). The explosive initiation pellet 66 concept can be applied to the FIG. 1 embodiment, also.

Transporting and storing the explosive units may be hazardous. There are thus safety guidelines and standards governing the transportation and storage of such. One of the ways to mitigate the hazard associated with transporting and storing the explosive units is to divide the units into smaller component pieces. The smaller component pieces may not pose the same explosive risk during transportation and storage as a full-size unit may have. Each of the explosive units 60 discussed herein may thus be provided as a set of units that can be transported unassembled, where their physical proximity to each other in the shipping box would prevent mass (sympathetic) detonation if one explosive component was detonated, or if, in a fire, would burn and not detonate. The set is configured to be easily assembled at the job site.

Figure 10:
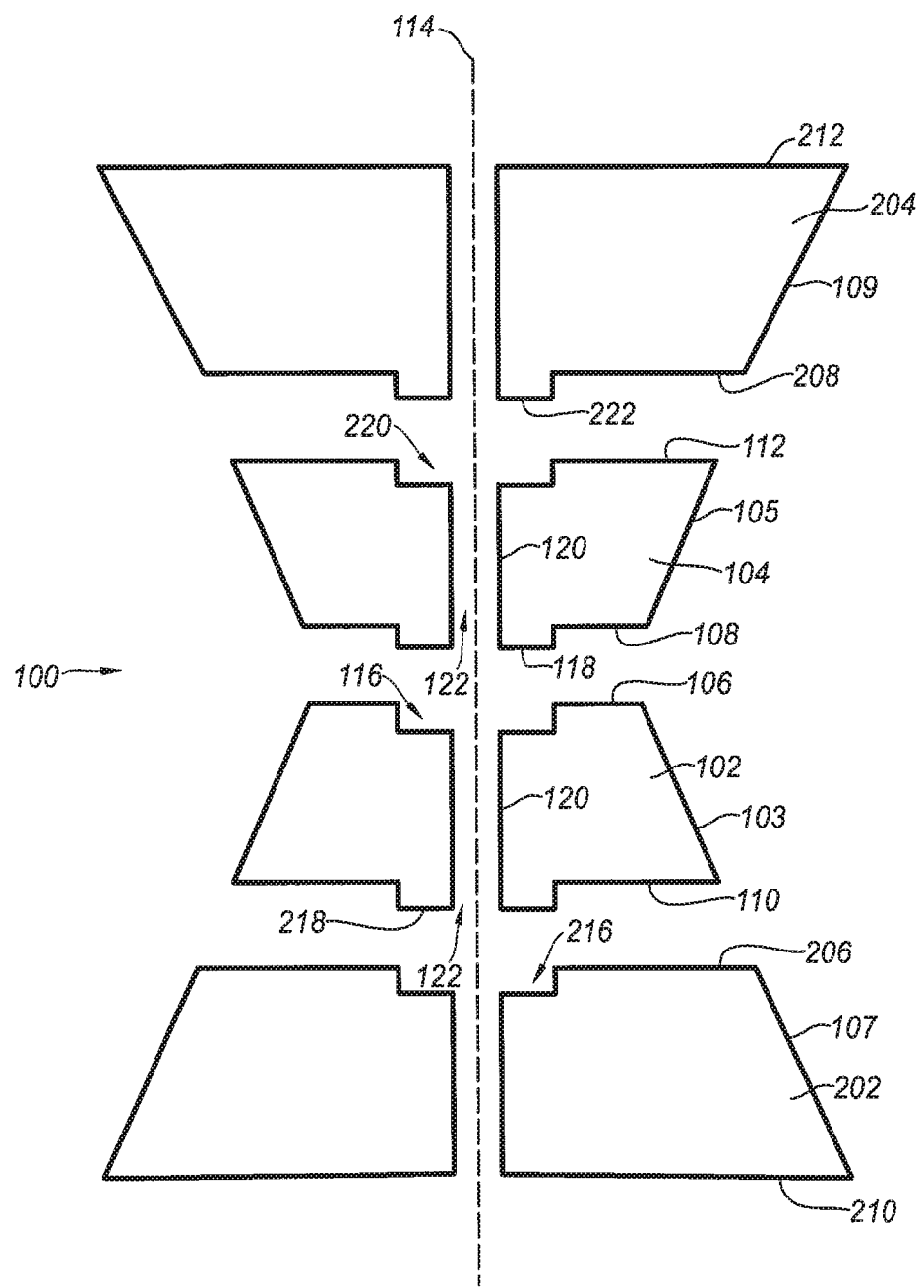
FIG. 10 illustrates an embodiment of a set of explosive units.

FIG. 10 shows an exemplary embodiment of a set 100 of explosive units. Embodiments of the explosive units discussed herein may be configured as the set 100 discussed below. The set 100 comprises a first explosive unit 102 and a second explosive unit 104. Each of the first explosive unit 102 and the second explosive unit 104 comprises the explosive material discussed herein. Each explosive unit 102, 104 may be frusto-conically shaped. In this configuration, the first explosive unit 102 includes a smaller area first surface 106 and a greater area second surface 110 opposite to the smaller area first surface 106. Similarly, the second explosive unit 104 includes a smaller area first surface 108 and a greater area second surface 112 opposite to the smaller area first surface 108. Each of the first explosive unit 102 and the second explosive unit 104 may be symmetric about a longitudinal axis 114 extending through the units, as shown in the perspective view of FIG. 11. Each of the first explosive unit 102 and the second explosive unit 104 comprises a center portion 120 having an aperture 122 that extends through the center portion 120 along the longitudinal axis 114.

In the illustrated embodiment, the smaller area first surface 106 of the first explosive unit 102 includes a recess 116, and the smaller area first surface 108 of the second explosive unit 104 comprises a protrusion 118. The first explosive unit 102 and the second explosive unit 104 are configured to be connected together with the smaller area first surface 106 of the first explosive unit 102 facing the second explosive unit 104, and the smaller area first surface 108 of the second explosive unit 104 facing the smaller area first surface 106 of the first explosive unit 102. The protrusion 118 of the second explosive unit 104 fits into the recess 116 of the first explosive unit 102 to join the first explosive unit 102 and the second explosive unit 104 together. The first explosive unit 102 and the second explosive unit 104 can thus be easily connected together without using tools or other materials.

Figure 13:
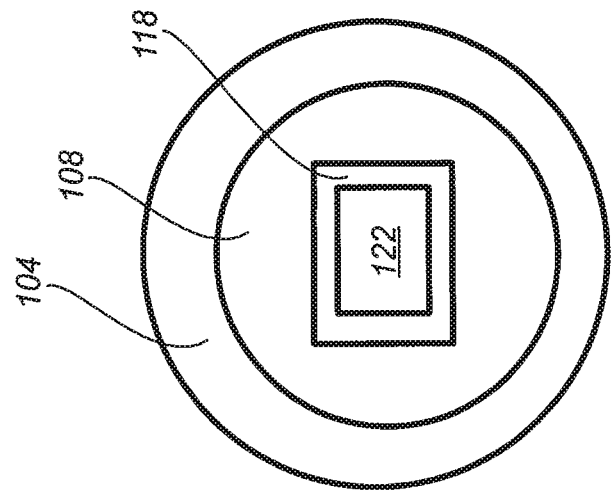
FIG. 13 shows a planform view of an alternative embodiment of an explosive unit in the set.
Figure 12:
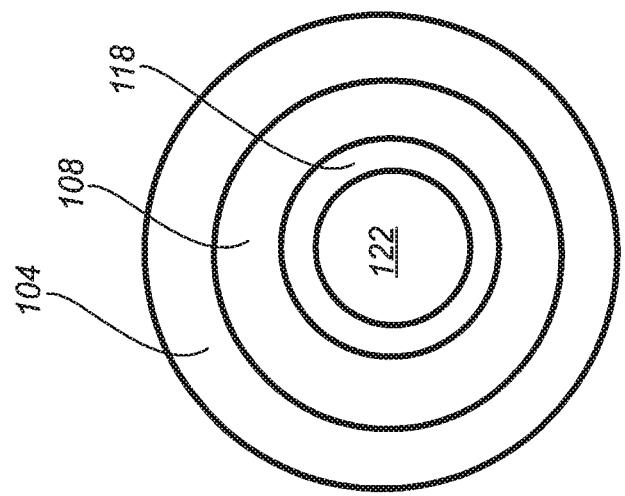
FIG. 12 shows a planform view of an explosive unit in the set.
Figure 11:
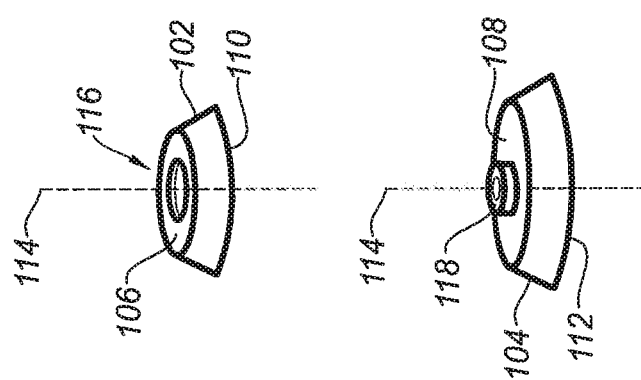
FIG. 11 illustrates a perspective view of explosive units in the set.

In the embodiment, the protrusion 118 and the recess 116 have a circular shape in planform, as shown in FIGS. 11 and 12. In other embodiments, the protrusion 118 and the recess 116 may have a different shape. For instance, FIG. 13 shows that the shape of the protrusion 118 is square. The corresponding recess (not shown) on the other explosive unit in this embodiment is also square to fitably accommodate the protrusion 118. Alternative shapes for the protrusion 118 and the recess 116 may be triangular, rectangular, pentagonal, hexagonal, octagonal or other polygonal shape having more than two sides.

Referring back to FIG. 10, the set 100 of explosive units can include a first explosive sub unit 202 and a second explosive sub unit 204. The first explosive sub unit 202 is configured to be connected to the first explosive unit 102, and the second explosive sub unit 204 is configured to be connected to the second explosive unit 104, as discussed below. Similar to the first and second explosive units 102, 104 discussed above, each of the first explosive sub unit 202 and the second explosive sub unit 204 can be frusto-conical so that the sub units define smaller area first surfaces 206, 208 and greater area second surfaces 210, 212 opposite to the smaller area first surfaces 206, 208, as shown in FIG. 10.

In the embodiment shown in FIG. 10, the larger area second surface 110 of the first explosive unit 102 includes a first projection 218, and the smaller area first surface 206 of the first explosive sub unit 202 includes a first cavity or recessed area 216. The first projection 218 fits into the first cavity or recessed area 216 to join the first explosive unit 102 and the first explosive sub unit 202 together. Of course, instead of having the first projection 218 on the first explosive unit 102 and the first cavity or recessed area 216 on the first explosive sub unit 202, the first projection 218 may be provided on the smaller area first surface 206 of the first explosive sub unit 202 and the first cavity 216 may be provided on the larger area second surface 110 of the first explosive unit 102.

FIG. 10 also shows that the larger area second surface 112 of the second explosive unit 104 comprises a first cavity or recessed area 220, and the smaller area first surface 208 of the second explosive sub unit 204 comprises a first projection 222. The first projection 222 fits into the first cavity or recessed area 220 to join the second explosive unit 102 and the second explosive sub unit 204 together. Of course, instead of having the first projection 222 on the second explosive sub unit 204 and the first cavity 220 on the second explosive unit 104, the first projection 222 may be provided on the larger area second surface 112 of the second explosive unit 104 and the first cavity 220 may be provided on the smaller area first surface 208 of the second explosive sub unit 204. The first and second explosive sub units 202, 204 may also include the aperture 122 extending along the longitudinal axis 114.

FIGS. 10 and 11 show that the first explosive unit 102 includes a side surface 103 connecting the smaller area first surface 106 and the greater area second surface 110. Similarly, the second explosive unit 104 includes a side surface 105 connecting the smaller area first surface 108 and the greater area second surface 112. Each side surface 103, 105 may consist of only the explosive material, so that the explosive material is exposed at the side surfaces 103, 105. In other words, the liner that is conventionally applied to the explosive units is absent from the first and second explosive units 102, 104. The side surfaces 107, 109 of the first and second explosive sub units 202, 204, respectively, can consist of only the explosive material, so that the explosive material is exposed at the side surfaces 107, 109, and the liner is absent from the first and second explosive sub units 202, 204.

FIGS. 14-17 illustrate another embodiment of an explosive unit 300 that may be included in a set of several similar units 300. The explosive unit 300 may be positioned in a tool 10 at a location and orientation that is opposite a similar explosive unit 300, in the same manner as the explosive material units 60 in FIGS. 1 and 4-6 discussed herein. FIG. 14 is a plan view of the explosive unit 300. FIG. 15 is a plan view of one segment 302 of the explosive unit 300, and FIG. 16 is a side view thereof. FIG. 17 is a cross-sectional side view of FIG. 15. In the embodiment, the explosive unit 300 is in the shape of a frustoconical disc that is formed of three equally-sized segments 301, 302, and 303. The explosive unit 300 may include a central opening 304, as shown in FIG. 14, for accommodating the shaft of an explosive booster (not shown). The illustrated embodiment shows that the explosive unit 300 is formed of three segments 301, 302, and 303, each accounting for one third (i.e., 120 degrees) of the entire explosive unit 300 (i.e., 360 degrees). However, the explosive unit 300 is not limited to this embodiment, and may include two segments or four or more segments depending nature of the explosive material forming segments. For instance, a more highly explosive material may require a greater number of (smaller) segments in order to comply with industry regulations for safely transporting explosive material. For instance, the explosive unit 30) may be formed of four segments, each accounting for one quarter (i.e., 90 degrees) of the entire explosive unit 300 (i.e., 360 degrees); or may be formed of six segments, each accounting for one sixth (i.e., 60 degrees) of the entire explosive unit 300 (i.e., 360 degrees). According to one embodiment, each segment should include no more than 38.8 grams (1.4 ounces) of explosive material.

In one embodiment, the explosive unit 300 may have a diameter of about 8.38 centimeters (3.3 inches). FIGS. 15 and 16 show that the segment 302 has a top surface 305 and a bottom portion 306 having a side wall 307. The top surface 305 may be slanted an angle of 17 degrees from the central opening 304 to the side wall 307 in an embodiment. According to one embodiment, the overall height of the segment 302 may be about 1.905 centimeters (0.75 inches), with the side wall 307 being about 0.508 centimeters (0.2 inches) of the overall height. The overall length of the segment 302 may be about 7.24 centimeters (2.85 inches) in the embodiment. FIG. 17 shows that the inner bottom surface 308 of the segment 302 may be inclined at an angle of 32 degrees, according to one embodiment. The width of the bottom portion 306 may be about 1.37 centimeters (0.54 inches) according to an embodiment with respect to FIG. 17. The side wall 309 of the central opening 304 may have a height of about 0.356 centimeters (0.14 inches) in an embodiment, and the uppermost part 310 of the segment 302 may have a width of the about 0.381 centimeters (0.15 inches). The above dimensions are not limiting, as the segment size and number may be different in other embodiments. A different segment size and/or number may have different dimensions. The explosive units 300 may be provided as a set of units divided into segments, so that the explosive units 300 can be transported as unassembled segments 301, 302, 303, as discussed above.

The set of segments is configured to be easily assembled at the job site. Thus, a method of selectively expanding at least a portion of a wall of a tubular at a well site via a shaped charge tool 10 may include first receiving an unassembled set of explosive units 300 at the well site, wherein each explosive unit 300 comprising explosive material, is divided multiple segments 301, 302, 303 that, when joined together, form an explosive unit 300. The method includes assembling the tool 10 (see. e.g., FIG. 1) comprising a shaped charge assembly comprising a housing 20 and two end plates 46, 48. The housing 20 comprises an inner surface 51 facing an interior of the housing 20. At the well site, the segments 301, 302, 303 of each explosive unit 300 are together to form the assembled explosive unit 300. The explosive units 300 are then positioned between the two end plates 46, 48, for instance each explosive unit 300 is adjacent one of the end plates 46, 48, so that an exterior surface of the explosive material of explosive units 300 faces the inner surface 51 of the housing 20. In an embodiment, the explosive material is exposed to the inner surface 51 of the housing 20. Next, a detonator 31 is positioned adjacent to one of the two end plates 46, 48, and the shaped charge tool 10 is positioned within the tubular. The detonator 31 is then actuated to ignite the explosive material causing a shock wave that travels radially outward to impact the tubular at a first location and expand at least a portion of the wall of the tubular radially outward without perforating or cutting through the portion of the wall, to form a protrusion of the tubular at the portion of the wall. The protrusion extends into an annulus between an outer surface of the wall of the tubular and an inner surface of a wall of another tubular or a formation.

FIGS. 18-22 show embodiments of a centralizer assembly that may be attached to the housing 20. The centralizer assembly centrally confines the tool 10 within the inner tubular T1. In the embodiment shown in FIG. 18, a planform view of the centralizer assembly is shown in relation to the longitudinal axis 13. The tool 10 is centralized by a pair of substantially circular centralizing discs 316. Each of the centralizing discs 316 are secured to the housing 20 by individual anchor pin fasteners 318, such as screws or rivets. In the FIG. 18 embodiment, the discs 316 are mounted along a diameter line 320 across the housing 20, with the most distant points on the disc perimeters separated by a dimension that is preferably at least corresponding to the inside diameter of the inner tubular T1. In many cases, however, it will be desirable to have a disc perimeter separation slightly greater than the internal diameter of the inner tubular T1.

Figure 19:
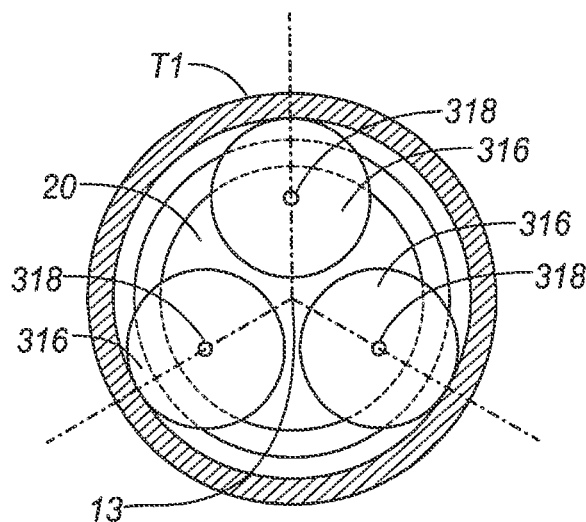
FIG. 19 illustrates an alternative embodiment of a centralizer assembly.

In another embodiment shown by FIG. 19, each of the three discs 316 are secured by separate pin fasteners 318 to the housing 20 at approximately 120 degree arcuate spacing about the longitudinal axis 13. This configuration is representative of applications for a multiplicity of centering discs on the housing 20. Depending on the relative sizes of the tool 10 and the inner tubular T1, there may be three or more such discs distributed at substantially uniform arcs about the tool circumference.

Figure 20:
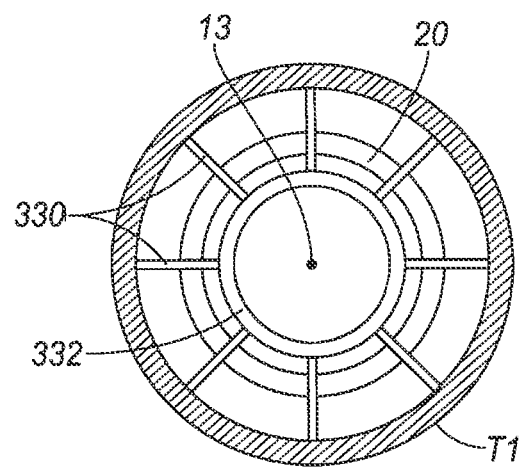
FIG. 20 illustrates another embodiment of a centralizer assembly.

FIG. 20 shows, in planform, another embodiment of the centralizers that includes spring steel centralizing wires 330 of small gage diameter. A plurality of these wires is arranged radially from an end boss 332. The wires 330 can be formed of high-carbon steel, stainless steel, or any metallic or metallic composite material with sufficient flexibility and tensile strength. While the embodiment includes a total of eight centralizing wires 330, it should be appreciated that the plurality may be made up of any number of centralizing wires 330, or in some cases, as few as two. The use of centralizing wires 330 rather than blades or other machined pieces, allows for the advantageous maximization of space in the flowbore around the centralizing system, compared to previous spider-type centralizers, by minimizing the cross-section compared to systems featuring flat blades or other planar configurations. The wires 330 are oriented perpendicular to the longitudinal axis 13 and engaged with the sides of the inner tubular, which is positioned within an outer tubular T2. The wires 330 may be sized with a length to exert a compressive force to the tool 10, and flex in the same fashion as the cross-section of discs 316 during insertion and withdrawal.

Figure 18:
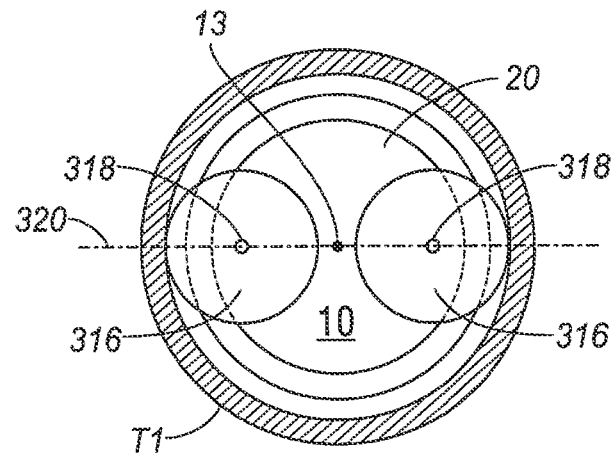
FIG. 18 illustrates an embodiment of a centralizer assembly.
Figure 21:
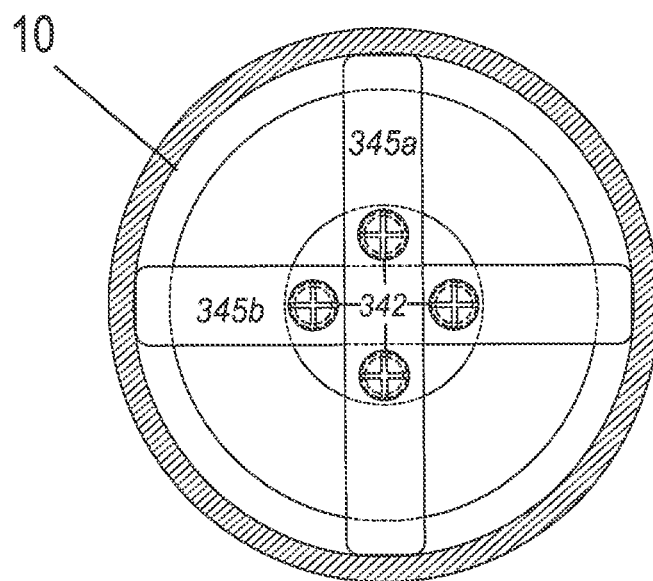
FIGS. 21 and 22 illustrate a further embodiment of a centralizer assembly.
Figure 22:
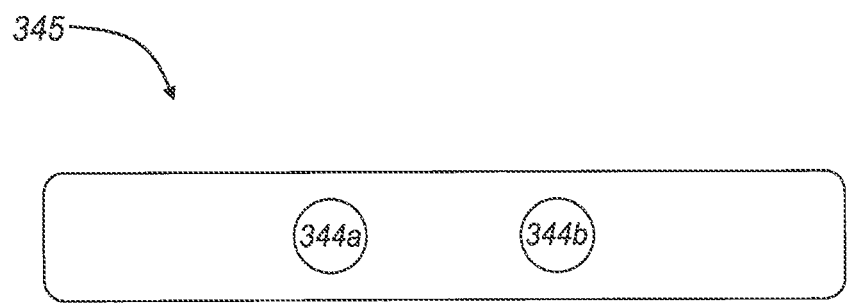

Another embodiment of the centralizer assembly is shown in FIG. 21. This configuration comprises a plurality of planar blades 345a, 345b to centralize the tool 10. The blades 345a, 345b are positioned on the bottom surface of the tool 10 via a plurality of fasteners 342. The blades 345a, 345b thus flex against the sides of the inner tubular T1 to exert a centralizing force in substantially the same fashion as the disc embodiments discussed above. FIG. 18 illustrates an embodiment of a single blade 345. The blade 345 comprises a plurality of attachment points 344a, 344b, through which fasteners 342 secure the blade 345 in position. Each fastener 342 can extend through a respective attachment point to secure the blade 345 into position. While the embodiment in FIG. 21 is depicted with two blades 345a, 345b, and each blade 345 comprises two attachment points, for a total of four fasteners 342 and four attachment points (344a, 344b are pictured in FIG. 22), it should be appreciated that the centralizer assembly may comprise any number of fasteners and attachment points.

The multiple attachment points 344a, 344b on each blade 345, being spaced laterally from each other, prevent the unintentional rotation of individual blades 345, even in the event that the fasteners 342 are slightly loose from the attachment points 344a, 344b. The fasteners 342 can be of any type of fastener usable for securing the blades into position, including screws. The blades 345 can be spaced laterally and oriented perpendicular to each other, for centralizing the tool 10 and preventing unintentional rotation of the one or more blades 345.

Figure 24:
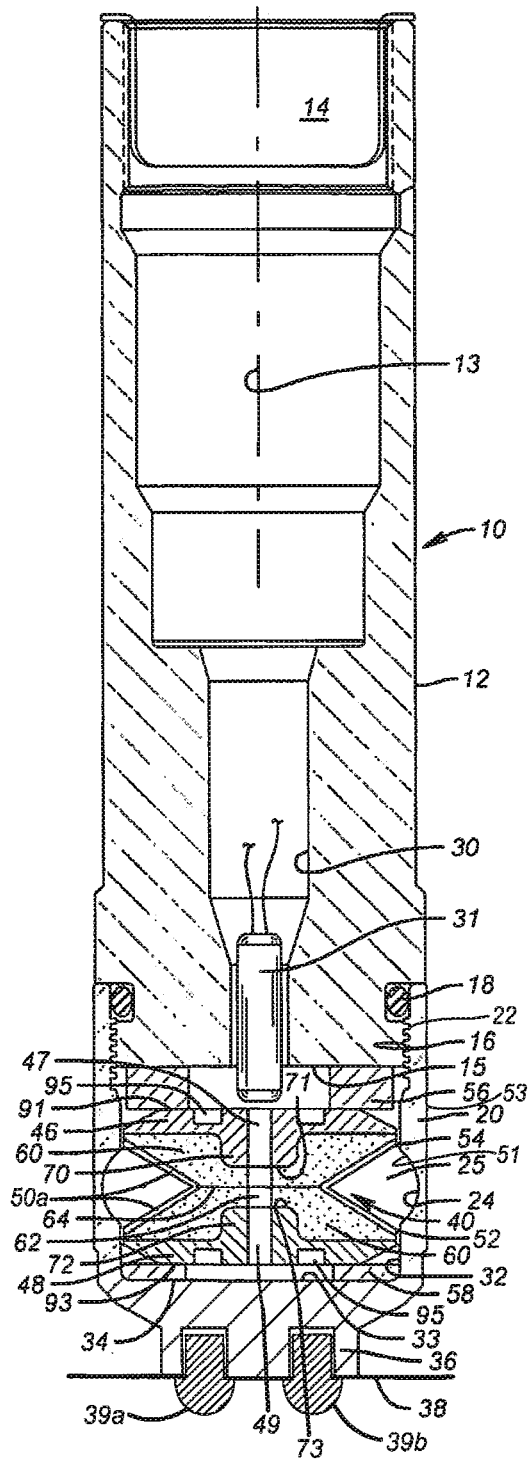
FIG. 24 is a cross-section of further embodiment of a tool, including a shaped charge assembly, for selectively expanding at least a portion of a wall of a tubular.

While the disclosure above discusses embodiments in which there is no liner on the exterior surface 50 of the explosive units 60 (i.e., the exterior surface 50 of the explosive units 60 is exposed to the inner surface 51 of the housing 20), alternative embodiments of the present disclosure may include a liner 50a on the exterior surface of the explosive units 60, as shown in FIG. 24, and may be able to achieve similar results as the liner-less explosive units 60 according to the following criteria. Conventionally, liners for explosive units were formed of material with relatively high density and ductility so that, when collapsed by a detonation wave of the ignited explosive units, the liners form a jet that is strong enough to penetrate the pipe or tubular in a cutting or perforating operation. Conventional materials for such liners included copper, nickel, zinc, zinc alloy, iron, tin, bismuth, and tungsten.

On the other hand, a liner formed of a relatively low density and brittle material would not jet as well as the conventional materials discussed above. The present inventor has determined that a formed of a material that is less dense and ductile than copper, nickel, zinc, zinc alloy, iron, tin, bismuth, and tungsten, individually or in combination, (i.e., formed of a material that is brittle and has low density), may be effective in expanding, without puncturing, the wall of the tubular T1 to form the protrusion "P" discussed herein. In this regard, an embodiment of the liner 50a may have a density of 6 g/cc or less, and may be less ductal than copper, nickel, zinc, zinc alloy, iron, tin, bismuth, and tungsten, individually or in combination. In an embodiment, the liner 50a may be formed of glass material. In another embodiment, the liner 50a may be formed of a plastic material.

Another way to reduce the potency of the liner jet, so that the jet may expand, without puncturing, the wall of the tubular T1 to form the protrusion "P" discussed herein, is to perforate the liner 50a. In addition, or in the alternative, the liner 50a may be formed so that a density, wall thickness, and/or composition of the liner 50a is asymmetric around at least one of the explosive units 60. In addition, or in the alternative, the explosive units 60 may be formed so that a density, wall thickness, and/or composition of the explosive units 60 is asymmetric around at least one of the explosive units 60. Further, the liner 50a of at least one of the explosive units 60 may be geometrically asymmetric. Asymmetric explosive units 60 may reduce the potency of explosive units 60 so that detonation of the explosive units 60 may expand, without puncturing, the wall of the tubular T1 to form the protrusion "P" discussed herein. Similarly, asymmetric liners may reduce the potency of the jet formed by the liners, so that the jet may expand, without puncturing, the wall of the tubular T1 to form the protrusion "P" discussed herein.

Figure 25:
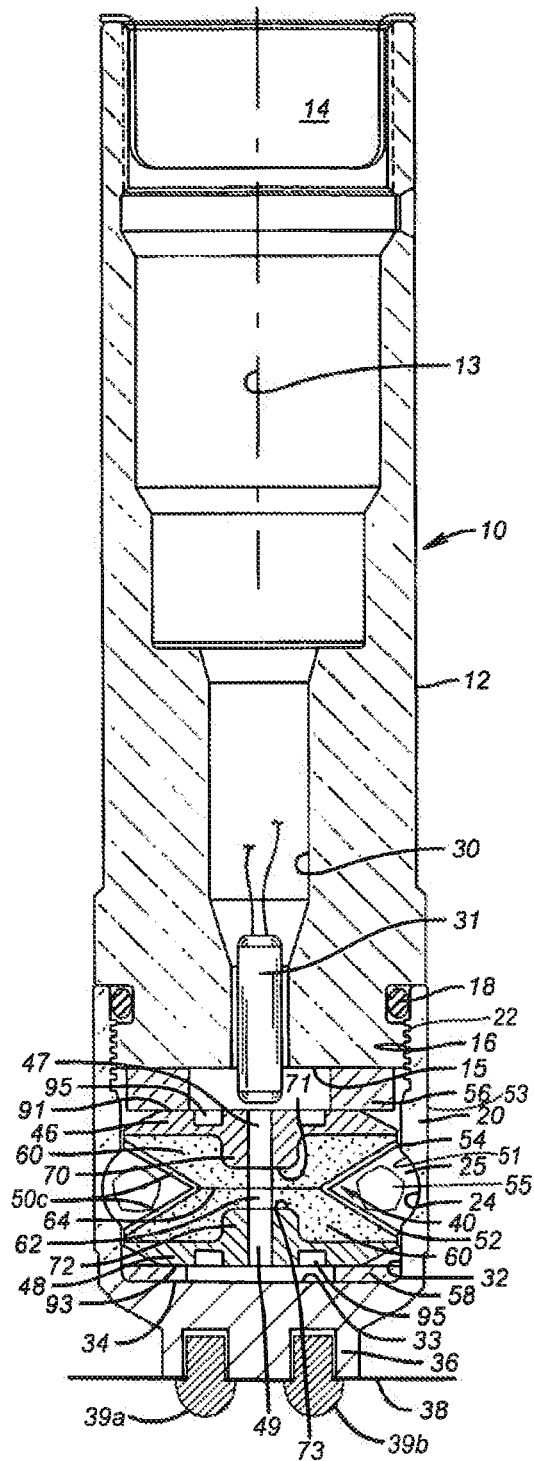
FIG. 25 is a cross-section of further embodiment of a tool, including a shaped charge assembly, for selectively expanding at least a portion of a wall of a tubular.

FIG. 25 illustrates another embodiment of a tool 10 for selectively expanding at least a portion of a wall of a tubular. The tool 10 in this embodiment comprises a liner 50c on the outer surface of the explosive units 60. The liner 50c may be a liner formed of the conventional materials discussed above (e.g., copper, nickel, zinc, zinc alloy, iron, tin, bismuth, and tungsten). The tool 10 further comprises an extraneous object 55 located between the inner surface of the housing 20 and the liner 50c. The extraneous object 55 fouls the jet formed by the liner 50c so that the jet expands, without puncturing, a portion of the wall of the tubular T1 to form a protrusion "P" extending outward into an annulus adjacent the wall of the tubular T1, as discussed herein. The extraneous object 55 may be one of a foam object, a rubber object, a wood object, and a liquid object, among other things.

FIGS. 26A-26D illustrate a method of reducing a leak 505, such as a micro annulus leak as discussed herein, in an annulus 502 adjacent a tubular 501 in a wellbore 500. The method may also be implemented, for example, in a plug-and-abandonment operation. FIG. 26A shows an example of a wellbore 500 that includes an annulus 502 disposed between an inner tubular 501 and an outer tubular, or formation, 504. The tubular 501 may be the same or akin to the tubular(s) discussed herein. The annulus 502 may contain a sealant 503, such as cement. A leak 505 may exist in the annulus 502. The leak 505 may be an oil leak, a gas leak, or a combination thereof. The method may begin with setting a plug 506 at a location within the tubular 501 as shown in FIG. 26B to prevent fluid, gases, and/or other wellbore materials from traveling up the tubular 501 past the plug 506. The plug 506 may be a cast iron bridge plug, a cement plug, or any plug which isolates the lower portion of the well from the upper portion of the well. The plug 506 may also be used to seal the tubular 501 and/or provide a stop for a sealant, such as cement, that may be pumped into the annulus 502 from the tubular 501 in the following manner. One or more puncher charges (not shown) may be inserted into the tubular 501 and actuated to punch holes 507 in the wall of the tubular 501 at a location uphole of the plug 506, as shown in FIG. 26C. The puncher charges may be any commercially available shaped charges that when detonated form a jet of limited length to "punch" a hole in the target pipe without damaging any member beyond the target pipe. The holes 507 can serve as passages for a sealant, such as cement, that can be subsequently pumped, or otherwise provided, into the tubular 501 and squeezed through the holes 507 into the annulus 502. As shown in FIG. 26), the sealant (e.g., cement) is squeezed through the holes 507 and into the annulus 502 to densify the sealant (see densified sealant 508) that is already present in the annulus 502, or otherwise to fill the annulus 502, for sealing or reducing the leak 505. By some estimates, the method of reducing the leak 505 in the annulus 502, as discussed with respect to FIGS. 26A to 26D, may be only 35% successful.

A more successful method of reducing a leak 505 in the annulus 502 adjacent a tubular 501 in a wellbore 500 is shown in FIGS. 27A to 27E. FIG. 27A illustrates a scenario, as discussed above, in which a leak 505 exists in the annulus 502 adjacent a tubular 501 in a wellbore 500. As before, a plug 506 may be set at a location within the tubular 501, as shown in FIG. 27B. The plug 506 may be the same as the plug 506 discussed above. Next, an expansion tool 509 containing an amount of explosive material is inserted into the tubular 501 uphole of the plug 506 as shown in FIG. 27C. The expansion tool 509 may be any one of the expansion tools and their variations as discussed herein. The explosive material may be any of the explosive materials discussed herein or other HMX, RDX or HNS material. Other characteristics of the tubular and/or the wellbore may also be determined and/or accounted for, as discussed above, as necessary or as desired to determine the amount of explosive material in the expansion tool 509. The amount of explosive material in the expansion tool 509 may be based at least in part on a hydrostatic pressure bearing on the tubular 501 in the wellbore 500, as discussed herein. The amount of explosive material produces an explosive force sufficient to expand, without puncturing, the wall of the tubular 501. The expansion tool 509 may then be actuated to expand the wall of the tubular 501 radially outward, without perforating or cutting through the wall of the tubular 501, to form one or more protrusions 510 as shown in FIG. 27C. Each protrusion 510 extends into the annulus 502 adjacent an outer surface of the wall of the tubular 501, in the manner(s) discussed herein. The protrusions 510 may seal off, or may help seal off, the annulus 502 by protruding toward or against the outer pipe 504 (or formation) surrounding the annulus 502. For instance, FIG. 27C shows that the protrusions 510 may densify the sealant (see densified sealant 508) already present in the annulus 502, or otherwise fill the annulus 502, to seal or reduce the leak 505. The protrusions 510 may seal off, or may help seal off, the annulus 502 against leaks in the sealant 503 by compressing any voids in the sealant 503 and/or collapsing open channels in a cemented annulus 502. In some cases, the protrusions 510 extending into the annulus may be enough to provide an acceptable seal against the leak 505 moving uphole beyond the protrusions 510, and no further remedial action may be required. By some estimates, the manner of reducing the leak 505 in the annulus 502 as discussed with respect to FIGS. 27A to 27C may be at least 70% successful. To increase the success rate, if needed, additional steps to reduce the leak 505 in the annulus 502 are shown in FIGS. 27D and 27E.

In particular, one or more puncher charges (not shown) may be subsequently inserted into the tubular 501 and actuated to punch holes 507 in the wall of the tubular 501 as shown in FIG. 27D. The puncher charges may be the same as those discussed above. As discussed above, the holes 507 serve as passages for a sealant, such as cement, to subsequently be pumped, or otherwise provided, into the tubular 501 and squeezed through the holes 507 into the annulus 502, at least down to the upper protrusion 510. As shown in FIG. 27E, the sealant (e.g., cement) can be squeezed through the holes 507 into the annulus 502 to densify the sealant (see densified sealant 508) already present in the annulus 502, or otherwise to fill the annulus 502, for sealing or reducing the leak 505, at least down to the upper protrusion 510. In some cases, however, the cement squeezed through the holes 507 may travel down beyond the upper protrusion 510 if any voids or channels in the densified sealant 508 are large enough to permit such flow. In addition, the protrusions 510 may form a restriction or a ledge below where the cement 507 will be introduced into the annulus 502. If the sealant is viscous enough, the protrusion 510 may provide the annulus seal by itself. By some estimates, the method of reducing the leak 505 in the annulus 502 as discussed with respect to FIGS. 27D and 27E may be at least 90% successful.

In the embodiments discussed above, expansion tools including one or more expansion charges have been discussed. The expansion charges may be shaped charges as discussed above. However, a dual end firing tool or single end firing tool may also be used to expand, without puncturing, the wall of the tubular to form a protrusion extending outward into the annulus adjacent the wall of the tubular as discussed herein. Dual end fired and single end fired cylindrical explosive column tools (e.g., modified pressure balanced or pressure bearing severing tools) produce a focused energetic reaction, but with much less focus than from shaped charge expanders. In dual end fired explosive column tools, the focus is achieved via the dual end firing of the explosive column, in which the two explosive wave fronts collide in a middle part of the column, amplifying the pressure radially. In single end fired explosive column tools, the focus is achieved via the firing of the explosive column from one end which generates one wave front producing comparatively less energy. The single wave front may form a protrusion in the wall of the tubular, without perforating or cutting through the wall. The protrusion formed by a single end fired explosive column tool may be asymmetric as compared with a protrusion formed by a dual end fired explosive column tool. The length of the selective expansion in both types of explosive column tools is a function of the length of the explosive column, and may generally be about two times the length of the explosive column. With a relatively longer expansion length, for example, 40.64 centimeters (16.0 inches) as compared to a 10.16 centimeter (4.0 inch) expansion length with a shaped charge explosive device, a much more gradual expansion is realized. The more gradual expansion allows a greater expansion of any tubular or pipe prior to exceeding the elastic strength of the tubular or pipe, and failure of the tubular or pipe (i.e., the tubular or pipe being breeched).

An embodiment of an expansion tool 600 for selectively expanding at least a portion of a wall of a tubular is shown in FIGS. 28-30. The expansion tool 600, as shown in this embodiment, is a dual end firing explosive column tool, and can be used for applications involving relatively large and thicker tubulars, such as pipes having a 6.4 centimeter (2.5 inch) wall thickness, an inner diameter of 22.9 centimeters (9.0 inches) or more and an outer diameter of 35.6 centimeters (14.0 inches) or more. However, the dual end firing explosive column tool 600 is not limited to use with such larger tubulars, and may effectively be used to expand the wall of smaller diameter tubulars and tubulars with thinner walls than discussed above, or with larger diameter tubulars and tubulars with thicker walls than discussed above.

FIG. 28 shows a cross-sectional view of an embodiment of the dual end firing explosive column tool 600. In this embodiment, the dual end firing explosive column tool 60W is a modified pressure balanced tool. FIGS. 29 and 30 show details of particular portions of the dual end firing explosive column tool 600. As shown, the dual end firing explosive column tool 600 can include a top sub 612 at a proximal end thereof. An internal cavity 613 in the top sub 612 can be formed to receive a firing head (not shown). A guide tube 616 can be secured to the top sub 612 to project from an inside face 638 of the top sub 612 along an axis of the tool 600. The opposite distal end of guide tube 616 can support a guide tube terminal 618, which can be shaped as a disc. A threaded boss 619 can secure the terminal 618 to the guide tube 616. One or more resilient spacers 642, such as silicon foam washers, can be positioned to encompass the guide tube 616 and bear against the upper face of the terminal 618.

The dual end firing explosive column tool 600 can be arranged to serially align a plurality of high explosive pellets 640 along a central tube to form an explosive column. The pellets 640 may be pressed at forces to keep well fluid from migrating into the pellets 640. In addition, or in the alternative, the pellets 640 may be coated or sealed with glyptal or lacquer, or other compound(s), to prevent well fluid from migrating into the pellets 640. The dual end firing explosive column tool 600, as shown, is provided without an exterior housing so that the explosive pellets 640 can be exposed to an outside of the dual end firing explosive column tool 600, meaning that there is no housing of the dual end firing explosive column tool 600 covering the pellets 640. That is, when the dual end firing explosive column tool 600 is inserted into a pipe or other tubular, the explosive pellets 640 can be exposed to an inner surface of the pipe or other tubular. Alternatively, a sheet of thin material, or "scab housing" (not shown) may be provided with the dual end firing explosive column tool 600 to cover the pellets 640, for protecting the explosive material during running into the well. The material of the "scab housing" can be thin enough so that its effect on the explosive impact of the pellets 640 on the surface of the pipe or other tubular is immaterial. Moreover, the explosive force can vaporize or pulverize the "scab housing" so that no debris from the "scab housing" is left in the wellbore. In some embodiments, the "scab housing" may be formed of Teflon, PEEK, ceramic materials, or highly heat treated thin metal above 40 Rockwell "C". Bi-directional detonation boosters 624, 626 are positioned and connected to detonation cords 630, 632 for simultaneous detonation at opposite ends of the explosive column. Each of the pellets 640 can comprise about 22.7 grams (0.801 ounces) to about 38.8 grams (1.37 ounces) of high order explosive, such as RDX, HMX or HNS. The pellet density can be from, e.g., about 1.6 g/cm$^3$ (0.92 oz/in$^3$) to about 1.65 g/cm$^3$ (0.95 oz/in$^3$), to achieve a shock wave velocity greater than about 9,144 meters/sec (30,000 ft/sec), for example.

A shock wave of such magnitude can provide a pulse of pressure in the order of 27.6 Gpa (4×10$^6$ psi). It is the pressure pulse that expands the wall of the tubular. The pellets 640 can be compacted at a production facility into a cylindrical shape for serial, juxtaposed loading at the jobsite, as a column in the dual end firing explosive column tool 600. The dual end firing explosive column tool 600 can be configured to detonate the explosive pellet column at both ends simultaneously, in order to provide a shock front from one end colliding with the shock front to the opposite end within the pellet column at the center of the column length. On collision, the pressure is multiplied, at the point of collision, by about four to five times the normal pressure cited above. To achieve this result, the simultaneous firing of the bi-directional detonation boosters 624, 626 can be timed precisely in order to assure collision within the explosive column at the center. In an alternative embodiment, the expansion tool 600 may be a single end firing explosive column tool that includes a detonation booster at only one end of the explosive pellet column, so that the explosive column is detonated from only the one end adjacent the detonation booster, as discussed above, and so the configuration of the single end firing explosive column tool is similar to that of the dual end firing explosive column tool discussed herein.

Toward the upper end of the guide tube 616, an adjustably positioned partition disc 620 can be secured by a set screw 621. Between the partition disc 620 and the inside face 638 of the top sub 612 can be a timing spool 622, as shown in FIG. 28. A first bi-directional booster 624 can be located inside of the guide tube bore 616 at the proximal end thereof. One end of the first bi-directional booster 624 may abut against a bulkhead formed as an initiation pellet 612a. The first bi-directional booster 624 can have enough explosive material to ensure the requisite energy to breach the bulkhead. The opposite end of the first bi-directional booster 624 can comprise a pair of mild detonating cords 630 and 632, which can be secured within detonation proximity to a small quantity of explosive material 625 (See FIG. 29). Detonation proximity is that distance between a particular detonator and a particular receptor explosive within which ignition of the detonator will initiate a detonation of the receptor explosive. The detonation cords 630 and 632 can have the same length so as to detonate opposite ends of the explosive column of pellets 640 at the same time. As shown in FIGS. 28 and 30, the first detonating cord 630 can continue along the guide tube 616 bore to be secured within a third bi-directional booster 626 that can be proximate of the explosive material 627. A first window aperture 634 in the wall of guide tube 616 can be cut opposite of the third bi-directional booster 626, as shown. As shown in FIGS. 28 and 29, from the first bi-directional booster 624, the second detonating cord 632 can be threaded through a second window aperture 636 in the upper wall of guide tube 616 and around the helical surface channels of the timing spool 622. The timing spool, which is outside the cylindrical surface, can be helically channeled to receive a winding lay of detonation cord with insulating material separations between adjacent wraps of the cord. The distal end of second detonating cord 632 can terminate in a second bi-directional booster 628 that is set within a receptacle in the partition disc 620. The position of the partition disc 620 can be adjustable along the length of the guide tube 616 to accommodate the anticipated number of explosive pellets 640 to be loaded.

To load the dual end firing explosive column tool 600, the guide tube terminal 618 can be removed along with the resilient spacers 642 (See FIG. 30). The pellets 640 of powdered, high explosive material, such as RDX, HMX or HNS, can be pressed into narrow wheel shapes. The pellets 640 may be coated/sealed, as discussed above. A central aperture can be provided in each pellet 640 to receive the guide tube 616 therethrough. Transportation safety may limit the total weight of explosive in each pellet 640 to, for example, less than 38.8 grams (600 grains) (1.4 ounces). When pressed to a density of about 1.6 g/cm$^3$ (0.92 oz/in$^3$) to about 1.65 g/cm$^3$ (0.95 oz/in$^3$), the pellet diameter may determine the pellet thickness within a determinable limit range.

The pellets 640 can be loaded serially in a column along the guide tube 616 length with the first pellet 640, in juxtaposition against the lower face of partition disc 620 and in detonation proximity with the second bi-directional booster 628. The last pellet 640 most proximate of the terminus 618 is positioned adjacent to the first window aperture 634. The number of pellets 640 loaded into the dual end firing explosive column tool 600 can vary along the length of the tool 600 in order to adjust the size of the shock wave that results from igniting the pellets 640. The length of the guide tube 616, or of the explosive column formed by the pellets, may depend on the calculations or testing discussed below. Generally, the expansion length of the wall of the tubular can be about two times the length of the column of explosive pellets 640. In testing performed by the inventor, a 19.1 centimeters (7.5 inch) column of pellets 640 resulted in an expansion length of the wall of a tubular of 40.6 centimeters (16 inches) (i.e., a ratio of column length to expansion length of 1 to 2.13). Any space remaining between the face of the bottom-most pellet 640 and the guide tube terminal 618 due to fabrication tolerance variations may be filled, e.g., with resilient spacers 642.

FIGS. 31-33 illustrate another embodiment of an expansion tool 600'. The expansion tool 600' in this embodiment is a modified pressure bearing pellet tool, and differs from the modified pressure balanced pellet tool of FIGS. 28-30 in that the modified pressure bearing pellet tool 600' includes a housing 610 having an internal bore 611, in which the guide tube 616 and explosive pellets 640 are provided. The internal bore 611 can be sealed at its lower end by a bottom nose 614. The interior face of the bottom nose 614 can be cushioned with a resilient padding 615, such as a silicon foam washer. In other respects, the modified pressure bearing pellet tool 600' is similar to the modified pressure balanced pellet tool 600, and so like components are similarly labeled in FIGS. 31-33.

A method of selectively expanding at least a portion of the wall of a pipe or other tubular using the expansion tool described herein may be as follows. The expansion tool may be either the modified pressure balanced tool 600 of FIGS. 28-30, or the modified pressure bearing tool 600' of FIGS. 31-33. The expansion tool is assembled by arranging a predetermined number of explosive pellets 640 on the guide tube 616, which can to be in a serially-arranged column between the second and third bi-directional boosters 628, 626, so that the explosive pellets 640 are exposed to an outside of the expansion tool. The expansion tool is then positioned within a tubular T1 that is to be expanded, as shown in FIG. 34A.

Figure 34A:
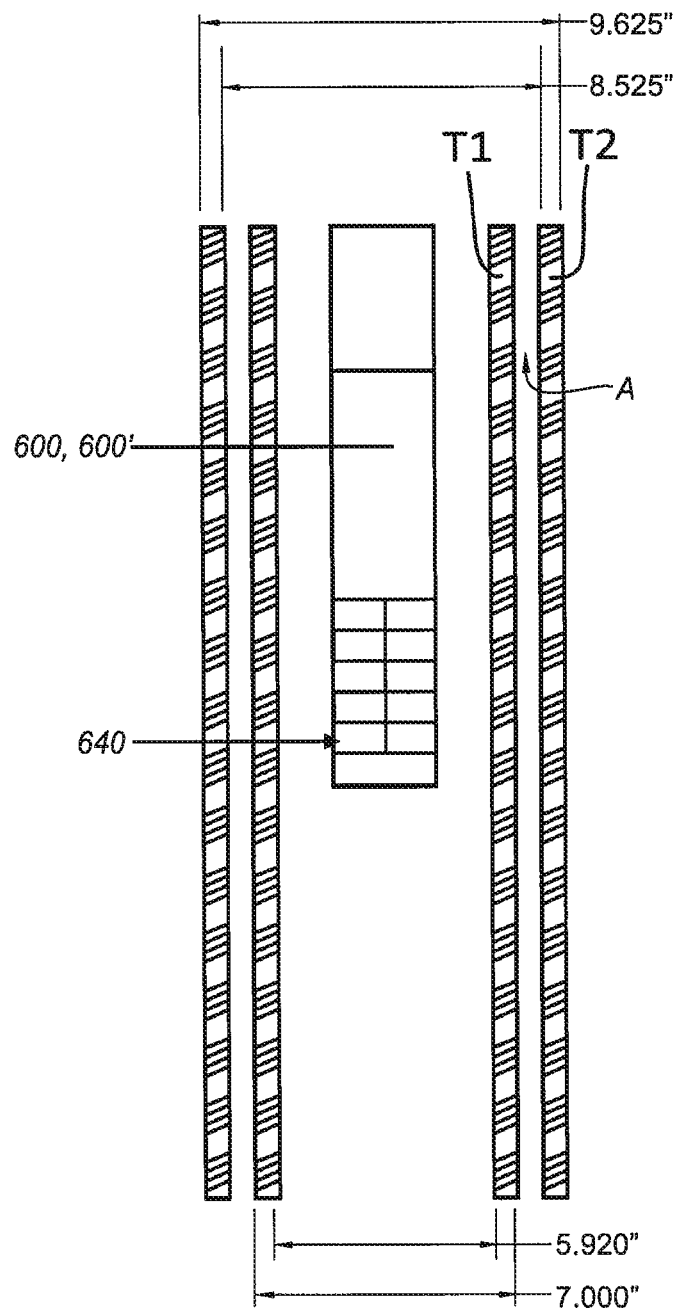
FIGS. 34A to 34C illustrate a method of selectively expanding at least a portion of the wall of a tubular using the dual end firing explosive column tool.
Figure 34B:
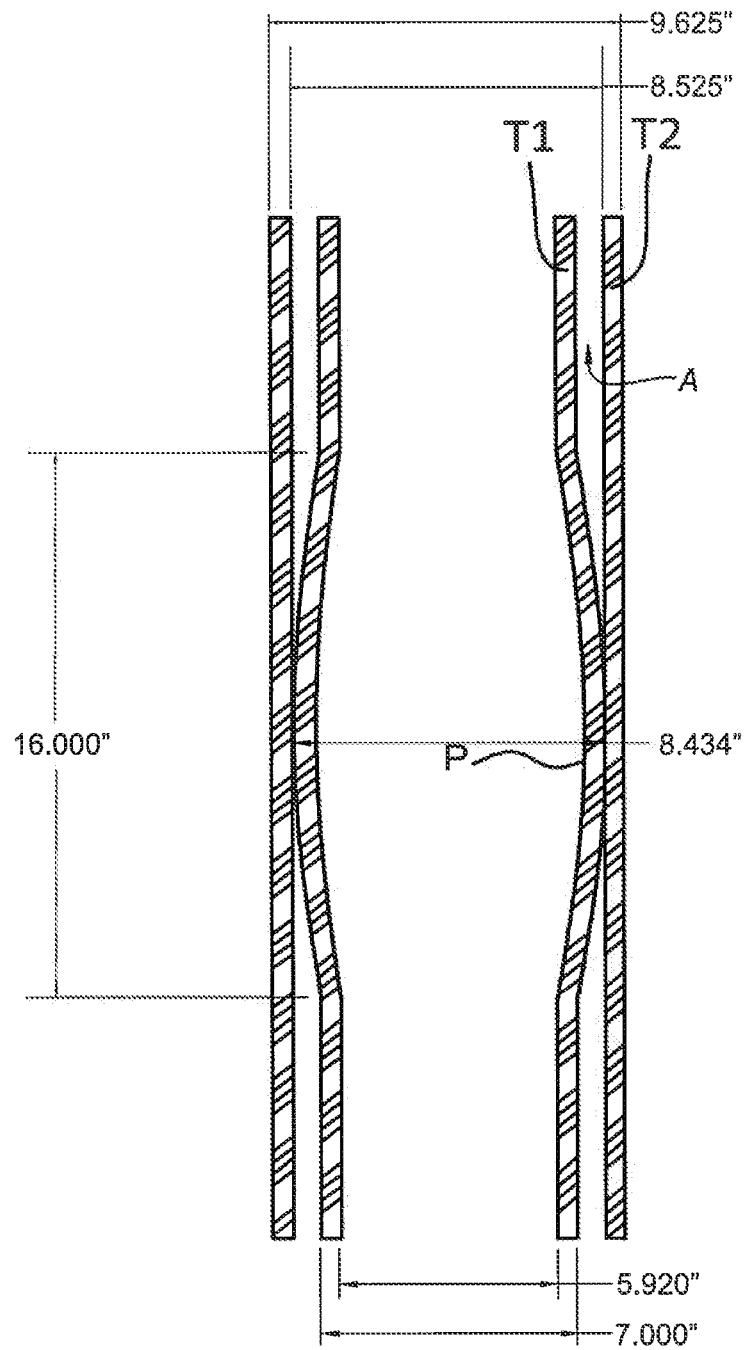
Figure 34C:
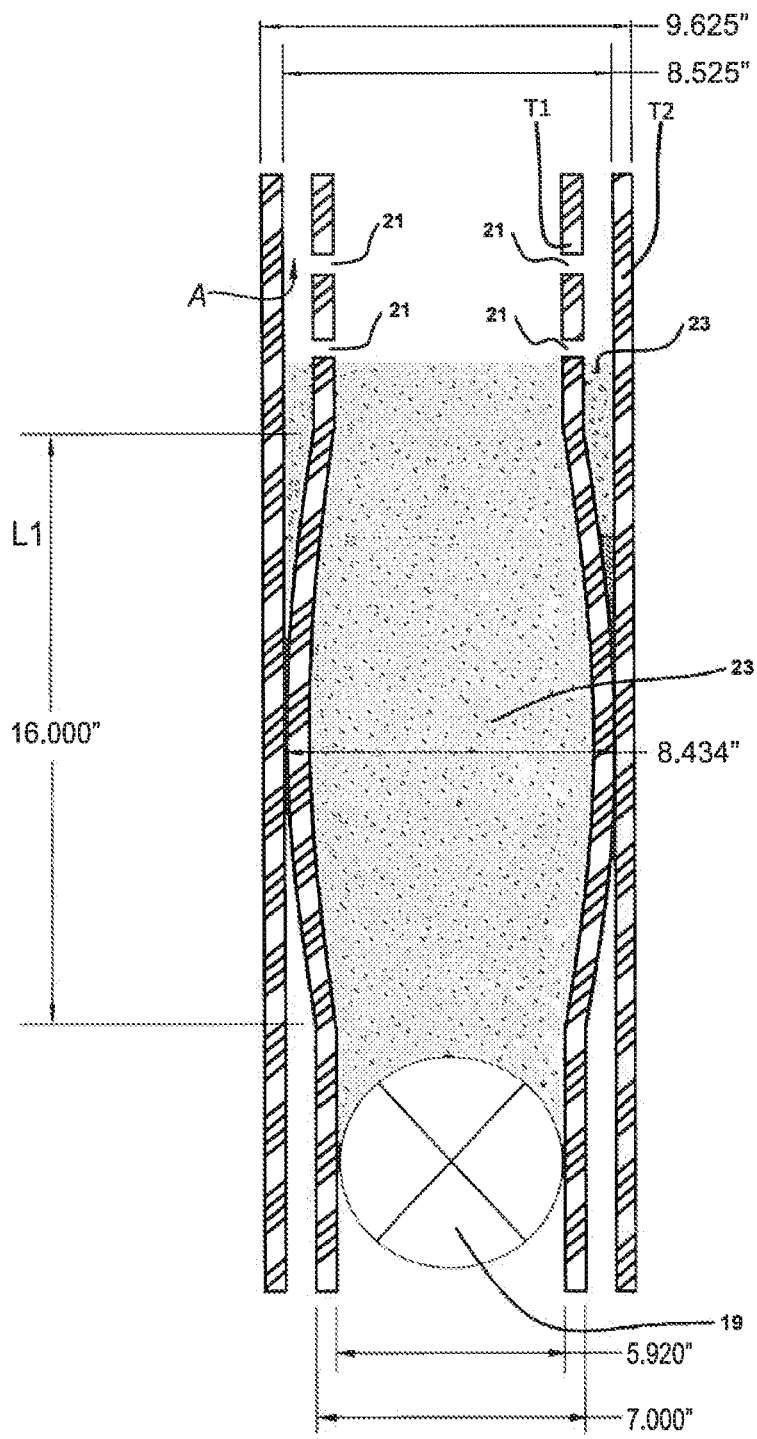

As shown in FIG. 34A, the tubular T1 may be an inner tubular that is located within an outer tubular T2, such that an annulus "A" is formed between the outer diameter of the inner tubular T1 and the inner diameter of the outer tubular T2. In some cases, the annulus "A" may contain material, such as cement, barite, other sealing materials, mud and/or debris. In other cases, the annulus "A" may not have any material therein. When the expansion tool 600, 600' reaches the desired location in the tubular T1, the bi-directional boosters 624, 626, 628 are detonated to simultaneously ignite opposing ends of the serially-arranged column of pellets 640 to form two shock waves that collide to create an amplified shock wave that travels radially outward to impact the inner tubular T1 at a first location, and expand at least a portion of the wall of the tubular T1 radially outward, as shown in FIG. 348, without perforating or cutting through the portion of the wall, to form a protrusion "P" of the tubular T1 at the portion of the wall. The protrusion "P" extends into the annulus "A" between an outer surface of the wall of the inner tubular T1 and an inner surface of a wall of the outer tubular T2. Note that the pipe dimensions shown in FIGS. 34A to 34C are exemplary and for context, and are not limiting to the scope of the invention.

The protrusion "P" may impact the inner wall of outer tubular T2 after detonation of the explosive pellets 640. In some embodiments, the protrusion "P" may maintain contact with the inner wall of the outer tubular T2 after expansion is completed. In other embodiments, there may be a small space between the protrusion "P" and the inner wall of the outer tubular T2. Expansion of the tubular T1 at the protrusion "P" can cause that portion of the wall of the tubular T1 to be work-hardened, resulting in greater strength of the wall at the protrusion "P". Embodiments of the methods of the present invention show that the portion of the wall having the protrusion "P" is not weakened. In particular, the yield strength of the tubular T1 increases at the protrusion "P", while the tensile strength of the tubular T1 at the protrusion "P" decreases only nominally. Therefore, according to these embodiments, expansion of the tubular T1 at the protrusion "P" thus strengthens the tubular without breaching the tubular T1.

The magnitude of the protrusion "P" can depend on several factors, including the length of the column of explosive pellets 640, the outer diameter of the explosive pellets 640, the amount of explosive material in the explosive pellets 640, the type of explosive material, the strength of the tubular T1, the thickness of the wall of the tubular T1, the hydrostatic force bearing on the tubular T1, and the clearance adjacent the tubular T1 being expanded, i.e., the width of the annulus "A" adjacent the tubular T1 that is to be expanded.

One way to manipulate the magnitude of the protrusion "P" is to control the amount of explosive force acting on the pipe or other tubular member T1. This can be done by changing the number of pellets 640 aligned along the guide tube 616. For instance, the explosive force resulting from the ignition of a total of ten pellets 640 is larger than the explosive force resulting from the ignition of a total of five similar pellets 640. As discussed above, the length "L1" (see FIG. 34C) of the expansion of the wall of the tubular T1 may be about two times the length of the column of explosive pellets 640. Another way to manipulate the magnitude of the protrusion "P" is to use pellets 640 with different outside diameters. The expansion tool discussed herein can be used with a variety of different numbers of pellets 640 in order to suitably expand the wall of pipes or other tubular members of different sizes. Determining a suitable amount of explosive force (e.g., the number of pellets 640 to be serially arranged on the guide tube 616), to expand the wall of a given tubular T1 in a controlled manner, can depend on a variety of factors, including: the length of the column of explosive pellets 640, the outer diameter of the explosive pellets 640, the material of the tubular T1, the thickness of a wall of the tubular T1, the inner diameter of the tubular T1, the outer diameter of the tubular T1, the hydrostatic force bearing on the tubular T1, the type of the explosive (e.g., HMX, HNS) and the desired size of the protrusion "P" to be formed in the wall of the tubular T1.

The above method of selectively expanding at least a portion of a wall of the tubular T1 via an expansion tool may be modified to include determining the following characteristics of the tubular T1: a material of the tubular T1; a thickness of a wall of the tubular T1; an inner diameter of the tubular T1; an outer diameter of the tubular T1; a hydrostatic force bearing on the tubular T1; and a size of a protrusion "P" to be formed in the wall of the tubular T1. Next, the explosive force necessary to expand, without puncturing, the wall of the tubular T1 to form the protrusion "P", is calculated, or determined via testing, based on the above determined material characteristics.

The determinations and calculation of the explosive force can be performed via a software program, and providing input, which can then be executed on a computer. Physical hydrostatic testing of the explosive expansion charges yields data which may be input to develop computer models. The computer implements a central processing unit (CPU) to execute steps of the program. The program may be recorded on a computer-readable recording medium, such as a CD-ROM, or temporary storage device that is removably attached to the computer. Alternatively, the software program may be downloaded from a remote server and stored internally on a memory device inside the computer. Based on the necessary force, a requisite number of explosive pellets 640 to be serially added to the guide tube 616 of the expansion tool is determined. The requisite number of explosive pellets 640 can be determined via the software program discussed above.

The requisite number of explosive pellets 640 is then serially added to the guide tube 616. After loading, the loaded expansion tool can be positioned within the tubular T1, with the last pellet 640 in the column being located adjacent the detonation window 634. Next, the expansion tool can be actuated to ignite the pellets 640, resulting in a shock wave as discussed above that expands the wall of the tubular T1 radially outward, without perforating or cutting through the wall, to form the protrusion "P". The protrusion "P" can extend into the annulus "A" between an outer surface of the tubular T1 and an inner surface of a wall of another tubular T2.

In a test conducted by the inventors using the dual end firing explosive column tool 600 to radially expand a pipe having a 6.4 centimeter (2.5 inch) wall thickness, an inner diameter of 22.9 centimeters (9.0 inches) and an outer diameter of 35.6 centimeters (14.0 inches), the expansion resulted in a radial protrusion measuring 45.7 centimeters (18.0 inches) in diameter. That is, the outer diameter of the pipe increased from 35.6 centimeters (14.0 inches) to 45.7 centimeters (18.0 inches) at the protrusion. The protrusion is a gradual expansion of the wall of the tubular T1. The more gradual expansion allows a greater expansion of the tubular T1 prior to exceeding the elastic strength of the tubular T1, and failure of the tubular T1 (i.e., the tubular being breeched).

The column of explosive pellets 640 can comprise a predetermined (or requisite) amount of explosive material sufficient to expand at least a portion of the wall of the pipe or other tubular into a protrusion extending outward into an annulus adjacent the wall of the pipe or other tubular. It is important to note that the expansion can be a controlled outward expansion of the wall of the pipe or other tubular, which does not cause puncturing, breaching, penetrating or severing of the wall of the pipe or other tubular. The annulus may be reduced between an outer surface of the wall of the pipe or other tubular and an outer wall of another tubular or a formation.

The protrusion "P" creates a ledge or barrier into the annulus that helps seal that portion of the wellbore during plug and abandonment operations in an oil well. For instance, a sealant, such as cement or other sealing material, mud and/or debris, may exist in the annulus "A" on the ledge or barrier created by the protrusion "P". The embodiments above involve using one column of explosive pellets 640 to selectively expand a portion of a wall of a tubular into the annulus. One option is to use two or more columns of explosive pellets 640. The explosive columns may be spaced at respective expansion lengths which, as noted previously, can vary as a function of the length of the explosive column unique to each application. After the first protrusion is formed by the first explosive column, the additional explosive column is detonated at a desired location, to expand the wall of the tubular T1 at a second location that is spaced from the first location and in a direction parallel to an axis of the expansion tool, to create a pocket outside the tubular T1 between the first and second locations. The pocket is thus created by sequential detonations of explosive columns. In another embodiment, the pocket may be formed by simultaneous detonations of explosive columns. For instance, two explosive columns may be spaced from each other at First and second locations, respectively, along the length of the tubular T1. The two explosive columns are detonated simultaneously at the first and second locations to expand the wall of the tubular T1 at the first and second locations to create the pocket outside the tubular T1, between the first and second locations.

Whether one or multiple columns of explosive pellets 640 are utilized, the method may further include setting a plug 19 below the deepest selective expansion zone, and then shooting perforating puncher charges through the wall of the inner tubular T1 above the top of the shallowest expansion zone, so that there can be communication ports 21 from the inner diameter of the inner tubular T1 to the annulus "A" between the inner tubular T1 and the outer tubular T2, as shown in FIG. 34C. Cement 23, or other sealing material, may then be pumped to create a seal in the inner diameter of the inner tubular T1 and in the annulus "A" through the communication ports 21 between the inner tubular T1 and the outer tubular T2, as shown in FIG. 34C. The cement 23 is viscus enough that, even if there is only a ledge/restriction (formed by the protrusion P1), the cement 23 should be slowed down long enough to set up and seal. When the cement 23 is pumped into the annulus "A", any and all material, (e.g., cement, mud, debris), will likely help effect the seal. One reason multiple columns of explosive pellets 640 may be used is the hope that if a seal is not achieved in the annulus "A" at the first ledge/restriction (formed by the protrusion P1), the seal may be provided by the additional ledge/restriction (formed by the additional protrusion). If the seal in the annulus "A" cannot be effected, the operator must cut the inner tubular T1 and retrieve it to the surface, and then go through the same plug and pump cement procedure for the outer tubular T2. Those procedures can be expensive.

The methods discussed herein have involved selectively expanding a wall of tubular while the tubular is inside of a wellbore. A variation of the embodiments discussed herein includes a method of selectively expanding a wall of tubular outside of the wellbore before the tubular is inserted into the wellbore. This variation may be carried out with the various expansion tools discussed herein. The various expansion tools discussed herein can be used to selectively expand the wall of tubular outside of the wellbore. The amount of explosive material used in this variation may be based upon the physical aspects of the tubular, the nature and conditions of the wellbore in which the tubular will subsequently be inserted, and upon the type of function the selectively expanded tubular is to perform in the wellbore. The selective expansion of the tubular may occur, for example, at a facility offsite from the location of the actual wellbore. The selectively expanded tubular may be inspected to confirm dimensional aspects of the expanded tubular, and then be transported to the wellsite for insertion into the wellbore. For instance, a method of selectively expanding a wall of a tubular may involve positioning an expansion tool within the tubular, wherein the expansion tool contains an amount of explosive material for producing an explosive force sufficient to expand, without puncturing, the wall of the tubular. Next, the expansion tool may be actuated to expand the wall of the tubular radially outward, without perforating or cutting through the wall of the tubular, to form a protrusion that extends outward from the central bore of the tubular. The selectively expanded tubular may then be subsequently inserted into a wellbore.

Because wellbore conditions and the physical properties of the tubular within the wellbore vary from wellbore to wellbore, it may be desirable to tailor the physical or compositional make-up (e.g., type, amount, size) of an expansion charge to the specific tubular and conditions in the wellbore at which the expansion charge is to be used. Pre-testing expansion charges to be deployed based on the specific conditions that exist in a wellbore and/or physical properties of the tubular in the wellbore is helpful to ensure beforehand that the expansion charge will provide an adequate or desired wall expansion (e.g., protrusion) of the wellbore tubular, without perforating or cutting through, when the expansion charge is actuated in the wellbore.

FIGS. 35A-35D illustrate systems for pre-testing an expansion charge on a test tubular 704 according to some embodiments. Each system may be situated at a location other than the actual wellbore in the field. For instance, the systems may be provided at a test facility. FIG. 35A shows a pre-testing system 700 that includes a cylindrically-shaped pressure vessel 701. In an exemplary embodiment, the pressure vessel 701 may be 14 inch outer diameter, 9 inch inner diameter, 10 foot long P110 tubular. A bottom end of the pressure vessel 701 may include a cushion element 702, and a bottom high pressure head 706 as illustrated in FIG. 35A. The cushion element 702 may help protect the bottom of a junk basket 703 (discussed below), and may be a 2.5 inch solid rubber disc according to one embodiment. Other types of plugs may be used to plug the pressure vessel 701. The top end of the pressure vessel 701 may include an upper high pressure head 707 that includes a high pressure autoclave port 707A and a fluid-to-air connector 707B. The high pressure autoclave port 707A receives a high pressure hose 708 that is connected to an autoclave high pressure pump 709 for pressurizing the pressure vessel 701. The high pressure hose 708 may have a rating of 60,000 psi. A junk basket 703 may be provided within the pressure vessel 701 to contain debris after testing is completed. A test tubular 704 may be inserted into the pressure vessel 701 to be centrally positioned mid-vessel and within the junk basket 703. An expansion charge 705 of an expansion charge tool (not shown) may be inserted into the test tubular 704 that is within the pressure vessel 701, and may be positioned centrally in the middle of the test tubular 704. In some embodiments, the expansion charge 705 may be positioned to be decentralized in the test tubular 704 if centralization is not possible, or if decentralization is desired. The pre-testing system 700 may be used to test whether the expansion charge 705 will sufficiently expand, without perforating or cutting through, the wall of the test tubular 704 before a similar expansion charge 705 is used to selectively expand the wall of a tubular in a wellbore in the field.

In this regard, the pre-testing system 700 may be used to simulate or reproduce conditions that exist in the onsite wellbore, namely the hydrostatic pressure and the fluid/gas medium present, so that the tested expansion charge 705 can be designed and manufactured to have a similar or the same effect when used on a tubular in the onsite wellbore. For instance, the pressure vessel 701 may be filled with air, water, nitrogen, drilling fluid, completion fluid, acidizing fluid, salt water, and/or fresh water to match or represent the environment (e.g., air, water, nitrogen, drilling fluid, completion fluid, acidizing fluid, salt water, and/or fresh water) that exists in onsite wellbore. The autoclave high pressure pump 709 may then pressurize the pressure vessel 701 (e.g., using the same material) to a hydrostatic pressure that exists at a depth in the onsite wellbore where the wall of the wellbore tubular is to be expanded. In addition, the physical characteristics the test tubular 704 may, in some cases, be the same or similar to those of the actual tubular in the onsite wellbore. In a preferred embodiment, a new tubular having the same or similar physical characteristics, such as material type, size, grade, weight, wall thickness, outer diameter, and inner diameter, to the actual tubular in the onsite wellbore may be used as the test tubular 704. As an example, test tubular 704 may be a 5.5 inch outer diameter, 0.244 inch thick, 14.0 ppf, J-55 tubular. In addition, the pre-testing system 700 may be used under conditions that are transferrable to a downhole application. For instance, pre-testing in a pressure vessel 701 or in a water tank or open water with different conditions than exist downhole in the onsite wellbore can produce results that, with manipulation to the design of the expansion charge 705 or other conditions based on the test results, can transferred to the downhole application. That is, the manipulated expansion charge or other conditions can have the same or similar effect, or other desired effect, when used on a tubular in the onsite wellbore of the downhole application.

The pre-testing system 700 illustrated in FIG. 35A may be characterized as an "unconfined" system because the outer surface of the test tubular 704 is exposed to the fluid/gas medium within the pressure vessel 701, rather than being encased in cement, sand, another solid material, and/or another tubular, in the pressure vessel 701. In an embodiment, an as-new tubular as the test tubular 704 is tested in an "unconfined" system as a safety factor against breaching the actual tubular in the onsite wellbore. If the expansion charge 705 does not rupture the as-new test tubular 704 in the "unconfined" system (i.e., with no confinement), then the same expansion charge 705 should not rupture the actual tubular which has some confinement in the onsite wellbore (e.g., confinement by cement, sand, another material, and/or another tubular, in the onsite wellbore). This is especially the case if the mechanical properties of the actual tubular in the onsite wellbore have not been significantly reduced by corrosion, etc. In addition, if the expansion charge does not rupture the test tubular that is at zero or relatively low pressure, then the same expansion charge should not rupture the actual tubular in the wellbore that is subject to relatively large pressure.

FIG. 35B illustrates an example of a "confined" pre-testing system 700A. The "confined" pre-testing system 700A differs from the "unconfined" pre-testing system 700 in that the test tubular 704 is encased in the pressure vessel 701 with a material 710 such as cement, sand, or other material that encases the actual tubular in the onsite wellbore. Further, the material 710 may be surrounded by a second tubular 711 to simulate or represent conditions of the material 710 in the onsite wellbore. In an embodiment, the material 710 may be Portland Cement having a 100/44 cement to water ratio or another ratio. However, a material other than Portland Cement can be used to confine the test tubular 704. Moreover, the test tubular 704 can be confined 100% or less as required to simulate or represent downhole wellbore conditions. In the embodiment of FIG. 35B, the test tubular 704 may be a 3.5 inch outer diameter, 0.254 inch thick, 9.2 ppf, L-80 tubular that is 4 feet long. The second tubular 711 may be a 7.0 inch outer diameter, 0.237 inch thick, 26 ppf, L-80 tubular that is 4 feet long. However, the test tubular 704 and the second tubular 711 may have different sizes than discussed above as needed to better represent conditions in the onsite wellbore. The "confined" pre-testing system 700A may be used when it is determined that the "unconfined" test is radically different than the actual downhole environment (i.e., the fluid/gas medium downhole). In another embodiment, the "confined" pre-testing system 700A may be used when the pressure acting on the tubular in the onsite wellbore is less than or equal to 5000 psi. This may be the case for onsite wellbores having a gaseous environment, such a nitrogen, or gases having a similar atomic weight as nitrogen. In a further embodiment, the "confined" pre-testing system 700A may be used to determine how much explosive material is needed to close one or more channels that exist in a cemented annulus adjacent the tubular in the onsite wellbore. This may be the case in, for example, in a highly deviated or horizontal well, in which gravity prevents adequate cement flow at the top portion of the horizontal annulus. The lack of adequate cement flow may result in formation of a channel in the cement at the top portion.

FIG. 35C shows an embodiment of an "unconfined" pre-testing system 700 in which multiple expansion charges 705 are tested on the test tubular 704 simultaneously or sequentially, for jobs in which more than one expansion charge (or explosive units 60) are to be used as discussed herein (see, e.g., FIGS. 2G to 2I). FIG. 35D shows an embodiment of a "confined" pre-testing system 700A in which multiple expansion charges 705 are tested on the test tubular 704 simultaneously or sequentially, for jobs in which more than one expansion charge (or explosive units 60) are to be used as discussed herein (see, e.g., FIGS. 2G to 2I).

The pre-testing systems 700, 700A discussed above may be used to implement a method of determining an expansion charge able to selectively expand, without perforating or cutting through, a portion of a wall of a tubular in an onsite wellbore. The method may include determining conditions in the onsite wellbore. The conditions may include, among other things, the fluid/gas medium in the wellbore, hydrostatic pressure bearing on the tubular in the onsite wellbore, and at least one physical characteristic of the tubular. For instance, the method may include determining whether the fluid/gas medium in the onsite wellbore comprises air, water, nitrogen, drilling fluid, completion fluid, acidizing fluid, salt water, fresh water and/or combinations thereof. The determined conditions may be reproduced, simulated, accounted for, or otherwise factored into the pre-testing systems 700, 700A discussed herein. As an example, if the fluid/gas medium in the onsite wellbore includes acidizing fluid, then the pressure vessel 701 may be filled with acidizing fluid to help simulate in the pressure vessel 701 the conditions existing in the onsite wellbore. Physical characteristics of the tubular in the onsite wellbore that may be determined can include the material of the tubular, the grade, the weight, the inner diameter, and the outer diameter. The test tubular 704 in the pre-testing systems 700, 700A may have the same or similar physical characteristics as the actual tubular in the onsite wellbore, and may be new. In some embodiments, the test tubular 704 in the pre-testing systems 700, 700A may be a used tubular from the onsite wellbore, if available. As discussed above, using a new tubular in the "unconfined" testing system 700 may serve as a safety factor against breaching the actual tubular in the onsite wellbore because if the expansion charge 705 does not rupture the new test tubular 704, then the same expansion charge 705 should not rupture the actual tubular in the onsite wellbore, which actual tubular will likely have at least some confinement (or greater pressure), so long as the mechanical properties of the actual tubular are not significantly reduced by corrosion, etc.

When the pressure acting on the tubular in the onsite wellbore is relatively low, for example, less than or equal to 5000 psi, the method may involve providing the test tubular 704 in the "confined" pre-testing system 700A configuration discussed above. This may be the case for onsite wellbores having a gaseous environment, such a nitrogen, or gases having a similar atomic weight as nitrogen. As discussed above, the test tubular 704 in the "confined" pre-testing system 700A may be encased in the pressure vessel 701 with a material 710 such as cement, sand, or other material that encases the actual tubular in the onsite wellbore. That is, the annulus adjacent an outer surface of the test tubular 704 contains a solid material, such as cement, sand, or other material that encases the actual tubular in the onsite wellbore. Further, the material 710 may be surrounded by a second tubular 711 as discussed above. When the pressure acting on the tubular in the onsite wellbore is greater than 5000 psi, the method may involve providing the test tubular 704 in the "unconfined" pre-testing system 700 configuration discussed above. In that case, the test tubular 704 may be unconfined such that the outer surface of the test tubular 704 is exposed to the fluid/gas medium within the pressure vessel 701. That is, the annulus adjacent the outer surface of the test tubular 704 contains no solid material, rather than being encased in cement, sand, another solid material, and/or another tubular, in the pressure vessel 701.

In some cases, the method may include determining beforehand the size of a protrusion to be formed in the wall of the tubular in the onsite wellbore. This determination may be based on the type of the onsite wellbore and/or the oilfield job (e.g., plug and abandon) to be performed on tubular in the onsite wellbore. Knowing beforehand the size of the protrusion to be formed in the wall of the tubular may help determine the size, explosive gram weight, material, and/or other physical characteristic discussed herein of the expansion charge 705 to be used in the pre-testing systems 700, 700A, and eventually in the tubular of the onsite wellbore. For instance, relatively larger protrusions may require a relatively larger size and higher explosive gram weight expansion charge. The expansion charge 705 may be a shaped charge for use in a shaped charged expansion tool, and may comprise embodiments of the shaped charges discussed herein. For relatively larger tubulars (i.e., having thicker walls), and/or multiple nested pipes, a dual-end firing explosive column tool may be used.

The method further includes determining a test expansion charge 705 that is able to expand, without perforating or cutting through, the wall of the test tubular 704, based on at least one of the conditions determined in the wellbore. In some embodiments, determining a test expansion charge 705 may include determining a size and an explosive gram weight of test expansion charge 705 that is able to expand, without perforating or cutting through, the wall of the test tubular 704. Determining a test expansion charge 705 may also include determining a shape, or other characteristic of expansion charges discussed herein. In some embodiments, these determinations may be made based on tests, or a history of tests, that are conducted in trial-and-error processes. For instance, a record of tests (such as Tests #1 to #16 discussed below) can be stored in a library of test data used to forecast or predict expansion results. The record may include test results that are organized and/or retrievable according to wellbore type, wellbore conditions, oilfield job type, tubular size and type, expansion charge type, expansion charge size, expansion charge explosive gram weight, type of explosive material, and other characteristic discussed herein. The test expansion charge 705 may be determined by reviewing the library of test data and focusing on a test result having one or more similar conditions (e.g., with respect to the fluid/gas medium in the wellbore, hydraulic pressure in the wellbore, and physical characteristics of the tubular in the wellbore, among other conditions discussed herein) as the onsite wellbore for which the test expansion charge 705 is being designed.

Once the test expansion charge 705 is determined, the test expansion charge 705 may be positioned within the test tubular 704 in the pressure vessel 701. The test expansion charge 705 is then actuated, in a manner discussed herein, to expand the wall of the test tubular 704 radially outward, without perforating or cutting through the wall of the test tubular 704, to form a test protrusion in the wall of the test tubular 704. Depending on the size, shape or other physical characteristic of the test protrusion, the test expansion charge 705 may be selected as the expansion charge for expanding, without perforating or cutting through, the portion of the wall of the actual tubular in the onsite wellbore. Or, if the size, shape or other physical characteristic of the test protrusion was determined to be a failure (e.g., a breach of the tubular on one hand or not enough expansion on the other hand), a different expansion charge may be selected for expanding, without perforating or cutting through, the portion of the wall of the actual tubular in the onsite wellbore. As discussed above, the test expansion charge 705 may be selected based on a particular size and/or explosive gram weight of the test expansion charge 705, or on another characteristic of the test expansion charge 705 evident from testing the test expansion charge. In some embodiments, a particular size and/or explosive gram weight for the actual expansion charged used to expand the actual tubular in the onsite wellbore may be selected based on the performance of the test expansion charge 705. The methods discussed above may further include, using the principles discussed above, determining a test expansion charge 705 that is able to expand, without perforating or cutting through, both the wall of the test tubular 704 and the wall of the second tubular 711, with a single actuation of the test expansion charge 705, to provided nested protrusions as discussed with respect to FIGS. 2M to 2P above.

The following describes some tests that were conducted by the inventor to determine an expansion charge able to expand, without perforating or cutting through, the wall of a particular tubular. Specifically, Tests #1 to #16 were conducted to determine the size (e.g., outer diameter, "O.D.") and explosive gram weight required in an expansion charge to expand a 3.5 inch O.D., 9.20 ppf, L-80 tubular to the targeted diameter of 4.000 inch in different environments (e.g. air, water, nitrogen). The sizes (O.D.) and explosive gram weights of the expansion charges that were tested were: (a) 2.188 inch O.D.; 34-50 grams HMX; and (b) 2.125 inch O.D.; 22-40 grams HMX. The target expansion diameter for the 3.5 inch O.D. tubular was 0.25 inches on the radius. The tests were conducted in ambient temperature. A 10 foot pressure vessel and a 42 inch pressure vessel were used in the tests. The set up for each pressure vessel was as follows:

The 10 foot pressure vessel: (a) 14 inch O.D.×9 inch I.D.×10 foot long, P110 pressure vessel; (b) 3.5 inch O.D.× 0.254 inch wall thickness. 9.2 ppf, L-80 target tubular, 4 foot long positioned mid vessel and centralized; (c) 2.188 inch or 2.125 inch expansion charge centralized in the middle of the 3.5 inch O.D. tubular; (d) 102 inch working length inside the of the pressure vessel; and (e) junk baskets that were (i) 8⅝ inch O.D.×8 inch I.D.×8 feet long; and (ii) 8-⅝ inch O.D.×6 inch I.D.×8 feet long.

The 42 inch pressure vessel: (a) 14 inch O.D.×9 inch I.D.×42 inch long, P110 pressure vessel; (b) 3.5 inch O.D.× 0.254 inch wall thickness, 9.2 ppf, L-80 target tubular, 24 inches long positioned mid vessel and centralized; (c) 2.125 inch expansion charge centralized in the middle of the 3.5 inch O.D. tubular; (d) 24 inch working length inside the vessel; and (e) junk baskets that were (iii) 8⅝ inch O.D.×6 inch I.D.×24 inches long; and (iv) 8⅝ inch O.D.×4½ inch I.D.×24 inches long.

To begin with, three pre-tests were conducted at 0 psi in a spent 14 inch O.D.×9 inch I.D.×10 foot long pressure vessel with a 2.188 inch expansion charge, with the following results.

TABLE 3

| Wall Thickness (in) | Test # | Explosive Subassembly | Explosive Gram Weight | Housing O.D. (in) | Expansion Diameter (in) | Target Length (in) | PSI | Atmosphere | Junk Basket |
|---|---|---|---|---|---|---|---|---|---|
| 0.254 | 1 | 2188TEXP | 50 | 2.188 | Failed | 48 | 0 | Water | (i) |
| 0.254 | 2 | 2188TEXP | 34 | 2.188 | 4.196 | 48 | 0 | Water | (i) |
| 0.254 | 3 | 2188TEXP | 34 | 2.188 | Failed | 48 | 0 | Air | (ii) |

The results of these tests show that at 0 psi in water (Test #2), the test tubular was expanded to 4.196 inches O.D. In addition, the 14 inch×9 inch×10 foot long reusable vessel can be used to conduct the 1.000 psi nitrogen test, as the vessel stayed intact during Test #3 (0 psi in air). Test #3 showed that the 34 gram, 2.188 inch expansion charge breached (i.e., split) the tubular such that the expansion "failed". Loading a smaller expansion charge, for example, a 2.125 inch expansion, with 18 grams to 22 grams of explosive, instead of 34 grams, may reach the target expansion at 1,000 psi in nitrogen. Further tests were conducted to optimize the expansion in air at 0 psi with a 2.125 inch expansion charge and different explosive gram weights.

TABLE 4

| Wall Thickness (in) | Test # | Explosive Subassembly | Explosive Gram Weight | Housing O.D. (in) | Expansion Diameter (in) | Target Length (in) | PSI | Atmosphere | Junk Basket |
|---|---|---|---|---|---|---|---|---|---|
| 0.254 | 4 | 2125TEXP | 22 | 2.125 | 3.514 | 48 | 0 | Air | (ii) |
| 0.254 | 5 | 2125TEXP | 26 | 2.125 | Failed | 48 | 0 | Air | (ii) |
| 0.254 | 6 | 2125TEXP | 24 | 2.125 | 3.883 | 48 | 0 | Air | (ii) |
| 0.254 | 7 | 2125TEXP | 25 | 2.125 | Failed | 48 | 0 | Air | (ii) |

These test results show that the 3.838 inch O.D. expansion in air at 0 psi is not far from the 4.000 inch expansion target, but not so close to the 4.196 inch O.D. expansion achieved when tested in water at 0 psi. It is noted that water as the atmosphere offers some confinement and would slow down the speed of the pressure wave front of the expansion charge. More tests were conducted, this time with a nitrogen atmosphere at 1,000 psi and with a 24 gram expansion charge, with the following results.

TABLE 5

| Wall Thickness (in) | Test # | Explosive Subassembly | Explosive Gram Weight | Housing O.D. (in) | Expansion Diameter (in) | Target Length (in) | PSI | Atmosphere | Junk Basket |
|---|---|---|---|---|---|---|---|---|---|
| 0.254 | 8 | 2125TEXP | 24 | 2.125 | Failed | 24 | 1000 | Nitrogen | (iii) |
| 0.254 | 9 | 2125TEXP | 24 | 2.125 | 3.887 | 48 | 1000 | Nitrogen | (ii) |
| 0.254 | 10 | 2125TEXP | 24 | 2.125 | Failed | 24 | 1000 | Nitrogen | (iv) |
| 0.254 | 11 | 2125TEXP | 25 | 2.125 | Failed | 48 | 1000 | Nitrogen | (ii) |

Test #8 was conducted in the shorter 42 inch pressure vessel in order to minimize the volume of nitrogen, and the expansion failed. Test #9 was conducted in the 10 foot pressure vessel, and the expansion was similar to the expansion in Test #6 in air at 0 psi. Test #10 was conducted in the 42 inch pressure vessel with a 4.5 inch I.D. junk basket, and the expansion also failed. In Test #11, the 25 gram weight expansion charge failed in nitrogen at 0 psi.

Tests #12 to #16 were conducted with the 3¾ inch target tubular cemented, with Portland cement (100/44 cement to water ratio), inside of 7 inch O.D.×6.526 inch I.D.×4 foot long. 26 ppf. L-80 tubular. No significant voids existed in the cement as the 4 foot targets were poured in the vertical position. After the test shots the 7 inch O.D. outer tubular was cut off with a torch to retrieve the 3½" O.D. tubular for measurements. After the test shots, the 7 inch O.D. outer tubular showed no expansion. On each end the cement in the annulus had extruded around ⅛ inches.

The above described test procedures and processes may be helpful in determining beforehand, based on the specific conditions that exist in a wellbore and/or physical properties of the tubular set in the onsite wellbore, a specific expansion charge that is to be used on the tubular in that onsite wellbore. A specific expansion charge can be designed based on those conditions to ensure that the expansion charge sufficiently expands, without perforating or cutting through, the wall of the tubular in the onsite wellbore. As the actual conditions determined in the onsite wellbore can be simulated, reproduced, factored in, or otherwise accounted for, the above-described pre-testing may help ensure that the expansion charge provides an adequate or desired wall expansion (e.g., protrusion) of the wellbore tubular when the expansion charge is actuated in the onsite wellbore.

The pre-testing discussed above with respect to FIGS. 35A to 35D involved positioning the test tubular 704 inside of a pressure vessel 701 to determine the maximum explosive load that can be used to generate the largest outer diameter expansion without breaching the tubular. To reduce costs and the amount of resources associated with testing inside of the pressure vessel 701, as well any anomalous effects of simulated testing within a sealed vessel which may skew actual results downhole in the wellbore, a tubular may be tested in an open tank or in an open body of water. Typically, when there is a need to expand relatively heavy wall pipe, larger diameter pipes, and multiple pipes cemented together, the hydrostatic pressures downhole are relatively low, e.g., 2,000 psi or less. Testing in an open water tank at 0 psi may reflect a similar expansion to what one might expect in the downhole application. Under hydro-

TABLE 6

Figures 36A, 36B:
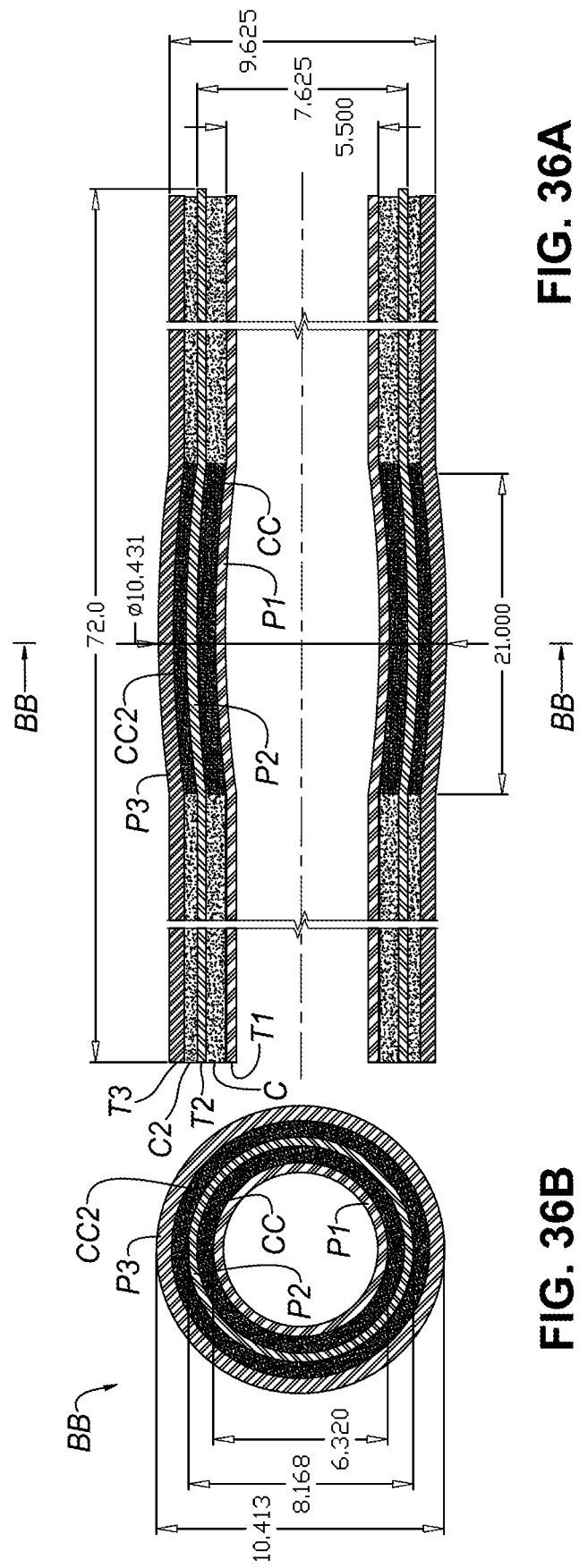
FIGS. 36A and 36B illustrate the results of a pre-test on nested tubulars in an open tank according to an embodiment.

| Wall Thickness (in) | Test # | Explosive Subassembly | Explosive Gram Weight | Housing O.D. (in) | Expansion Diameter (in) | Target Length (in) | PSI | Atmosphere | Junk Basket |
|---|---|---|---|---|---|---|---|---|---|
| 0.254 | 12 | 2188TEXP | 34 | 2.188 | 4.000 | 48 | 0 | Water | (i) |
| 0.254 | 13 | 2125TEXP | 24 | 2.125 | 3.680 | 48 | 1000 | Nitrogen | (i) |
| 0.254 | 14 | 2125TEXP | 28 | 2.125 | 3.706 | 48 | 1000 | Nitrogen | (i) |
| 0.254 | 15 | 2125TEXP | 34 | 2.125 | 3.788 | 48 | 1000 | Nitrogen | (i) |
| 0.254 | 56 | 2125TEXP | 40 | 2.125 | 3.817 | 48 | 1000 | Nitrogen | (i) | static pressure downhole, the expansion may be slightly less. Thus, testing in the open water tank may represent another "safety factor" as discussed herein, because the actual downhole expansion should not exceed that observed from a test in the open water tank, FIGS. 36A and 36B illustrate the results of a first test of nested tubulars T1, T2, T3 submerged in 2.5 feet of water in an open tank at ambient temperature. Innermost tubular T1 was a 5.5 inch, #20, P-110 pipe with a 0.361 inch wall thickness. Intermediate tubular T2 was a 7.625 inch, #26, L-80 pipe with a 0.328 inch wall thickness. Outermost tubular T3 was a 9.625 inch, #52.5, P-110 pipe with a 0.545 inch wall thickness. Intermediate tubular T2 was cemented between the innermost tubular T1 and the outermost tubular T3 via Portland cement C, C2 as shown in FIG. 36A. The expansion tool used in the test was a 1.750 inch (outer diameter) by 9 inch long explosive column Dual End Fired Expansion Charge (DEFEC). The total explosive weight was 493 grams HMX. The DEFEC was inserted into the central bore of the innermost tubular T1 of the submerged, nested tubulars in the open tank, and actuated one single time to determine whether detonating the explosive column would expand, without perforating or cutting through, portions of the walls of the nested tubulars T1, T2, T3 in a manner as discussed herein.

As a result of the single detonation of the 1.750 inch (outer diameter) by 9 inch long explosive column, protrusion P1 was formed in the wall of the innermost tubular T1 without perforating or cutting through the innermost tubular T1. FIG. 36B is a cross-sectional view of the nested tubulars T1, T2, T3 along line BB in FIG. 36A after the detonation, and shows that the outer diameter of the innermost tubular T1 at the protrusion P1 was increased from 5.5 inches to 6.320 inches. Protrusion P2 was formed in the wall of the intermediate tubular T2 without perforating or cutting through the intermediate tubular T2. FIG. 36B shows that the outer diameter of the intermediate tubular T2 at the protrusion P2 was increased from 7.625 inches to 8.168 inches. Protrusion P3 was formed in the wall of the outermost tubular T3 without perforating or cutting through the outermost tubular T3. FIG. 36B shows that the outer diameter of the outermost tubular T3 at the protrusion P3 was increased from 9.625 inches to 10.413 inches. In addition, the cement "C" in the annulus between the innermost tubular T1 and the intermediate tubular T2 was compressed "CC" by the protrusion P1 of the innermost tubular T1. The compression reduced the porosity of the cement "CC" by reducing the number of pores, channels, or other cement imperfections allowing annulus leaks, as discussed herein. Further, the cement "C2" in the annulus between the intermediate tubular T2 and the outermost tubular T3 was compressed "CC2" by the protrusion P2 of the intermediate tubular T2. The compression reduced the porosity of the cement "CC2" by reducing the number of pores, channels, or other cement imperfections allowing annulus leaks, as discussed herein. The pre-testing of the nested tubulars T1, T2, T3 in FIGS. 36A and 36B was thus successful.

Figures 37A, 37B:
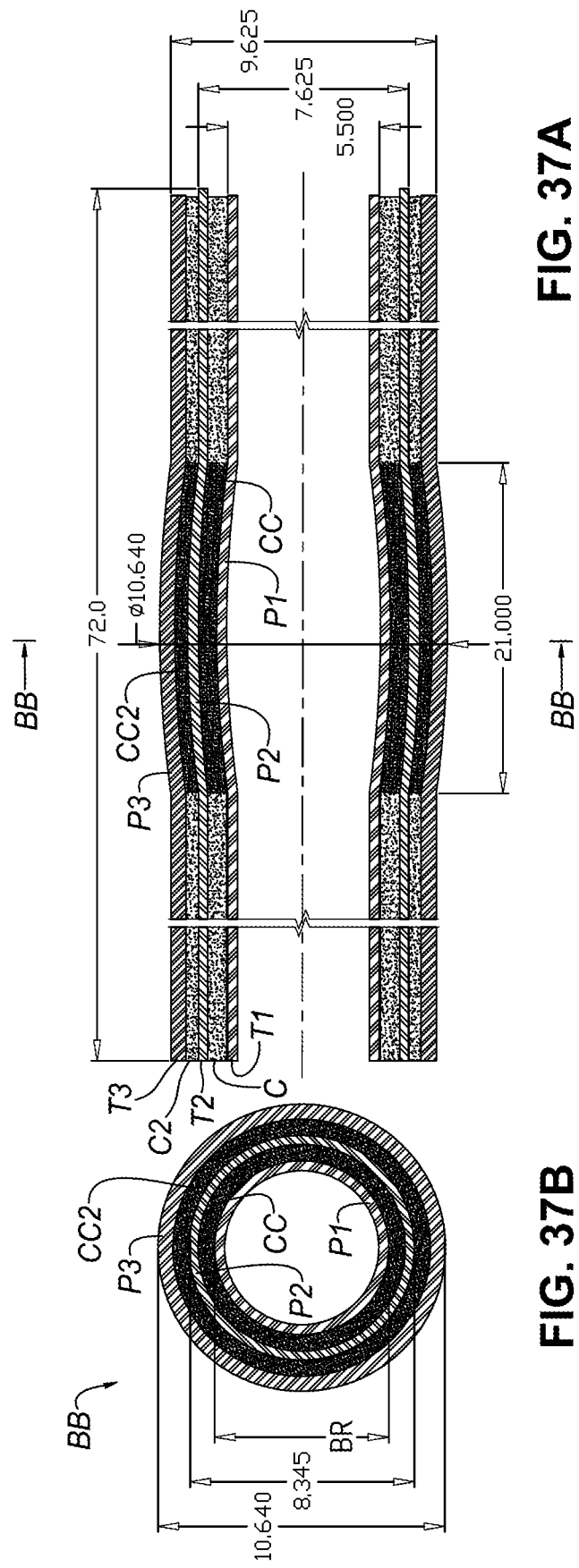

FIGS. 37A and 37B illustrate the results of a second test of nested tubulars T1, T2, T3 also submerged in 2.5 feet of water in an open tank at ambient temperature. Like the in the first test, the innermost tubular T1 was a 5.5 inch, #20, P-110 pipe with a 0.361 inch wall thickness. Intermediate tubular T2 was a 7.625 inch, #26, L-80 pipe with a 0.328 inch wall thickness. Outermost tubular T3 was a 9.625 inch, #52.5, P-110 pipe with a 0.545 inch wall thickness. Intermediate tubular T2 was cemented between the innermost tubular T1 and the outermost tubular T3 via Portland cement C, C2 as shown in FIG. 37A. The difference between the second test and the first test was that the second test used a 2.000 inch (outer diameter) by 9 inch long explosive column DEFEC having a total explosive weight of 655 grams HMX. In the second test, the DEFEC was inserted into the central bore of the innermost tubular T1 of the submerged, nested tubulars in the open tank, and actuated one single time to determine whether detonating the explosive column would expand, without perforating or cutting through, portions of the walls of the nested tubulars T1, T2, T3 in a manner as discussed herein.

As a result of the single detonation of the 2.000 inch (outer diameter) by 9 inch long explosive column, protrusion P1 was formed in the wall of the innermost tubular T1, but the wall at the protrusion P1 was breached. This indicates a pre-testing failure with respect to the innermost tubular T1. FIG. 37B is a cross-sectional view of the nested tubulars T1, T2, T3 along line BB in FIG. 37A after the detonation, and shows that the outer diameter of the innermost tubular T1 at the protrusion P1 was breached "BR". Protrusion P2 was formed in the wall of the intermediate tubular T2 without perforating or cutting through the intermediate tubular T2. FIG. 37B shows that the outer diameter of the intermediate tubular T2 at the protrusion P2 was increased from 7.625 inches to 8.345 inches. Protrusion P3 was formed in the wall of the outermost tubular T3 without perforating or cutting through the outermost tubular T3. FIG. 37B shows that the outer diameter of the outermost tubular T3 at the protrusion P3 was increased from 9.625 inches to 10.640 inches. In addition, the cement "C" in the annulus between the innermost tubular T1 and the intermediate tubular T2 was compressed "CC" by the breached protrusion P1 of the innermost tubular T1. Further, the cement "C2" in the annulus between the intermediate tubular T2 and the outermost tubular T3 was compressed "CC2" by the protrusion P2 of the intermediate tubular T2. The compression reduced the porosity of the cement "CC2" by reducing the number of pores, channels, or other cement imperfections allowing annulus leaks, as discussed herein.

Although several preferred embodiments have been illustrated in the accompanying drawings and describe in the foregoing specification, it will be understood by those of skill in the art that additional embodiments, modifications and alterations may be constructed from the principles disclosed herein. These various embodiments have been described herein with respect to selectively expanding a "pipe" or a "tubular." Clearly, other embodiments of the tool of the present invention may be employed for selectively expanding any tubular good including, but not limited to, pipe, tubing, production/casing liner and/or casing. Accordingly, use of the term "tubular" in the following claims is defined to include and encompass all forms of pipe, tube, tubing, casing, liner, and similar mechanical elements.

What is claimed is:

1. A method of determining a size and an explosive gram weight of an expansion charge able to selectively expand, without perforating or cutting through, a portion of a wall of a tubular in a wellbore, the method comprising:
 determining a size of a protrusion to be formed in the wall of the tubular;
 determining conditions in the wellbore, including:
  fluid/gas medium in the wellbore;
  hydrostatic pressure bearing on the tubular in the wellbore; and
  at least one physical characteristic of the tubular;

reproducing, at a second location other than the wellbore, at least one of the conditions determined in the wellbore;

providing a test tubular at the second location;

determining a size and an explosive gram weight of a test expansion charge able to expand, without perforating or cutting through, the wall of the test tubular, based on the at least one of the conditions determined in the wellbore;

positioning the test expansion charge comprising the determined size and explosive gram weight within the test tubular; and actuating the test expansion charge to expand the wall of the test tubular radially outward, without perforating or cutting through the wall of the test tubular, to form a test protrusion in the wall of the test tubular.

2. The method of claim 1, further comprising:

determining the size and the explosive gram weight of the expansion charge for expanding, without perforating or cutting through, the portion of the wall of the tubular in the wellbore based on at least one of:

the size and the explosive gram weight of the test expansion charge; and a size of the test protrusion.

3. The method of claim 1, wherein the at least one physical characteristic of the tubular comprises a material, a grade, a weight, an inner diameter, and an outer diameter.

4. The method of claim 1, wherein the test expansion charge is a shaped charge for use in a shaped charged expansion tool.

5. The method of claim 1, wherein the fluid/gas medium comprises at least one of air, water, and nitrogen.

6. The method of claim 1, wherein the fluid/gas medium comprises at least one of drilling fluid, completion fluid, acidizing fluid, salt water, and fresh water.

7. The method of claim 1, wherein the test tubular at the second location is unconfined such that an outer surface of the test tubular is exposed to a fluid/gas medium at the second location.

8. The method of claim 1, wherein the test tubular at the second location is confined such that an annulus adjacent an outer surface of the test tubular contains a solid material.

9. The method of claim 8, wherein the solid material is at least one of sand, cement, and a material present in an annulus adjacent an outer surface of the tubular in the wellbore.

10. The method of claim 8, wherein the test tubular at the second location is confined when the pressure in the wellbore is 5000 psi or less.

11. The method of claim 1, wherein the second location comprises one of a vessel and an open body of water.

12. A method of determining an expansion charge able to selectively expand, without perforating or cutting through, a portion of a wall of a tubular in a wellbore, the method comprising:

determining a size of a protrusion to be formed in the wall of the tubular;

determining conditions in the wellbore, including:
hydrostatic pressure bearing on the tubular in the wellbore; and
at least one physical characteristic of the tubular;

reproducing, at a second location other than the wellbore, at least one of the conditions determined in the wellbore;

providing a test tubular at the second location;

determining a test expansion charge able to expand, without perforating or cutting through, the wall of the test tubular, based on the at least one of the conditions determined in the wellbore;

positioning the determined test expansion charge within the test tubular; and actuating the determined test expansion charge to expand the wall of the test tubular radially outward, without perforating or cutting through the wall of the test tubular, to form a test protrusion in the wall of the test tubular.

13. The method of claim 12, further comprising:

determining a size and an explosive gram weight of the expansion charge, for expanding, without perforating or cutting through, the portion of the wall of the tubular in the wellbore based on at least one of:

a size and an explosive gram weight of the test expansion charge; and a determined size of the test protrusion.

14. The method of claim 12, wherein the test expansion charge is a shaped charge for use in a shaped charged expansion tool.

15. The method of claim 12, further comprising a fluid/gas medium in the wellbore as part of the determining conditions in the wellbore.

16. The method of claim 15, wherein the fluid/gas medium comprises at least one of air, water, nitrogen, drilling fluid, completion fluid, acidizing fluid, salt water, and fresh water.

17. The method of claim 12, wherein the test tubular at the second location is confined such that an annulus adjacent an outer surface of the test tubular contains at least one of sand, cement and a material present in an annulus adjacent an outer surface of the tubular in the wellbore.

18. The method of claim 12, wherein the test tubular at the second location is unconfined such that an outer surface of the test tubular is exposed to a fluid/gas medium at the second location.

* * * * *